(12) United States Patent
Mangelsdorf et al.

(10) Patent No.: US 10,117,878 B2
(45) Date of Patent: Nov. 6, 2018

(54) LIGANDS FOR NEMATODE NUCLEAR RECEPTORS AND USES THEREOF

(71) Applicant: Board of Regents, University of Texas System, Austin, TX (US)

(72) Inventors: David J. Mangelsdorf, Dallas, TX (US); Richard J. Auchus, Dallas, TX (US); Daniel L. Motola, Brookline, MA (US); Carolyn L. Cummins, Dallas, TX (US); Kamalesh K. Sharma, Dallas, TX (US)

(73) Assignee: Board of Regents, University of Texas System, Austin, TX (US)

( * ) Notice: Subject to any disclaimer, the term of this patent is extended or adjusted under 35 U.S.C. 154(b) by 775 days.

(21) Appl. No.: 13/673,696

(22) Filed: Nov. 9, 2012

(65) Prior Publication Data

US 2013/0137667 A1    May 30, 2013

Related U.S. Application Data

(60) Continuation of application No. 12/905,459, filed on Oct. 15, 2010, now abandoned, which is a division of application No. 11/683,742, filed on Mar. 8, 2007, now Pat. No. 7,825,269.

(60) Provisional application No. 60/780,050, filed on Mar. 8, 2006.

(51) Int. Cl.
   *C07J 9/00* (2006.01)
   *A61K 31/575* (2006.01)

(52) U.S. Cl.
   CPC .............. *A61K 31/575* (2013.01); *C07J 9/00* (2013.01); *C07J 9/005* (2013.01); *Y02P 20/582* (2015.11)

(58) Field of Classification Search
   USPC .................................................. 552/546, 547
   See application file for complete search history.

(56) References Cited

U.S. PATENT DOCUMENTS

2004/0213771 A1    10/2004   Sluder et al.

FOREIGN PATENT DOCUMENTS

WO    WO-2005/084208 A2    9/2005

OTHER PUBLICATIONS

Udalova et al., Applied Biochemistry and Microbiology, vol. 40, No. 1, 2004 (Year: 2004).*
Alain Rahier, "Deuterated Delta 7-Cholesterol Analogues as Mechanistic Probes for Wild-Type and Mutated Delta7-Sterol-C5(6)-desaturase", Biochemistry, 2001, 40, pp. 256-267.

Albert, P. S., and Riddle, D. L., "Mutants of Caenorhabditis elegans That Form Dauer-like Larvae", Developmental Biology 126, (1988), pp. 270-293.
Antebi, A., Culotti, J. G., and Hedgecock, E. M. "daf-12 regulates developmental age and the dauer alternative in Caenorhabditis elegans". Development 125, (1998), pp. 1191-1205.
Antebi, A., Yeh, W. H., Tait, D., Hedgecock, E. M., and Riddle, D. L.,"daf-12 encodes a nuclear receptor that regulates the dauer diapause and developmental age in C. elegans". Genes & Development, 14, (2000), pp. 1512-1527.
Axelson et al., "Bile Acid Syntehsis in Cultured Human Hepatoblastoma Cells", J. Biol. Chem.. 266 (27) 17770-17777 (1991).
B. Gerisch et al., "Hormonal signals produced by DAF-9/cytochrome P450 regulate C. elegans dauer diapause in response to environmental cues", Development 131, p(2004), pp. 1765-1776.
Brenner S. , "The Genetics of Caenorhabditis Elegans", Genetics, 77, May 1974, pp. 71-94.
Cali, J. J., and Russell, D. W., Characterization of Human Sterol 27-Hydroxylase. A Mitochondrial Cytochrome P-450 that Catalyzes Multiple Oxidation Reaction in Bile AcidBbiosynthesis. J Biol Chem 266, (1991), 7774-7778.
CAplus structures, Axelson et al., 1991.
Caputo et al., Triterpenes of galls of Pistacia terebinthus : Galls produced by Pemphigus utricularius. (Phytochem. 14(3), 809-811, (1975).
Cheng, J.B., Motola, D.L., Mangelsdorf, D.J., and Russell, D.W., "De-orphanization of cytochrome P450 2R1: a microsomal vitamin D 25-hydroxilase",. J Biol Chem, 2003. 278(39): p. 38084-38093.
Chitwood, D. J., Lusby, W. R., Lozano, R., Thompson, M. J., and Svoboda, J. A. "Novel nuclear methylation of sterols by the nematode *Caenorhabditis elegans*". Steroids 42, (1983) pp. 311-319.
D.J. Chitwood, "Biochemistry and function of nematode steroids", Crit. Rev. Biochem. Mol. Biol. 34, (1999), pp. 273-284.
David J. Chitwood, "An Inside Job Using Nematodes' own biology against them", Agricultural Research, Aug. 2004, pp. 16-17.
Final Office Action on U.S. Appl. No. 11/683,742, dated Mar. 11, 2010.

(Continued)

*Primary Examiner* — Jeffrey S Lundgren
*Assistant Examiner* — Michael J Schmitt
(74) *Attorney, Agent, or Firm* — Parker Highlander PLLC

(57) ABSTRACT

An effective anti-nematode methodology entails contacting nematodes with a biologically effective amount of at least one compound according to formula I:

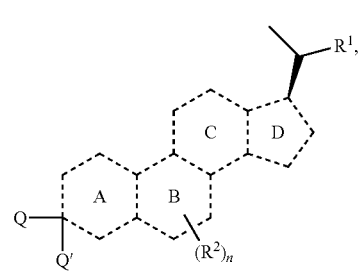

where Q, Q', $R^1$, $R^2$, and n are defined herein, or with a stereoisomer, solvate, or pharmaceutically acceptable salt of such compound.

9 Claims, 30 Drawing Sheets

(56) References Cited

OTHER PUBLICATIONS

Gerisch, B., Weitzel, C., Kober-Eisermann, C., Rottiers, V., and Antebi, A. (2001). A hormonal signaling pathway influencing C. elegans metabolism, reproductive development, and life span. Dev Cell 1, 841-851.

Gill, M. S., Held, J. M., Fisher, A. L., Gibson, B. W., and Lithgow, G. J. (2004). Lipophilic regulator of a developmental switch in Caenorhabditis elegans. Aging Cell 3, 413-421.

Gissendanner, C. R., Crossgrove, K., Kraus, K. A., Maina, C. V., and Sluder, A. E. (2004). Expression and function of conserved nuclear receptor genes in Caenorhabditis elegans. Dev Biol 266, 399-416.

Hood, S. R., Shah, G., and Jones, P. (1996)."Expression of Cytochromes P450 in a Baculovirus System," Methods in Molecular Biology, I. R. Phillips and E. A. Shephard, eds. (Totowa, NJ: Humana Press), pp. 203-217.

Hsin, H., and Kenyon, C. (1999). "Signals from the reproductive system regulate the lifespan of C. elegans", Nature 399, 362-366.

International Search Report and Written Opinion for PCT/US07/05944, dated Oct. 5, 2007.

Jia, K., Albert, P. S., and Riddle, D. L. (2002). "DAF-9, a cytochrome P450 regulating C. elegans larval development and adult longevity". Development 129, pp. 221-231.

Kim, H.-S., Wilson, W. K., Needleman, D. H., Pinkerton, F. D., Wilson, D. K., Quiocho, F. A., and Schroepfer, Jr., G. J. (1989). "Inhibitors of sterol synthesis. Chemical synthesis, structure, and biological activities of (25R)-3 beta,26-dihydroxy-5 alpha-cholest-8(14)-en-15-one, a metabolite of 3 beta-hydroxy-5 alpha-cholest-8(14)-en-15-one", Journal Lipid Research 30:247-261.

Kimura, K. D., Tissenbaum, H. A., Liu, Y., and Ruvkun, G. (1997). "daf-2, an insulin receptor-like gene that regulates longevity and diapause in Caenorhabditis elegans". Science 277, 942-946.

Larsen, P. L., Albert, P. S., and Riddle, D. L. (1995). "Genes that regulate both development and longevity in Caenorhabditis elegans". Genetics 139, 1567-1583.

Li, J., Brown, G., Ailion, M., Lee, S., and Thomas, J. H. (2004). "NCR-1 and NCR-2, the C. elegans homologs of the human Niemann-Pick type C1 disease protein, function upstream of DAF-9 in the dauer formation pathways". Development 131, 5741-5752.

Lindblom, T. H., Pierce, G. J., and Sluder, A. E. (2001). "A C. elegans orphan nuclear receptor contributes to xenobiotic resistance". Curr Biol 11, 864-868.

Liping Chen et al., "Coexpression of Cytochrome P4502A6 and Human NADPH-P450 Oxidoreductase in the Baculovirus System", Drug Metabolism and Disposition, vol. 25, No. 4, 1997, pp. 399-405.

Liu et al. (1996). Drug Therapy: Antiparasitic Drugs. New England J. Med. 334, 1178-1184.

Ludewig, A. H., Kober-Eisermann, C., Weitzel, C., Bethke, A., Neubert, K., Gerisch, B., Hutter, H., and Antebi, A. (2004). "A novel nuclear receptor/coregulator complex controls C. elegans lipid metabolism, larval development, and aging". Genes Dev 18, 2120-2133.

Mak, H. Y., and Ruvkun, G. (2004). Intercellular signaling of reproductive development by the C. elegans DAF-9 cytochrome P450. Development 131, 1777-1786.

Makishima, M., Okamoto, A. Y., Repa, J. J., Tu, H., Learned, R. M., Luk, A., Hull, M. V., Lustig, K. D., Mangelsdorf, D. J., and Shan, B. (1999). Identification of a nuclear receptor for bile acids. Science 284, 1362-1365.

Margherita Gavagnin et al., "Structure and Synthesis of a Progesterone Homologue from the Skin of the Dorid Nudibranch Aldisa smaragdina", Eur. J. Org. Chem. 2002, 1500-1504.

Matyash, V., Entchev, E. V., Mende, F., Wilsch-Brauninger, M., Thiele, C., Schmidt, A. W., Knolker, H. J., Ward, S., and Kurzchalia, T. V. (2004). Sterol-derived hormone(s) controls entry into diapause in Caenorhabditis elegans by consecutive activation of DAF-12 and DAF-16. PLoS Biol 2, e280, pp. 1561-1571.

Merris, M., Wadsworth, W. G., Khamrai, U., Bittman, R., Chitwood, D. J., and Lenard, J. (2003). Sterol effects and sites of sterol accumulation in Caenorhabditis elegans: developmental requirement for 4alpha-methyl sterols. J Lipid Res 44, 172-181.

Mooijaart, S. P., Brandt, B. W., Baldal, E. A., Pijpe, J., Kuningas, M., Beekman, M., Zwaan, B. J., Slagboom, P. E., Westendorp, R. G., and van Heemst, D. (2005). C. elegans DAF-12, Nuclear Hormone Receptors and human longevity and disease at old age. Ageing Res Rev 4, 351-371.

Morissette et al., "High-throughput crystallization; polymorphs, salts, co-crystals and solvates of pharmaceutical solids" Adv. Drug Del. Rev. 56 (2004), pp. 275-300.

Non-Final Office Action on U.S. Appl. No. 11/683,742, dated Aug. 17, 2009.

Norlin, M., von Bahr, S., Bjorkhem, I., and Wikvall, K. (2003). On the substrate specificity of human CYP27A1: implications for bile acid and cholestanol formation. J Lipid Res 44, 1515-1522.

Notice of Allowance on U.S. Appl. No. 11/683,742, dated Jun. 24, 2010.

Owen et al., "The degradation of cholesterol by *Pseudomonas* sp. NCIB 10590 under aerobic conditions", J. Lipid Res. 24, 1500-1511, (1983).

Ren, P., Lim, C. S., Johnsen, R., Albert, P. S., Pilgrim, D., and Riddle, D. L. (1996). Control of C. elegans larval development by neuronal expression of a TGF-beta homolog. Science 274, 1389-1391.

Riddle, D. L., and Albert, P. S. (1997). Genetic and environmental regulation of dauer larva development., In C. elegans II, D. L. Riddle, B. Meyer, J. Priess, and T. Blumenthal, eds. (Colds Spring Harbor: Cold Spring Harbor Laboratory Press), pp. 739-768.

Russell, D. W. (2003). The enzymes, regulation, and genetics of bile acid synthesis. Ann Rev Biochem 72, 137-174.

Sangster N.C., and Gill, J. (1999). Pharmacology of anthelmintic resistance. Parasitol Today 15, 141-146.

Schackwitz, W. S., Inoue, T., and Thomas, J. H. (1996). Chemosensory neurons function in parallel to mediate a pheromone response in C. elegans. Neuron 17, 719-728.

Shostak, Y., Van Gilst, M. R., Antebi, A., and Yamamoto, K. R. (2004). Identification of C. elegans DAF-12-binding sites, response elements, and target genes. Genes Dev 18, 2529-2544.

Siddiqui, A. A., Stanley, C. S., Berk, S. L., and Skelly, P. J. (2000) A cDNA encoding a nuclear hormone receptor of the steroid/thyroid hormone-receptor superfamily from the human parasitic nematode *Strongyloides stercoralis*. Parasitol. Res. 86, 24-29.

Sluder, A. E., and Maina, C. V. (2001). Nuclear receptors in nematodes: themes and variations. Trends Genet 17, 206-213.

Stiernagel, T. (1999). Maintenance of C. elegans, In C. elegans: A Practical Approach, I. A. Hope, ed. (New York: Oxford University Press), pp. 51-67.

Thierry Haag et al., "Synthesis of Putative Precursors of Ecdysone. Part 3. synthesis of 3β,14a25-Trihydroxy-5β-cholest-7-en-6-one", J. Chem. Soc. Perkin Trans. 1, 1988, pp. 2353-2363.

Umesono, K., Murakami, K. K., Thompson, C. C., and Evans, R. M. (1991). Direct repeats as selective response elements for the thyroid hormone, retinoic acid, and vitamin D3 receptors. Cell 65, 1255-1266.

Uomori, A., Seo, S., Sato, T., Yoshimura, Y., and Takeda, K. (1987) Synthesis of (25R)-[26-2H1]Cholesterol and 1H N.m.r. and H.p.l.c. Resolution of (25R)- and (25S)-26-Hydroxycholesterol. J. Chem. Soc. Perkin Trans. 1, 1713-1718.

Van Gilst, M. R., Hadjivassiliou, H., and Yamamoto, K. R. (2005b). From the Cover: A Caenorhabditis elegans nutrient response system partially dependent on nuclear receptor NHR-49. Proc Natl Acad Sci U S A 102, 13496-13501.

Van Gilst, M. R., Hadjivassiliou, H., Jolly, A., and Yamamoto, K. R. (2005a). Nuclear hormone receptor NHR-49 controls fat consumption and fatty acid composition in C. elegans. PLoS Biol 3, e53, pp. 0301-0312.

Vippagunta et al., "Crystalline solids", Adv. Drug. Del. Rev. 48 (2001) 3-26.

Willy, P. J., Umesono, K., Ong, E. S., Evans, R. M., Heyman, R. A., and Mangelsdorf, D. J. (1995). LXR, a nuclear receptor that defines a distinct retinoid response pathway. Genes Dev 9, 1033-1045.

Xu, H. E., Stanley, T. B., Montana, V. G., Lambert, M. H., Shearer, B. G., Cobb, J. E., McKee, D. D., Galardi, C. M., Plunket, K. D.,

(56) References Cited

OTHER PUBLICATIONS

Nolte, R. T., et al. (2002). Structural basis for antagonist-mediated recruitment of nuclear co-repressors by PPARalpha. Nature 415, 813-817.
Yu, B. and Tao, H. (2002). "Glycosyl Trifluoroacetimidates.2. Synthesis of Dioscin and Xiebai Saponin I", Journal of Organic Chemistry. 67, 9099-9102.
Zhang, Z., Li, D., Blanchard, D. E., Lear, S. R., Erickson, S. K., and Spencer, T. A. (2001). Key regulatory oxysterols in liver: analysis as delta4-3-ketone derivatives by HPLC and response to physiological perturbations. Journal of Lipid Research 42, 649-658.
Zheng, Y., and Li, Y.. (2003). Novel stereoselective synthesis of 7beta-methyl-substituted 5-androstene derivatives. J.Org.Chem. 68, 1603-1606 (2003).

* cited by examiner

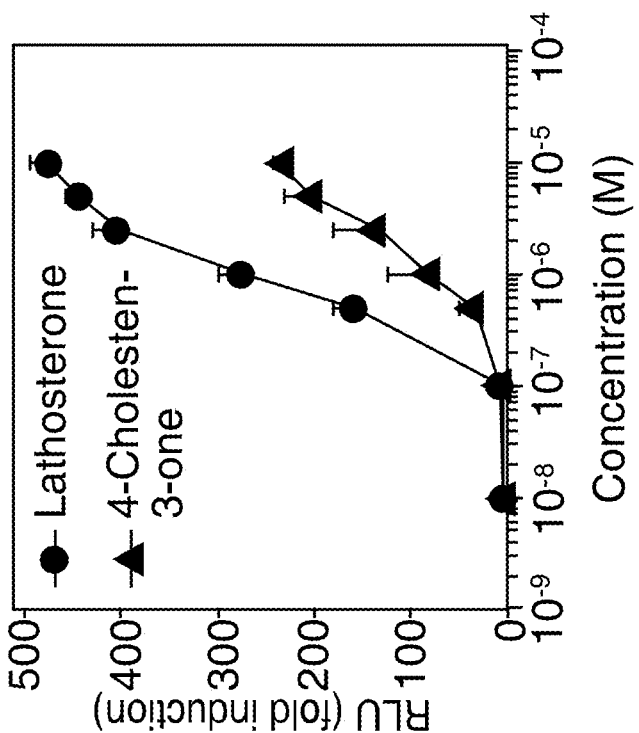
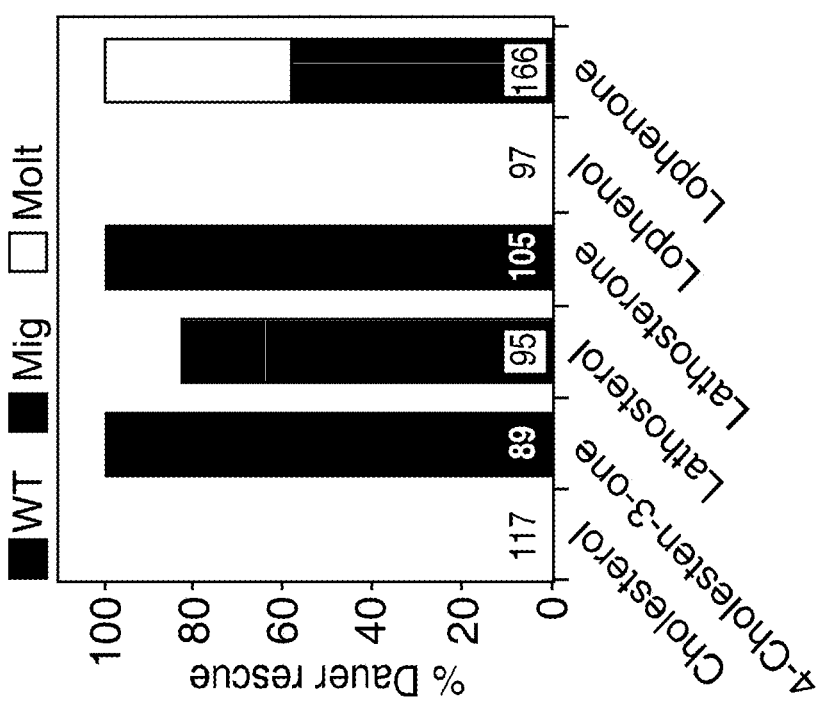
FIGURE 1E
FIGURE 1D

*FIGURE 3A*
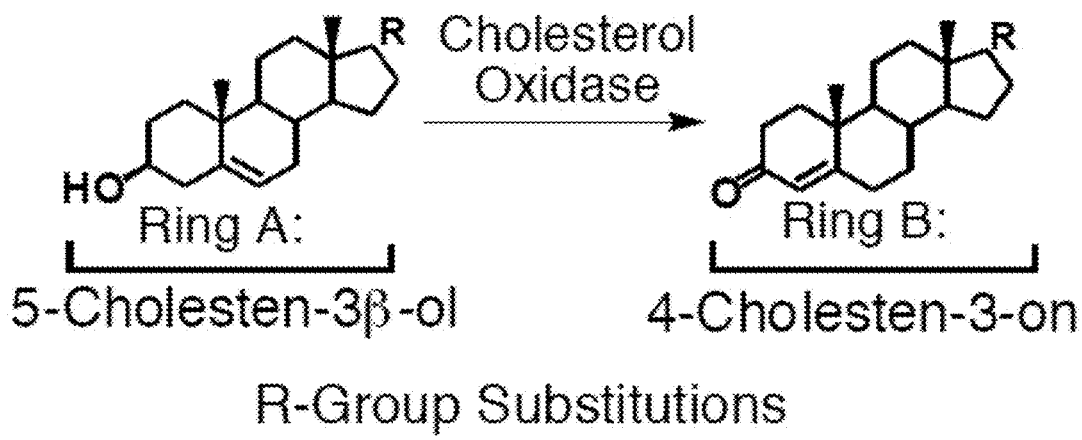
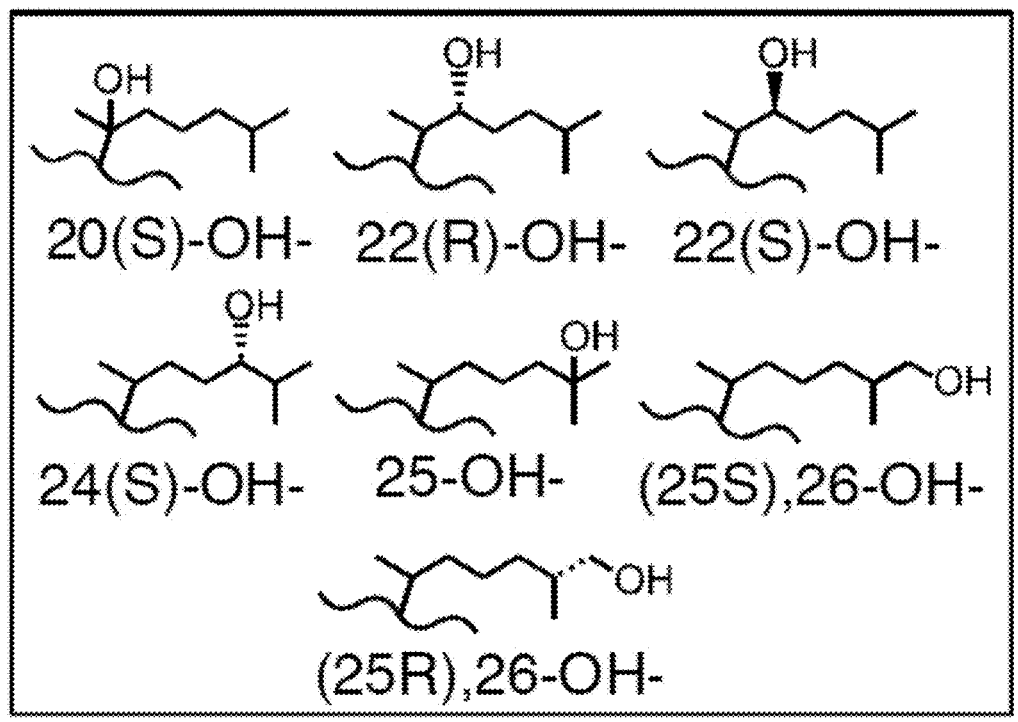

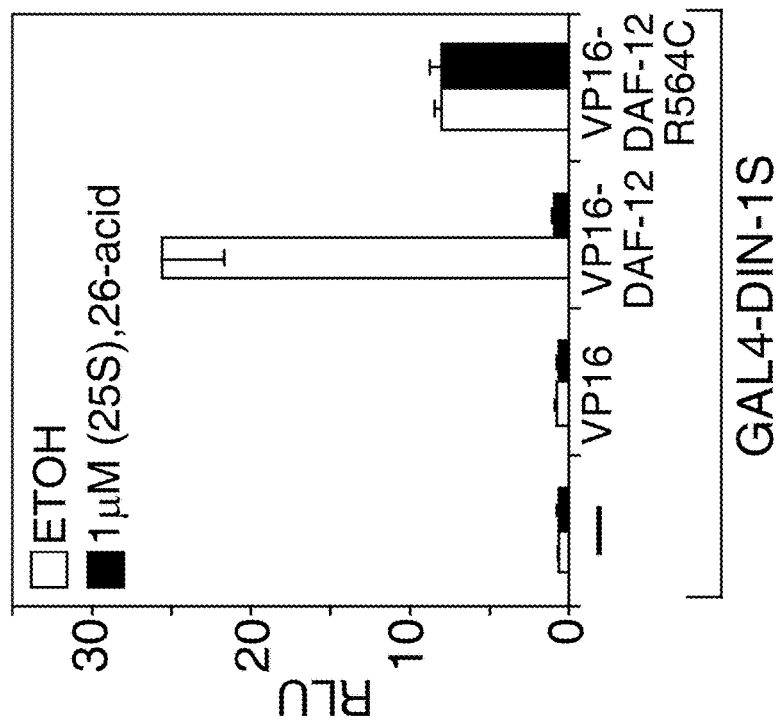
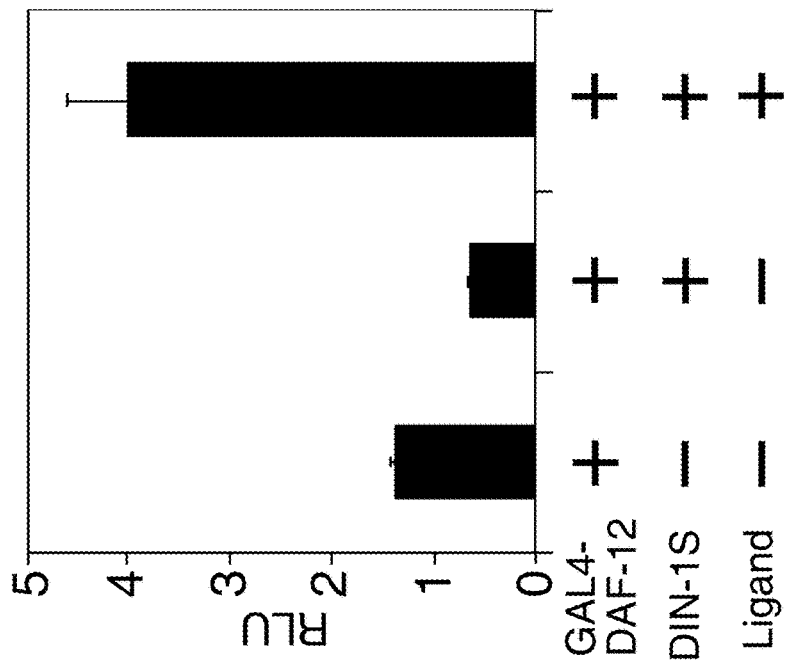

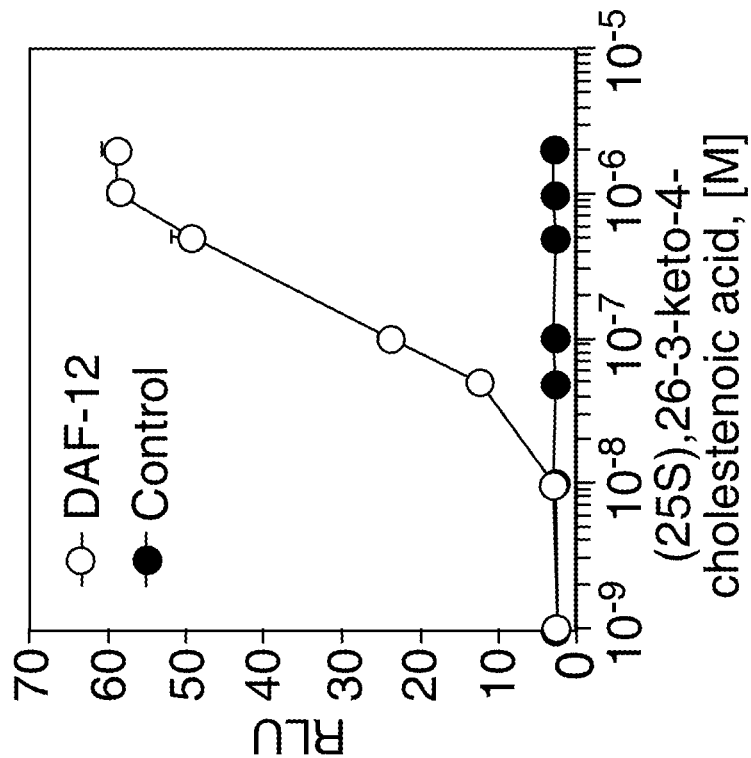
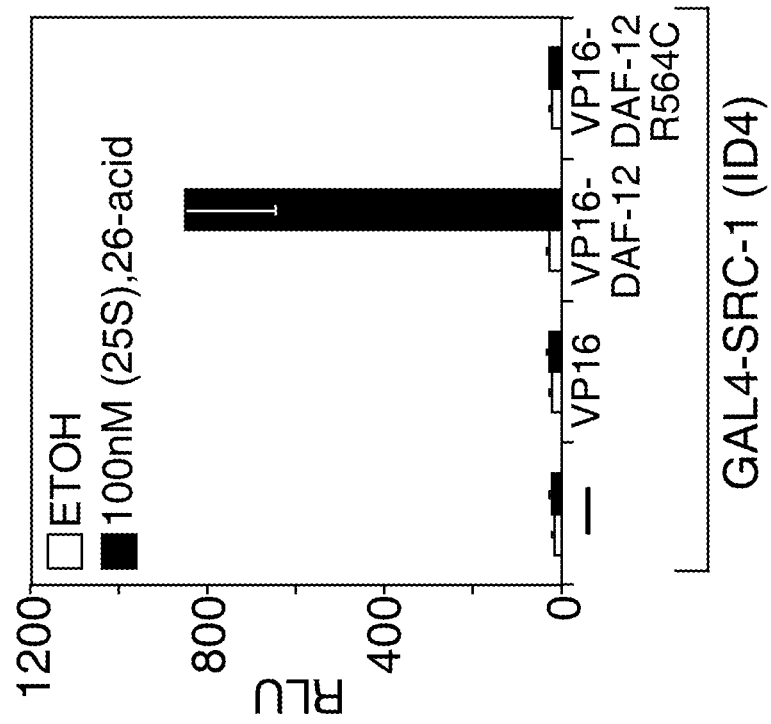

Δ⁴-Dafachronic Acid
(3-Keto-4-cholestenoic acid)

Δ⁷-Dafachronic Acid
(3-Keto-7,(5α)-cholestenoic acid)

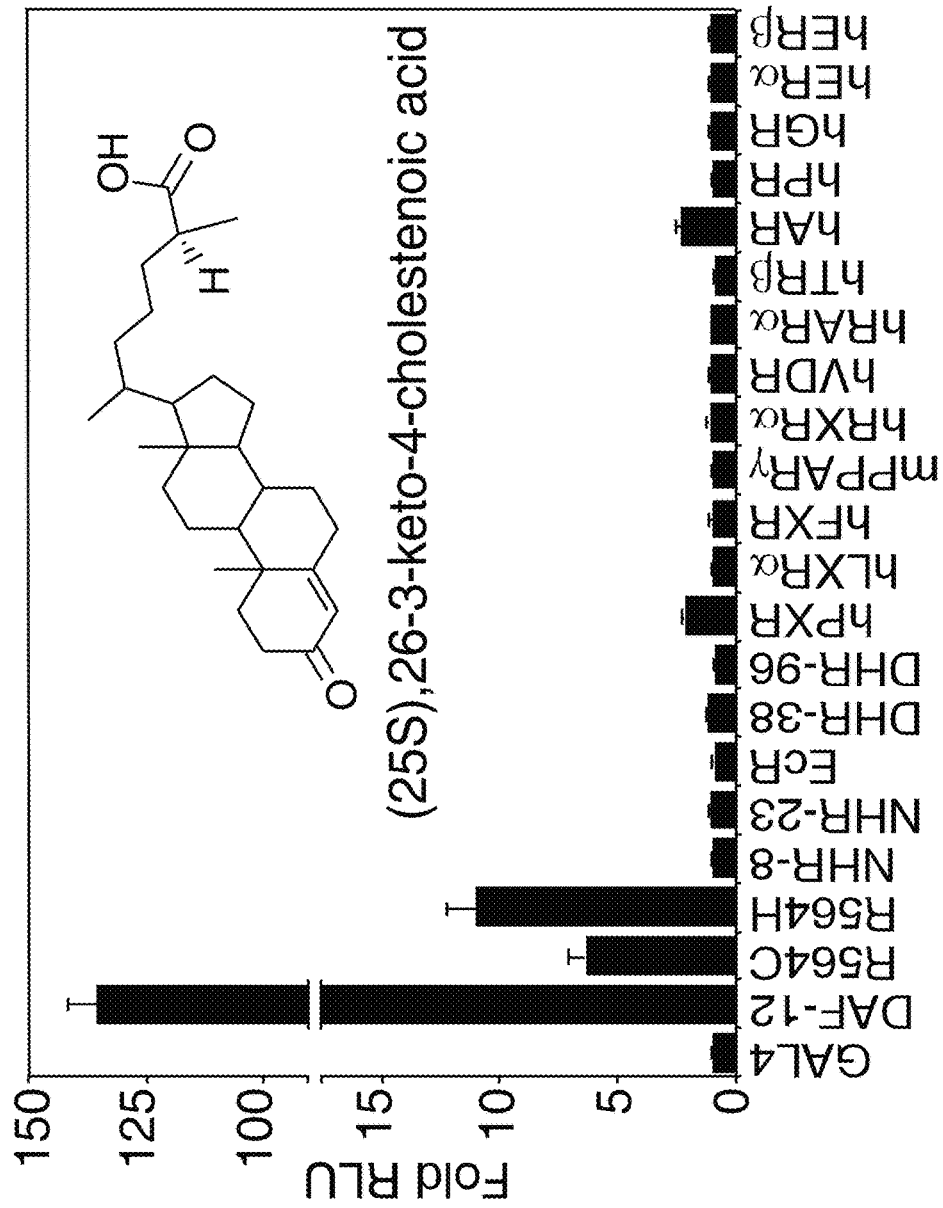

*FIGURE 11A*

| Compound | Structure | ¹H NMR (400 MHz) |
|---|---|---|
| (25S),26-3-keto-4-cholestenoic acid | 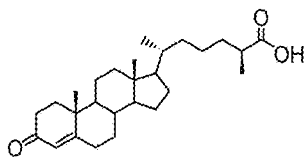 | H4, δ = 5.71 ppm (s, 1H)<br>H18, δ = 0.69 ppm (s, 3H)<br>H19, δ = 1.16 ppm (s, 3H)<br>H21, δ = 0.89 ppm (d, 3H, $J$ = 6.8 Hz)<br>H27, δ = 1.17 ppm (d, 3H, $J$ = 6.4 Hz)<br>No detectable impurities |
| (25R),26-3-keto-4-cholestenoic acid | 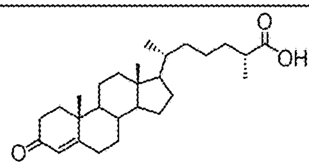 | H4, δ = 5.72 ppm (s, 1H)<br>H18, δ = 0.69 ppm (s, 3H)<br>H19, δ = 1.17 ppm (s, 3H)<br>H21, δ = 0.89 ppm (d, 3H, $J$ = 6.8 Hz)<br>H27, δ = 1.17 ppm (d, 3H, $J$ = 6.4 Hz)<br>>95% pure |
| (25S),26-hydroxy-4-cholesten-3-one | 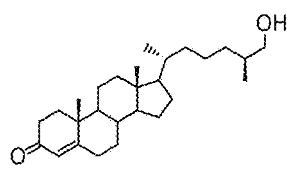 | H4, δ = 5.71 ppm (s, 1H)<br>H26a, δ = 3.41 ppm (dd, 1H, $J$ = 10.4, 5.6 Hz)<br>H26b, δ = 3.50 ppm (dd, 1H, $J$ = 10.4, 6.4 Hz)<br>H18, δ = 0.70 ppm (s, 3H)<br>H19, δ = 1.17 ppm (s, 3H)<br>H21, δ = 0.90 ppm (d, 3H, $J$ = 6.4 Hz)<br>H27, δ = 0.91 ppm (d, 3H, $J$ = 6.4 Hz)<br>No detectable impurities |
| (25R),26-hydroxy-4-cholesten-3-one | 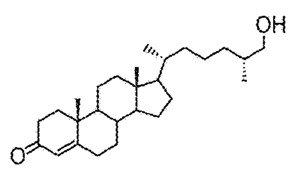 | H4, δ = 5.73 ppm (s, 1H)<br>H26a, δ = 3.43 ppm (dd, 1H, $J$ = 10.4, 5.6 Hz)<br>H26b, δ = 3.52 ppm (dd, 1H, $J$ = 10.4, 6.4 Hz)<br>H18, δ = 0.71 ppm (s, 3H)<br>H19, δ = 1.19 ppm (s, 3H)<br>H21, δ = 0.92 ppm (d, 3H, $J$ = 6.8 Hz)<br>H27, δ = 0.93 ppm (d, 3H, $J$ = 6.4 Hz)<br>No detectable impurities |
| 20(S)-hydroxy-4-cholesten-3-one | 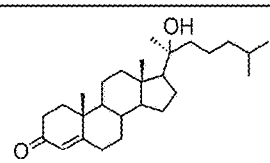 | H4, δ = 5.71 ppm (s, 1H)<br>H18, δ = 0.85 ppm (s, 3H)<br>H19, δ = 1.17 ppm (s, 3H)<br>H21, δ = 1.26 ppm (s, 3H)<br>H26, H27, δ = 0.87 ppm (d, 6H, $J$ = 6.4 Hz)<br>>95% pure |

Supplementary Table 1A
Motola et al.

*FIGURE 11B*

| Compound | Structure | ¹H NMR (400 MHz) |
|---|---|---|
| 22(R)-hydroxy-4-cholesten-3-one | 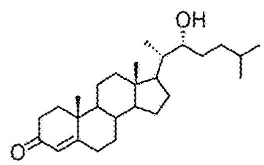 | H4, δ = 5.71 ppm (s, 1H)<br>H18, δ = 0.72 ppm (s, 3H)<br>H19, δ = 1.17 ppm (s, 3H)<br>H21, δ = 0.91 ppm (d, 3H, $J$ = 6.4 Hz)<br>H22, δ = 3.59 ppm (br d, 1H, $J$ = 8 Hz)<br>H26, H27 δ = 0.88 ppm (d, 3H, $J$ = 6.4 Hz);<br>δ = 0.89 ppm (d, 3H, $J$ = 6.4 Hz)<br>3-5% Δ5 (~95% pure) |
| 22(S)-hydroxy-4-cholesten-3-one | 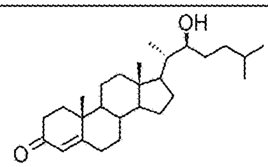 | H4, δ = 5.71 ppm (s, 1H)<br>H18, δ = 0.71 ppm (s, 3H)<br>H19, δ = 1.17 ppm (s, 3H)<br>H22, δ = 3.61 ppm (br m, 1H)<br>H21, H26, H27 δ = 0.88 ppm (br d, 9H, $J$ = 6.8 Hz)<br>No detectable impurities |
| 24(S)-hydroxy-4-cholesten-3-one | 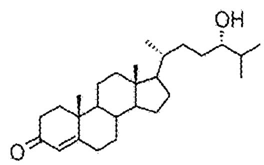 | H4, δ = 5.71 ppm (s, 1H)<br>H18, δ = 0.70 ppm (s, 3H)<br>H19, δ = 1.17 ppm (s, 3H)<br>H21, δ = 0.88 ppm (d, 3H, $J$ = 6.8 Hz)<br>H24, δ = 3.30 ppm (br m, 1H)<br>H26, H27, δ = 0.91 ppm (d, 3H, $J$ = 6.8 Hz);<br>δ = 0.92 ppm (d, 3H, $J$ = 6.8 Hz)<br>No detectable impurities |
| 25-hydroxy-4-cholesten-3-one | 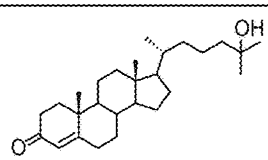 | H4, δ = 5.71 ppm (s, 1H)<br>H18, δ = 0.69 ppm (s, 3H)<br>H19, δ = 1.17 ppm (s, 3H)<br>H21, δ = 0.91 ppm (d, 3H, $J$ = 6.4 Hz)<br>H26, H27, δ = 1.20 ppm (br s, 6H)<br>No detectable impurities |
| lathosterone | 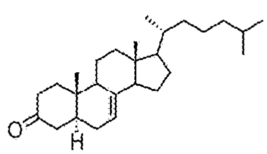 | H7, δ = 5.17 ppm (dd, 1H, $J$ = 4.4, 1.6 Hz)<br>H18, δ = 0.55 ppm (s, 3H)<br>H19, δ = 1.00 ppm (s, 3H)<br>H21, δ = 0.91 ppm (d, 3H, $J$ = 6.8 Hz)<br>H26, H27, δ = 0.85 ppm (d, 3H, $J$ = 6.8 Hz);<br>δ = 0.86 ppm (d, 3H, $J$ = 6.4 Hz);<br>No detectable impurities |
| lophenone | 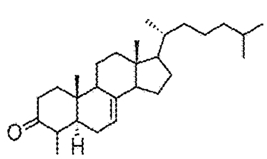 | H4α, δ = 0.99 ppm (d, 3H, $J$ = 6.4 Hz)<br>H7, δ = 5.19 ppm (dd, 1H, $J$ = 6.0, 1.6 Hz)<br>H18, δ = 0.55 ppm (s, 3H)<br>H19, δ = 1.07 ppm (s, 3H)<br>H21, δ = 0.91 ppm (d, 3H, $J$ = 6.8 Hz)<br>H26, H27, δ = 0.85 ppm (d, 3H, $J$ = 6.8 Hz);<br>δ = 0.86 ppm (d, 3H, $J$ = 6.8 Hz);<br>No detectable impurities |

Supplementary Table 1B
Motola et al.

LIGANDS FOR NEMATODE NUCLEAR RECEPTORS AND USES THEREOF

This application is a continuation application of U.S. patent application Ser. No. 12/905,459, filed Oct. 15, 2010, which is a divisional application of U.S. patent application Ser. No. 11/683,742, filed Mar. 8, 2007, which claims the benefit of priority to U.S. provisional patent application No. 60/780,050, filed on Mar. 8, 2006. The respective contents of these applications are incorporated herein by reference.

BACKGROUND OF THE INVENTION

Field of the Invention

The present invention relates generally to the field of anti-nematode compounds and methods of using the same.

State of the Art

Nematodes are elongated symmetrical roundworms that constitute one of the largest and most successful phyla in the animal kingdom. Many nematode species are free-living and feed on bacteria, whereas others have evolved into parasites of plants and animals, including humans. Human infections with parasitic nematodes are among the most prevalent infections worldwide. Over one billion people, predominantly in tropical and subtropical developing countries, are infected with soil and vector-borne nematodes that cause a variety of debilitating diseases. Liu et al., "Intestinal Nematodes" in 181 HARRISON's PRINCIPLES OF INTERNAL MEDICINE 916-20 (McGraw-Hill, 1994).

Among these parasitic nematodes are *Ancylostoma* and *Necator* hookworms, which cause anemia and malnutrition, *Ascaris* roundworms, that can cause pulmonary and nutritional disorders, and *Strongyloides stercoralis*, that can effect a potentially life-threatening intestinal infection. Nematodes of the order Spirurida are responsible for onchocerciasis (river blindness) and lymphatic filariasis. Animal parasitic nematodes infect a wide variety of both domestic and wild animals. Major animal pathogens include *Haemonchus contortus*, which infects herbivorous vertebrates, *Trichinella spiralis*, the causative agent of trichinosis, and various members of the order Ascaridida, which infect pigs and dogs in addition to humans.

Plant parasitic nematodes also represent major agricultural problems and are responsible for many billions of dollars in economic losses annually. The most economically damaging plant parasitic nematode genera belong to the family Heterderidae of the order *Tylenchida*, and include the cyst nematodes (genera *Heterodera* and *Globodera*) and the root-knot nematodes (genus *Meloidogyne*). The soybean cyst nematode (*H. glycines*) and potato cyst nematodes (*G. pallida* and *G. rostochiensis*) are important examples. Root-knot nematodes infect thousands of different plant species including vegetables, fruits, and row crops. In contrast to many viral and bacterial pathogens, little is known about the molecular basis of nematode parasitism, limiting the available framework for rational anti-helminthic (anti-nematode) drug development. See David and Liu, "Molecular biology and immunology of parasitic infections," in HARRISON's PRINCIPLES OF INTERNAL MEDICINE 865-71 (McGraw-Hill, 1994).

Anti-nematode drug or pesticide discovery traditionally has relied on direct screening of compounds against whole target organisms or on chemical modification of existing compounds. These strategies have yielded relatively few classes of agents, acting against a limited number of known biological targets. For example, organophosphates and carbamates, the oldest extant class of nematicides, were developed many decades ago and target a single, biologically conserved enzyme, acetylcholinesterase. Imidazole derivatives such as benzimidazole exert their antiparasitic effects by binding tubulin. Levamisole acts as an agonist on the nicotinic acetylcholine receptor, and avermectins act as irreversible agonists at glutamate-gated chloride channels (Liu et al., 1996).

Unfortunately, there are certain debilitating nematode infections that are difficult if not impossible to cure with existing therapeutics. In onchocerciasis, for instance, the adult female *Onchocerca volvulus* worms are refractory to even newer generation drugs (Liu et al., 1996). In addition, drug resistance has emerged to all of these main classes of therapeutics, particularly in livestock animal applications in which their use is widespread (Sangster et al., 1999). To date it has not been possible to develop effective and practical vaccines. Even were such vaccines available, effective anti-nematode drugs still would be needed, for treating established infections and for offering the potential advantages of prophylaxis and treatment against a broad spectrum of nematode parasites.

The drawbacks of existing agents that are currently used to control plant parasitic nematodes are equally or more significant. Fumigant nematicides such as methyl bromide and 1,3-dichloropropene, which kill nematodes by slowly diffusing through the soil, are phytotoxic and must be applied well before planting. Environmental concerns, primarily groundwater contamination, ozone depletion, and pesticide residues in food (National Research Council, *Pesticides in the Diet of Infants and Children* (Washington, D.C.: National Academy of Sciences, 1993) have prompted the removal of Aldicarb, DGBCP, and other toxic nematicides from the market by the Environmental Protection Agency, with methyl bromide to be withdrawn in the U.S. by 2002. Johnson & Bailey, "Pesticide Risk Management and the United States Food Quality Protection Act of 1996," in PESTICIDE CHEMISTRY AND BIOSCIENCE: THE FOOD-ENVIRONMENT CHALLENGE 411-20 (Royal Society of Chemistry, Cambridge, 1999). Physical control measures, such as solarization and hot water treatment, crop rotation and other biological control measures, and integrated approaches have been used to ameliorate the damage caused by plant parasitic nematodes. See, e.g., Whitehead, *Plant Nematode Control*, Wallingford: CAB International (1998). No single method or combination of measures is uniformly effective, however.

Molecular genetic methods, such as gene knockouts, can uncover the biological function of individual genes and proteins in an organism, information that can form the foundation for developing target-based compound discovery screens. At present, however, these techniques are difficult to perform in parasitic nematodes.

In contrast, such procedures can be performed in a straightforward manner in *C. elegans*. Furthermore, the complicated life cycle of many parasitic nematodes and their need for a suitable plant or animal host makes it inconvenient to propagate them in the laboratory.

The genome of *C. elegans* is predicted to contain 284 nuclear receptors (Gissendanner et al., 2004; Sluder and Maina, 2001). Forward and reverse genetic studies have uncovered roles for *C. elegans* receptors in diverse physiological processes, such as dauer formation, reproduction, and life span (DAF-12), larval molting (NHR-23), sex determination (SEX-1), xenobiotic metabolism (NHR-8), neuronal development (UNC-55, ODR-7, FAX-1) and lipid metabolism (NHR-49). Nevertheless, all nuclear receptors in worms remain "orphans," since ligands regulating their function have not been identified (Lindblom et al., 2001; Sluder and Maina, 2001; Van Gilst et al., 2005a; Van Gilst et al., 2005b).

In contrast to other *C. elegans* nuclear receptors, a considerable amount of genetic evidence supports the existence of a steroid-like ligand for the orphan receptor, DAF-12. DAF-12 belongs to a group of over 30 genes, collectively called daf (dauer formation) genes, which transduce environmental signals that influence the choice between alternative developmental programs of dauer diapause or reproductive development (Antebi et al., 2000; Riddle and Albert, 1997).

Dauer diapause is a process in which animals at the second larval stage (L2) delay further reproductive development under conditions of diminishing food or overcrowding and instead form the non-feeding, non-reproductive, and long-lived dauer larva (Riddle and Albert, 1997). Upon entry into a more favorable environment, dauer larvae resume feeding and reproductive growth.

Mutations in Daf genes generally produce a dauer constitutive phenotype (Daf-c) or a dauer defective phenotype (Daf-d). Daf-c mutants always arrest as dauers, while Daf-d mutants bypass dauer, regardless of environmental signals. Loss of daf-12 results in Daf-d as well as L3 stage heterochronic phenotypes, indicating that daf-12 is required for dauer formation and for proper developmental timing in the reproductive state (Antebi et al., 1998; Antebi et al., 2000).

Detailed analysis of the dauer formation genes has revealed that favorable environments activate insulin/IGF-1 and TGFβ signaling pathways within the organism that converge on DAF-12 to inhibit its dauer promoting function and activate its reproductive function (Kimura et al., 1997; Ren et al., 1996; Schackwitz et al., 1996). Acting cell non-autonomously, these pathways are believed to activate, either directly or indirectly, the production of a DAF-12 ligand by the cytochrome P450, DAF-9 (Gerisch et al., 2001; Jia et al., 2002). Evidence for this model stems from the findings that insulin-like receptor (daf-2), TGFβ (daf-7), and cytochrome P450 (daf-9) signaling mutants are Daf-c. Furthermore, epistasis experiments have revealed that they act upstream of daf-12, since Daf-d alleles of daf-12 suppress the Daf-c phenotypes exhibited by these signaling mutants (Larsen et al., 1995). In addition to the Daf-d alleles, Daf-c mutants of daf-12 have been isolated that map to a single residue (R564) in the putative ligand binding domain of DAF-12 and are predicted to perturb ligand binding (Antebi et al., 2000). Phenotypically, these mutants arrest as partial dauers but recover and resemble weak daf-9 alleles that exhibit gonadal migration (Mig) defects (Gerisch et al., 2001; Jia et al., 2002). Thus, the predicted loss of hormone production in daf-9 null worms or loss of hormone binding by daf-12 Daf-c worms results in a failure to inhibit dauer-promoting functions and activate L3 stage reproductive functions of DAF-12.

Several lines of evidence suggest that DAF-12 ligands may be derived from cholesterol. First, *C. elegans* lacks the ability to synthesize cholesterol, which is required exogenously for normal growth and fertility (Chitwood, 1999). Second, cholesterol deprivation produces Mig and Daf-c phenotypes in wild-type worms and enhances the Mig and Daf-c phenotypes of weak daf-9 and daf-12 alleles (Gerisch et al., 2001; Jia et al., 2002; Matyash et al., 2004). Finally, worms lacking both homologs (ncr-1, ncr-2) of the human Niemann-Pick type C1 gene, a membrane glycoprotein implicated in lysosomal transport of cholesterol, arrest constitutively as dauers (Li et al., 2004).

These data indicate that a sterol-derived hormone promotes reproductive development in *C. elegans*. Evidence that lipid extracts from wild-type worms can rescue daf-9 phenotypes has strengthened the hormone hypothesis (Gill et al., 2004). Nevertheless, the identities of DAF-9-derived hormonal ligands that activate DAF-12 have remained elusive.

Accordingly, ligands must be identified that modulate the DAF-9/DAF-12 pathway, thereby to identify new agents that are active against pathogenic and parasitic nematode species, e.g., compounds active against animal or plant parasitic nematodes. A need also exists for new methodologies and screening technologies that allow for the identification of compounds active against nematodes. In particular, screening assays are needed that can be performed conveniently, in a high throughput format.

SUMMARY OF THE INVENTION

The present invention provides a novel approach to controlling nematode growth and infestation, by influencing the biochemical pathways that determine whether nematodes enter, avoid, or recover from an infective larvae stage, illustrated by the dauer stage in *C. elegans*. In particular, antagonist and agonist compounds of certain nuclear receptors in the pathways are contemplated. On the one hand, antagonist compounds can induce dauer formation or, for a parasitic nematode, induce the infective stage, thereby to delay or prevent nematode development and reproduction, pursuant to the invention. On the other hand, agonists can effect avoidance or recovery of the dauer stage, which, according to the invention, can serve to undercut nematode survival, e.g., when an inadequate food supply or other environmental stress otherwise favors a larval state.

An important aspect of the present invention is the inventors' finding that the cytochrome P450 enzyme, DAF-9, metabolizes 3-keto steroids into 3-keto steroidal acids, which then bind the intracellular nuclear receptor, DAF-12, to disfavor entry into the dauer stage or allow recovery from the dauer stage. By the same token, the present invention contemplates related synthetic compounds, compositions, and methodology for controlling nematode growth and treating nematode infestation. The invention further encompasses procedures and assays for identifying compounds that modulate the activity of DAF-9 and DAF-12, along with their homologous receptors in parasitic nematodes.

BRIEF DESCRIPTION OF THE DRAWINGS

The figures relate the following abbreviation: chenodeoxycholic acid (CDCA), cholic acid (CA), deoxycholic (DCA) acid, lithocholic acid (LCA), 3-keto-lithocholic acid (3K-LCA), 6-keto-lithocholic acid (6K-LCA), 7-keto-lithocholic acid (7K-LCA). Reporter gene activity is expressed as fold induction of relative light units (RLU) compared to ethanol control (n=3±SD).

FIG. 1 (B and C) shows activation of DAF-12 by 10 μM bile acids (B) or *C. elegans* sterols (C) and their 3-keto derivatives in the presence of DAF-9 (black bars) or in its absence (white bars). In (B) co-transfection of the intestinal bile acid transporter (IBAT) expression plasmid was used to facilitate bile acid uptake.

FIG. 1 (D) shows rescue of daf-9(dh6) null worms by sterols after incubation with DAF-9 microsomes. Results are reported as percentage of animals rescued from dauer as wildtype gravid adults (WT), Mig adults, or molt-defective larvae. Numbers in each bar refer to worms tested.

FIG. 1 (E) shows dose response of DAF-12 activation to indicated sterols in cells co-transfected with DAF-9.

FIGS. 2 (C-F) HPLC fractions from 10 pooled DAF-9 microsomes incubated with 4-cholesten-3-one or lathosterone were tested for GAL4-DAF-12 activity in the absence of DAF-9 (C and D), or for rescue of daf-9 null phenotypes (E and F). Fractions correspond to 1 min intervals of retention times in (A and B). Transfections and rescue assays are described in FIG. 1 legend. Average number of worms tested in (E) and (F) were 75 and 125, respectively.

FIGS. 2 (G and H) shows mass spectra of DAF-9 metabolites of 4-cholesten-3-one (peaks 1-2) and lathosterone (peaks 3-4) scanned from m/z 250-500.

FIG. 3 (B) shows DAF-9 independent activation of GAL4-DAF-12 in HEK293 cells after incubation with the indicated sterols (10 μM for all sterols except 22(R)-hydroxy-4-cholesten-3-one, which was 4 μM).

FIG. 3 (C) shows UV chromatogram of 4-cholesten-3-one oxysterols (top panel) compared to DAF-9 (upper line) or control (lower line) microsomes incubated with 100 μM 4-cholesten-3-one (bottom panel). Arrows indicate co-eluting sterols. The carboxylic acid and alcohol metabolites of DAF-9 are indicated.

FIG. 3 (D) shows UV chromatogram of DAF-9 (upper line) and control (lower line) microsomes after incubation with 100 μM (25R),26-hydroxy-4-cholesten-3-one (top panel) or (25S),26-hydroxy-4-cholesten-3-one (bottom panel). Arrows indicate products unique to DAF-9 microsomes. Mass spectra of DAF-9 metabolites (insets) were obtained in positive ion scan mode.

FIG. 3 (E) Microsome reactions from (D) were diluted 8-fold and tested for daf-9 rescue as in FIG. 1D. Numbers indicate worms included in each experiment.

FIG. 4 (B) shows dose response of GAL4-DAF-12 activation to 4-cholesten-3-one metabolites in HEK293 cells.

FIG. 4 (C) shows DIC microscopy of daf-9(dh6) (a-f) and daf-9(rh50) (g-h) mutants treated with or without 250 nM (25S),26-3-keto-4-cholestenoic acid. (a) Rescued adult, (b) partial dauer, (c) head of rescued L3 larva, (d) head of partial dauer, (e) cuticle of rescued L3 larva, (f) dauer alae, (g) reflexed gonad of L3 larva, (h) unreflexed gonad of L3 larva.

FIG. 4 (D) shows response of daf-9(dh6) nulls treated with (25S),26-3-keto-4-cholestenoic acid or (25R),26-3-keto-4-cholestenoic acid. Results are expressed as percentage of worms rescued from dauer after 3 days at 20° C. Worms were scored as adults or molt-defective larvae.

FIG. 4 (E) shows rescue of daf-9(rh50), daf-12(rh61), and daf-12(rh273) Mig phenotypes by (25S),26-3-keto-4-cholestenoic acid. Results are expressed as percentage of reflexed gonadal arms scored after 3 days at 20° C. (n>60 from 2 experiments).

FIG. 4 (F) shows rescue of daf-9(dh6), daf-2(e1368), daf-7(m62), ncr-1 (nr2023)ncr-2(nr2022), daf-12 (rh273), and daf-2 (e1370) mutants by (25S),26-3-keto-4-cholestenoic acid. Also shown by different shading are the percentage of dauer-rescued worms that exhibited wild-type adult (black bar) or Mig (striped bar) gonads, or an arrested L3 phenotype (white bar). Dauer rescue was scored after 2 days at 25° C. for daf-2 and daf-7, or 3 days at 20° C. for daf-9, daf-12 and ncr-1;ncr-2 (n>200 from 2 independent experiments).

FIG. 5 (A) shows ligand-dependent interaction of DAF12 with DIN-1S by mammalian two-hybrid analysis in HEK293 cells co-transfected with GAL4-DIN-1S and VP16-DAF-12 or VP16-DAF-12 R564C.

FIG. 5 (B) shows effect of DIN-1S on basal activation of GAL4-DAF-12 in HEK293 cells with or without 100 nM (25S),26-3-keto-4-cholestenoic acid. Cells were transfected with 45 ng/well DIN-1S and 15 ng/well GAL4-DAF-12.

FIG. 5 (C) shows mammalian two-hybrid assay in HEK293 cells co-transfected with GAL4-SRC-1-interaction domain 4 (ID4) and VP16-DAF-12 or VP16-DAF-12 R564C.

FIG. 5 (D) shows dose responsive activation of a luciferase reporter containing the Lit-1 kinase genomic regulatory region by full-length DAF-12 and (25S),26-3-keto-4-cholestenoic acid in HEK293 cells.

FIG. 6 (D) shows structures of DAF-12 ligands.

FIG. 7 (B) shows GAL4-DAF-12 activation in HEK293 cells in the presence of fractionated lipid extracts.

FIG. 7 (C) shows GAL4-DAF-12 activation in HEK293 cells by silica fractions of lipids eluted with acetone:methanol.

FIG. 7 (D) shows LC/MS analysis of pooled and re-purified fractions 57-64 in negative selective ion monitoring mode (m/z 413) compared with DAF-9 metabolites of 4-cholesten-3-one.

Standards for (25R),26-3-keto-4-cholestenoic acid (upper panel) and (25S),26-3-keto-4-cholestenoic acid (lower panel) are shown. Insets show mass spectra obtained in both positive (left) and negative (right) ion mode.

FIG. 10. Expression plasmids for GAL4-DAF-12, GAL4-DAF-12-R564C, GAL4-DAF-12-R564H, and a panel of vertebrate and invertebrate GAL4-nuclear receptors were tested for activation by 5 μM (25S),26-3-keto-4-cholestenoic acid in HEK293 cells. Results for each condition were obtained from triplicate assay (±SD) and are expressed as fold induction relative to ethanol vehicle. RLU, relative light units.

FIGS. 11A and 11B. Chemical structures, names, and $^1$H-NMR (400 MHz) data for compounds disclosed herein.

Figure 12:
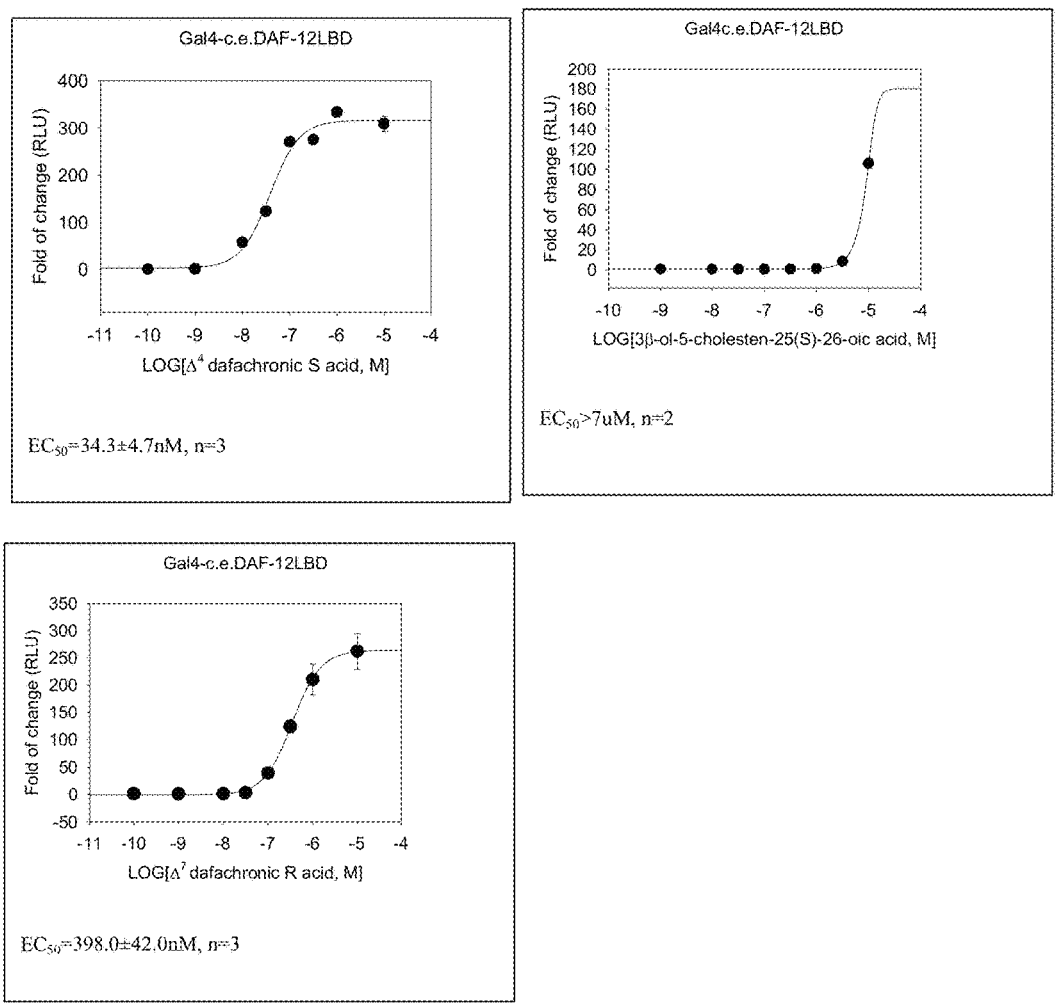

FIG. 12. Transactivation of *C. elegans* nuclear hormone receptor DAF-12 by (25S),26-3-keto-4-cholestenoic acid ($\Delta^4$ dafachronic S acid), 3-keto-7,(5a)-cholesten-25(R)-26-oic acid ($\Delta^7$ dafachronic R acid), and 3β-ol-5-cholesten-25(S)-26-oic acid.

Figure 13:
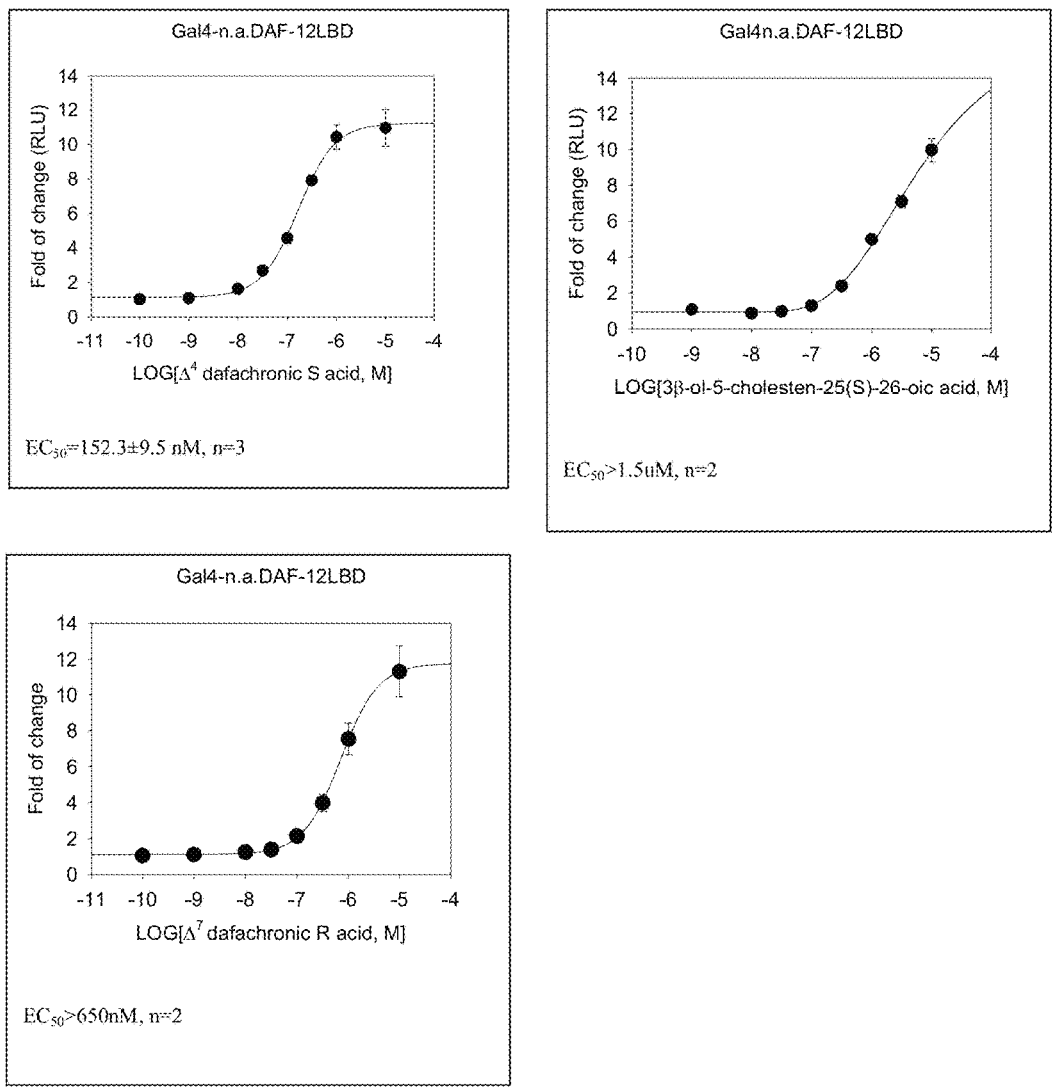

FIG. 13. Transactivation of human hookworm *N. americanus* nuclear hormone receptor DAF-12 by (25S),26-3-keto-4-cholestenoic acid ($\Delta^4$ dafachronic S acid), 3-keto-7,(5a)-cholesten-25(R)-26-oic acid ($\Delta^7$ dafachronic R acid), and 3β-ol-5-cholesten-25(S)-26-oic acid.

Figure 14:
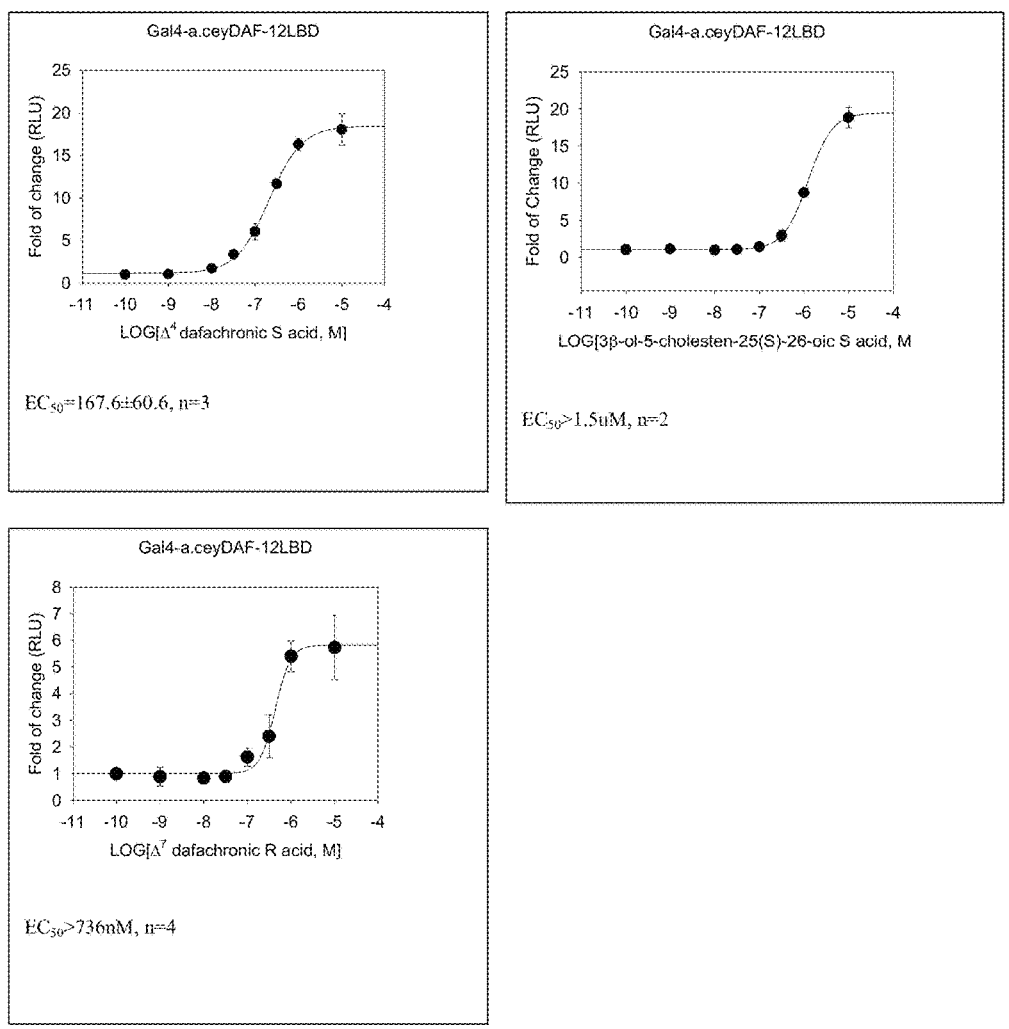

FIG. 14. Transactivation of human/hamster hookworm *A. ceyelanicum* nuclear hormone receptor DAF-12 by (25S),26-3-keto-4-cholestenoic acid ($\Delta^4$ dafachronic S acid), 3-keto-7,(5a)-cholesten-25(R)-26-oic acid ($\Delta^7$ dafachronic R acid), and 3β-ol-5-cholesten-25(S)-26-oic acid.

Figure 15:
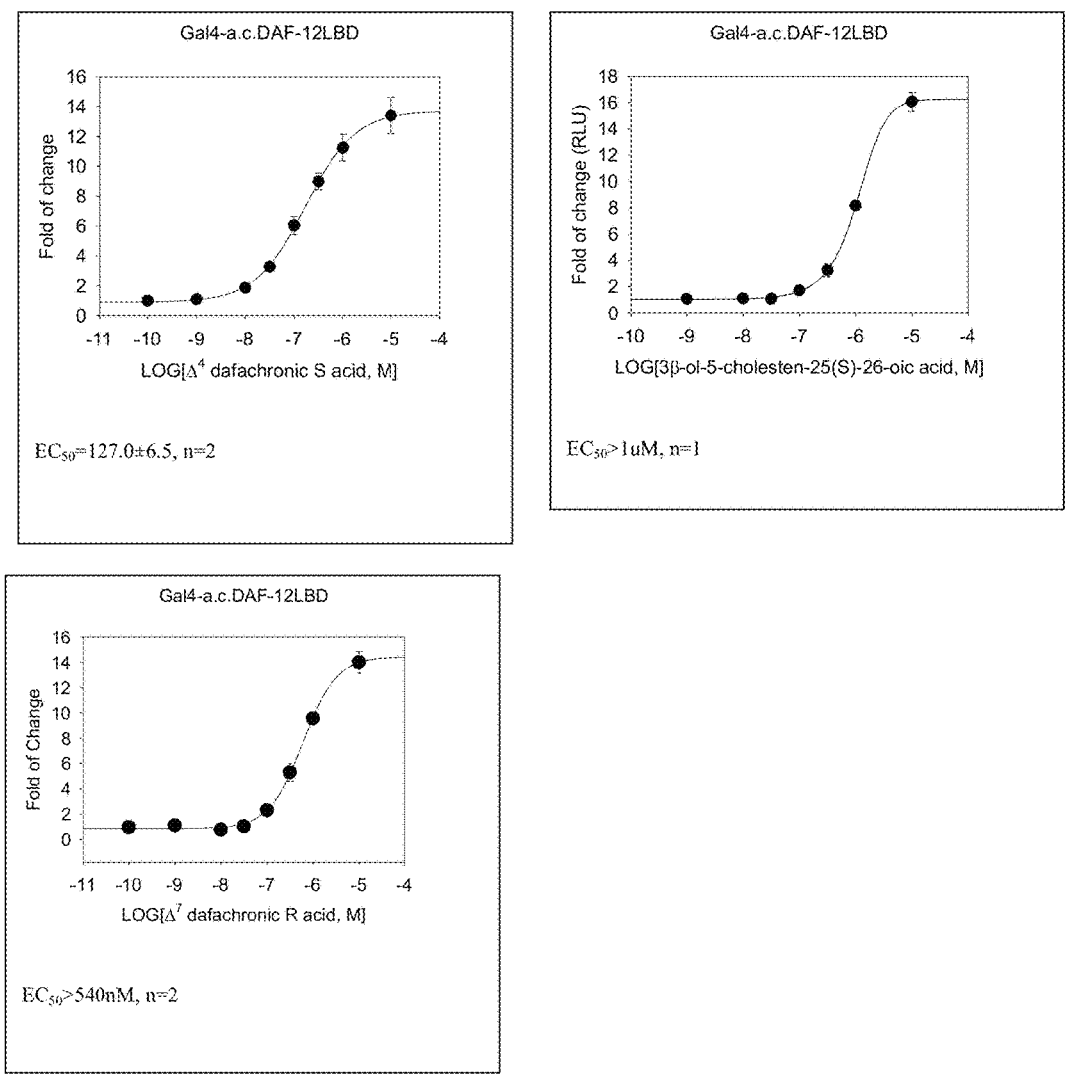

FIG. 15. Transactivation of dog hookworm *A. caninum* nuclear hormone receptor DAF-12 by (25S),26-3-keto-4-cholestenoic acid ($\Delta^4$ dafachronic S acid), 3-keto-7,(5a)-cholesten-25(R)-26-oic acid ($\Delta^7$ dafachronic R acid), and 3β-ol-5-cholesten-25(S)-26-oic acid.

DETAILED DESCRIPTION

Throughout this application, the text refers to various embodiments of the inventive compounds, compositions, and methodology. The various embodiments described are representative examples and should not be construed as descriptions of alternative species. Rather, the descriptions provided here may be of overlapping scope. The embodiments discussed are illustrative only and are not meant to limit the scope of the present invention.

Definitions

Unless indicated otherwise, the terms and phrases used in this description have the following meanings:

"Alkyl" refers to a straight or branched chain, saturated hydrocarbon having the indicated number of carbon atoms. For example, ($C_1$-$C_6$)alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein throughout.

"Alkenyl" denotes a straight or branched chain unsaturated hydrocarbon having the indicated number of carbon atoms and at least one double bond. Examples of a ($C_2$-$C_8$) alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein throughout.

"Alkynyl" refers to a straight or branched chain unsaturated hydrocarbon having the indicated number of carbon atoms and at least one triple bond. Examples of a ($C_2$-$C_8$) alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein throughout.

The term "aryl" refers to a 6- to 14-membered monocyclic, bicyclic or tricyclic aromatic hydrocarbon ring system. Examples of an aryl group include phenyl and naphthyl. An aryl group can be unsubstituted or optionally substituted with one or more substituents as described herein throughout.

"Cycloalkyl" denotes a 3- to 14-membered saturated or unsaturated non-aromatic monocyclic, bicyclic or tricyclic hydrocarbon ring system. Included in this class are cycloalkyl groups which are fused to a benzene ring. Representative cycloalkyl groups include but are not limited to cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocycloheptene, dodecahydroheptalene, decahydroheptalene, octahydroheptalene, hexahydroheptalene, and tetrahydroheptalene. A cycloalkyl group can be unsubstituted or optionally substituted with one or more substituents as described herein throughout.

"Halo" denotes —F, —Cl, —Br or —I.

"Haloalkyl" refers to a $C_1$-$C_6$ alkyl group wherein from one or more of the $C_1$-$C_6$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroaryl" refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl and oxazolyl. A heteroaryl group can be unsubstituted or optionally substituted with one or more substituents as described throughout.

"Heteroatom" is inclusive of oxygen (O), nitrogen (N), and sulfur (S).

The term "heterocycle" refers to 3- to 14-membered ring systems that are either saturated, unsaturated, or aromatic, and that contains from 1 to 4 heteroatoms independently selected from nitrogen, oxygen and sulfur, where the nitrogen and sulfur heteroatoms can be optionally oxidized and the nitrogen heteroatom can be optionally quaternized, including monocyclic, bicyclic, and tricyclic ring systems. The bicyclic and tricyclic ring systems may encompass a heterocycle or heteroaryl fused to a benzene ring. The heterocycle can be attached via any heteroatom or carbon atom. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents as described herein throughout.

Unless otherwise stated, the term "heterocycloalkyl," by itself or combined with other terms, represents cyclic versions of "heteroalkyl." Additionally, a heteroatom can occupy the position at which the heterocycle is attached to the remainder of the molecule. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

"Lanost-7-en-26-oic acid" refers to a compound represented by following structure:

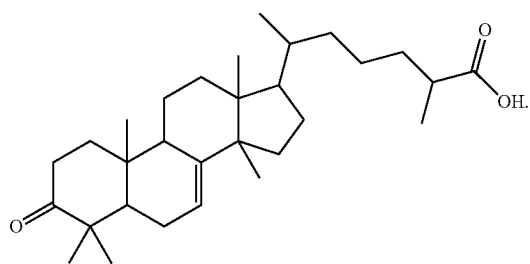 [SMILES: CC(CCCC(C)C1CCC2(C)C3=CCC4C(C)(C)C(=O)CCC4(C)C3CCC12C)C(=O)O]

"Oxo" refers to the oxygen atom (O=).
"Carbonyl" refers to the group (O=C).
"Thione" refers to the sulfur atom (S=).
"Thiocarbonyl" refer to the group (S=C).

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. In some embodiments, a stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, the depicted structure controls. If the stereochemistry of a structure or a portion of a structure is not indicated with, for example, bold, wedged, or dashed lines, then the structure or portion of the structure is to be interpreted as encompassing all stereoisomers of it.

"Solvate" is a form of a compound of formula I, where solvent molecules are combined in a definite ratio as an integral part of the crystal structure of the compound.

Depending on the structure of its referent, the phrase "pharmaceutically acceptable salt" denotes a pharmaceutically acceptable organic or inorganic acid or base salt of a compound of formula I. Representative pharmaceutically acceptable salts include, e.g., alkali metal salts, alkali earth salts, ammonium salts, water-soluble and water-insoluble salts, such as the acetate, amsonate (4,4-diaminostilbene-2, 2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. Furthermore, a pharmaceutically acceptable salt can have more than one charged atom in its structure. In this instance the pharmaceutically acceptable salt can have multiple counterions. Accordingly, a pharmaceutically acceptable salt can have one or more charged atoms and/or one or more counterions.

"Synthetic compound" refers to a compound that is prepared by chemical synthesis or is prepared by and then isolated from cell culture. In either case, the compound is "purified," in that it is in a form that is at least free of cellular debris and, preferably, is sufficiently free of contaminants to be suitable for pharmacological use, as described here.

Accordingly, the present invention provides a synthetic compound according to formula I or a stereoisomer, solvate, or pharmaceutically acceptable salt thereof:

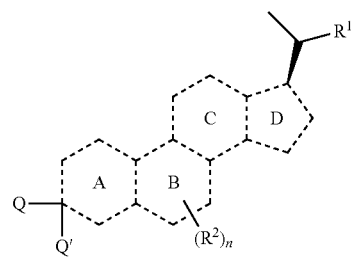

I wherein one of Q or Q' is OH or SH and the other of Q or Q' is hydrogen, or Q and Q' together with the carbon atom to which they are attached form a carbonyl or thiocarbonyl group.

$R^1$ is selected from the group consisting of:

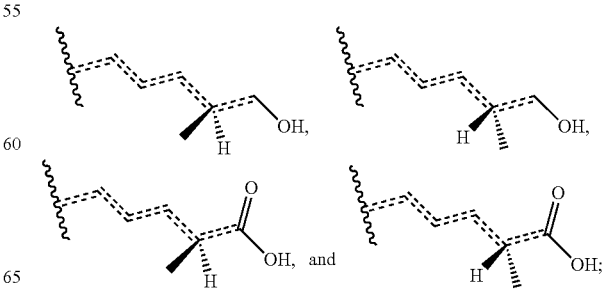

wherein each instance of ≡ independently is a single bond, a double bond, or a triple bond; and wherein $R^1$ is optionally substituted with 1 to 8 substituents, each of which is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', OR, and SR.

$R^2$ is a substituent on one or more carbon atoms in rings A, B, C, and D and, in each instance, is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', oxo, thione, OR, and SR.

R and R' are independently selected from the group consisting of hydrogen, $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl.

Variable n is selected from the group consisting of 0, 1, 2, 3, 4, 5, 6, 7, 8, 9, and 10.

Each instance of ---- independently is a single bond or a double bond; wherein one of ---- is optionally absent so that one of rings A, B, C or D is no longer a cyclic ring or part of a cyclic ring, and wherein when ---- is absent, the two resultant terminal carbon atoms are substituted with one or more hydrogen atoms to satisfy the carbon atom valencies.

It should be understood that formula I does not include (25R)-26-hydroxy-4-cholesten-3-one or lanost-7-en-26-oic acid.

In some embodiments, Q and Q' together with the carbon atom to which they are attached form a carbonyl or thiocarbonyl group.

In some embodiments, $R^1$ is selected from the group consisting of:

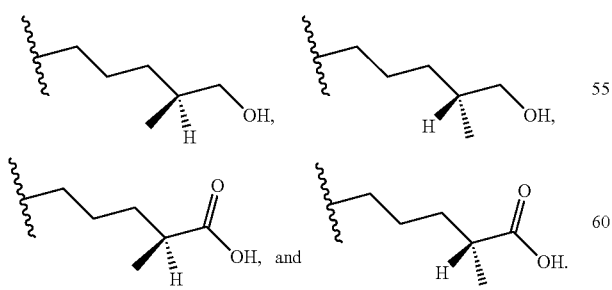

In some embodiments, the invention provides a compound of formula I wherein at least one ---- is a double bond. In some aspects, the compounds have formulae Ia-1 g:

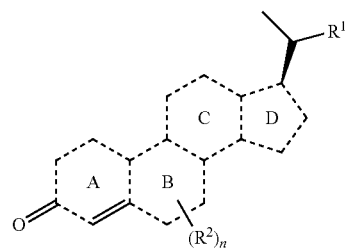
Ia

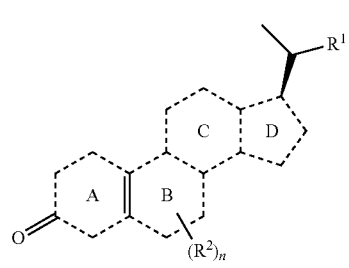
Ib

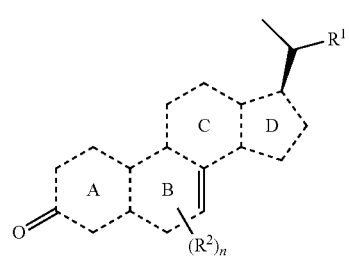
Ic

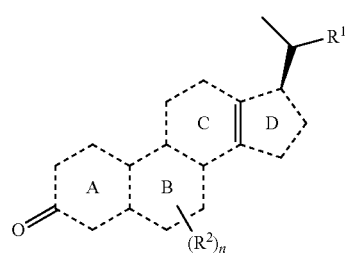
Id

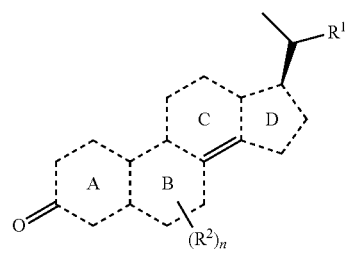
Ie

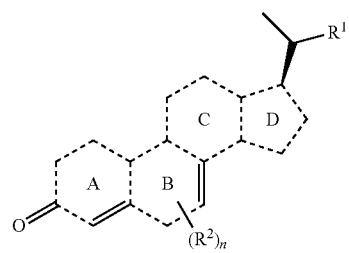
If

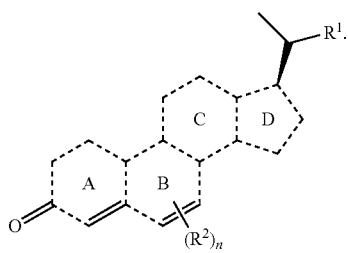

Ig

In other embodiments, the invention provides a compound of formula I, wherein $R^2$ is selected from the group consisting of halo, $(C_1-C_8)$alkyl, and $(C_1-C_8)$haloalkyl. In some aspects, $R^2$ is fluoro, methyl, or trifluoromethyl.

In still other embodiments, the invention provides a compound having the formula:

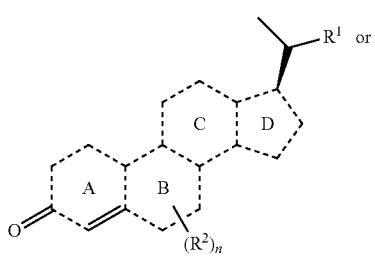

Ia

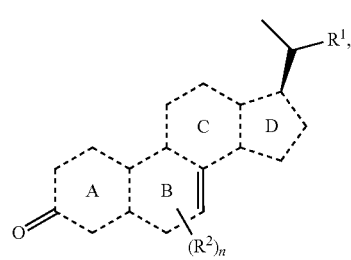

Ic wherein $R^2$ is selected from the group consisting of fluoro, methyl, and trifluoromethyl. In some aspects $R^2$ is methyl.

In another embodiment, n is 2. In some such aspects $R^2$ is methyl.

In some embodiments, the invention provides a compound of formula I or I' having formulas Ia', Ic', Ie', If, and Ig':

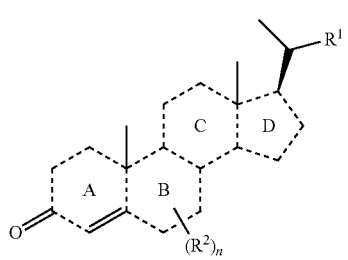

Ia'

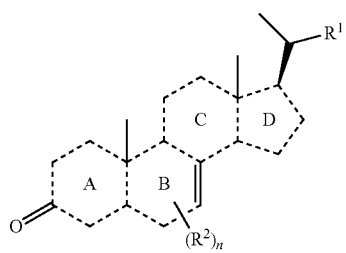

Ic'

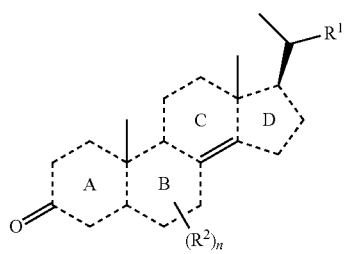

Ie'

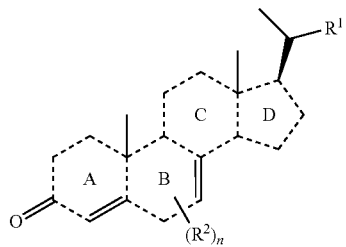

If'

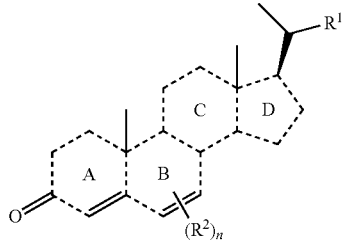

Ig' wherein $R^1$, $R^2$, and n are as defined for formula I.

In some embodiments, the invention provides a compound having the structure:

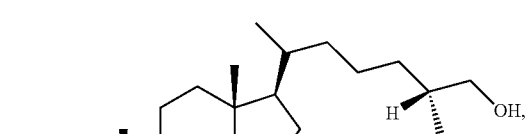

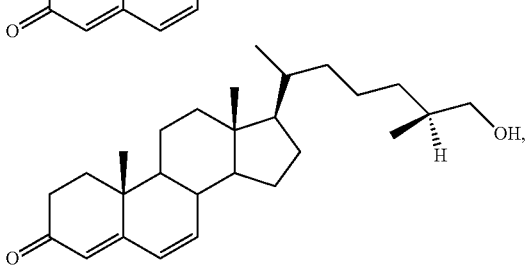

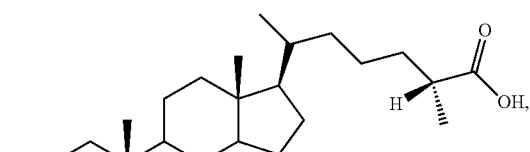
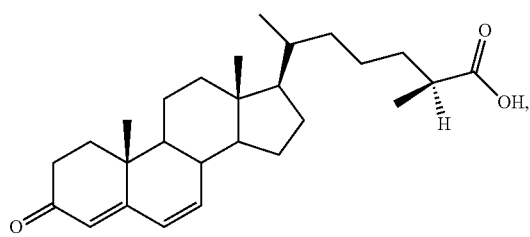
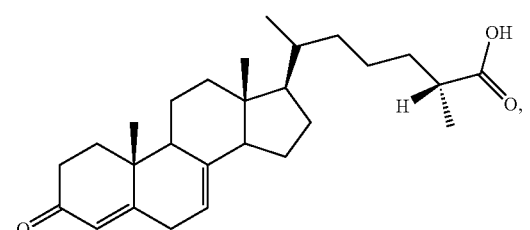
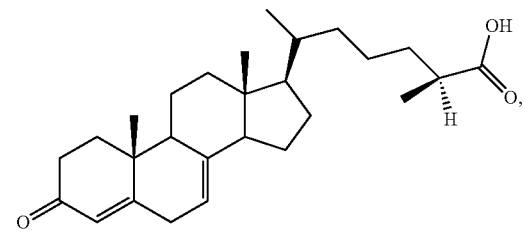
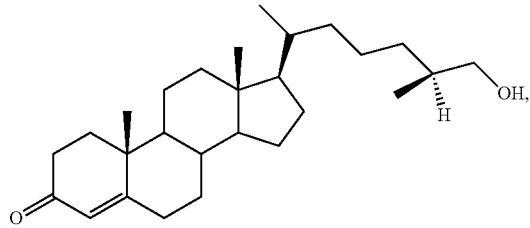
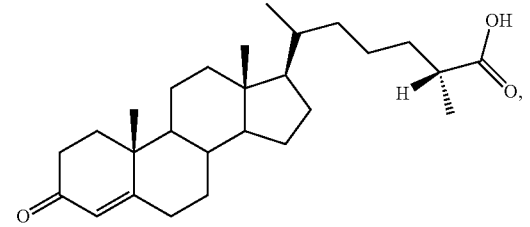
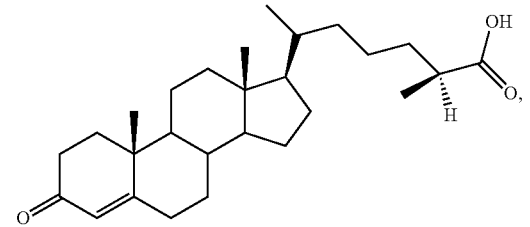
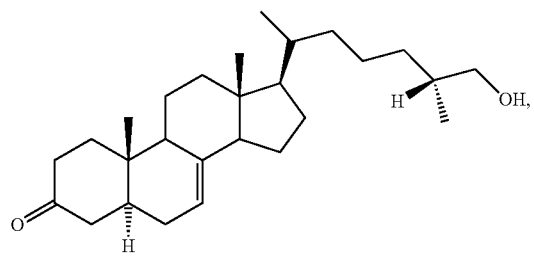
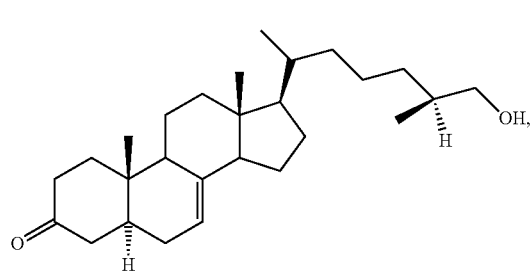
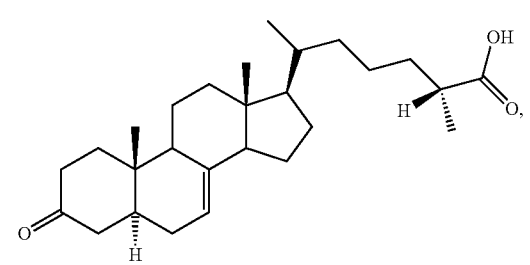
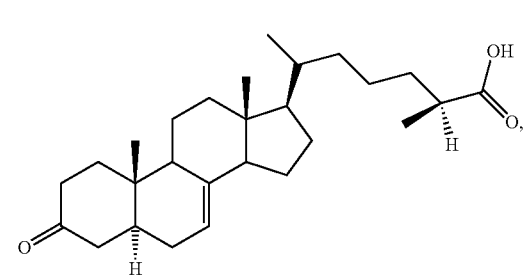
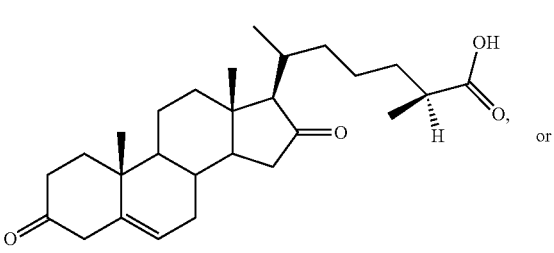
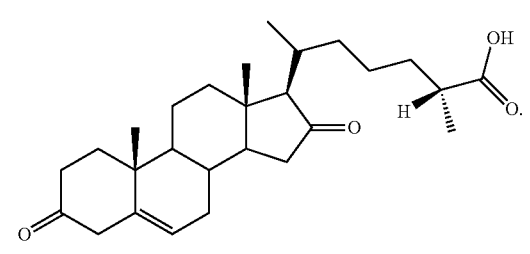 [SMILES: CC(CCC[C@@H](C)C(=O)O)[C@H]1C(=O)CC2C3CC=C4CC(=O)CC[C@]4(C)C3CC[C@@]21C]
In certain embodiments, the invention provides a compound having the structure

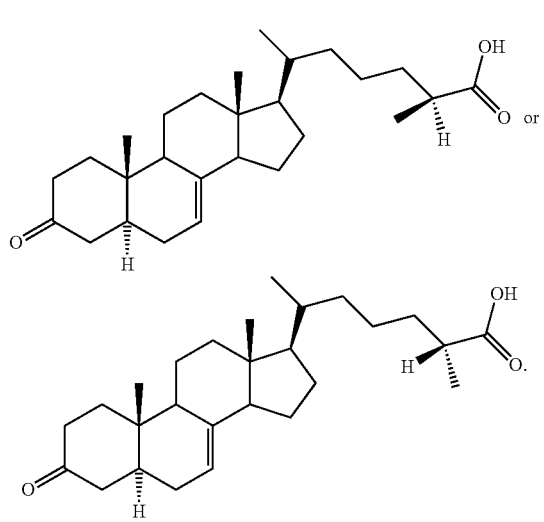

In accordance with another aspect of the invention, a method is provided for controlling the growth of a nematode by contacting it with a biologically effective amount of at least one compound of formula I or a stereoisomer, solvate, or pharmaceutically acceptable salt thereof:

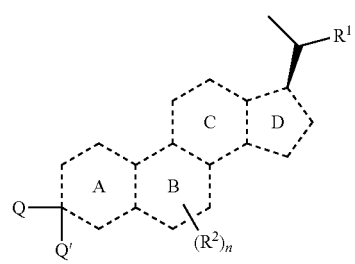

I wherein one of Q or Q' is OH or SH and the other of Q or Q' is hydrogen, or Q and Q' together with the carbon atom to which they are attached form a carbonyl or thiocarbonyl group;

$R^1$ is selected from the group consisting of:

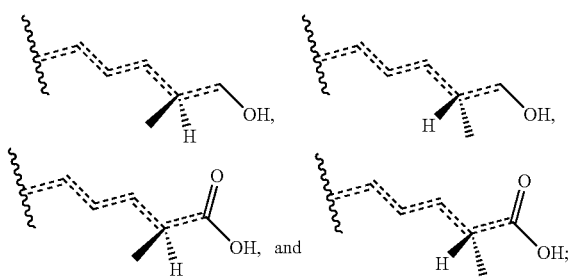

wherein each instance of ⁝⁝⁝ independently is a single bond, a double bond, or a triple bond; and wherein $R^1$ is optionally substituted with 1 to 8 substituents, each of which is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', OR, and SR.

$R^2$ is a substituent on one or more carbon atoms in rings A, B, C, and D and, in each instance, is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', oxo, thione, OR, and SR.

R and R' are independently selected from the group consisting of hydrogen, $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl.

Variable n is selected from the group consisting of 0, 1, 2, 3, 4, 5, 6, 7, 8, 9, and 10.

Each instance of ---- independently is a single bond or a double bond; wherein one of ---- is optionally absent so that one of rings A, B, C or D is no longer a cyclic ring or part of a cyclic ring, and wherein when ---- is absent, the two resultant terminal carbon atoms are substituted with one or more hydrogen atoms to satisfy the carbon atom valencies.

Specific compounds for controlling nematode growth include:

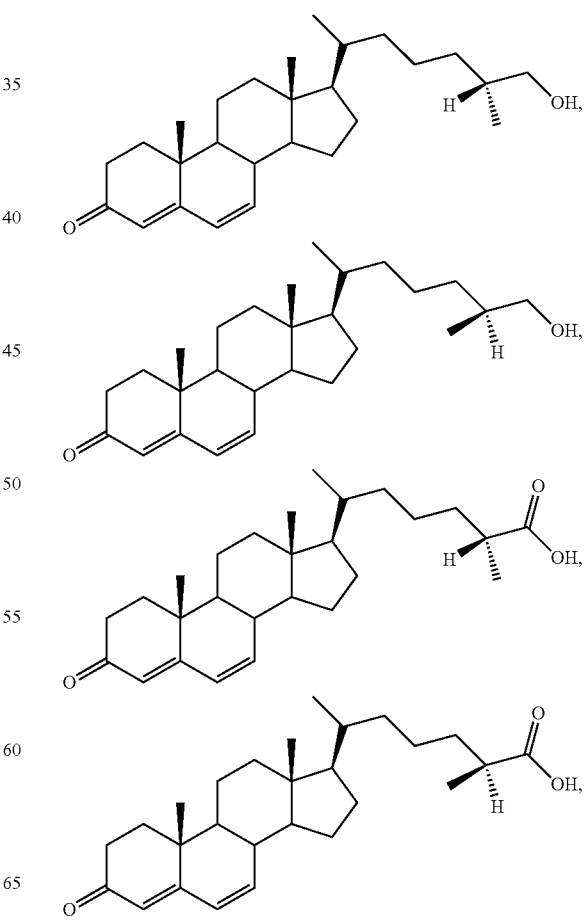

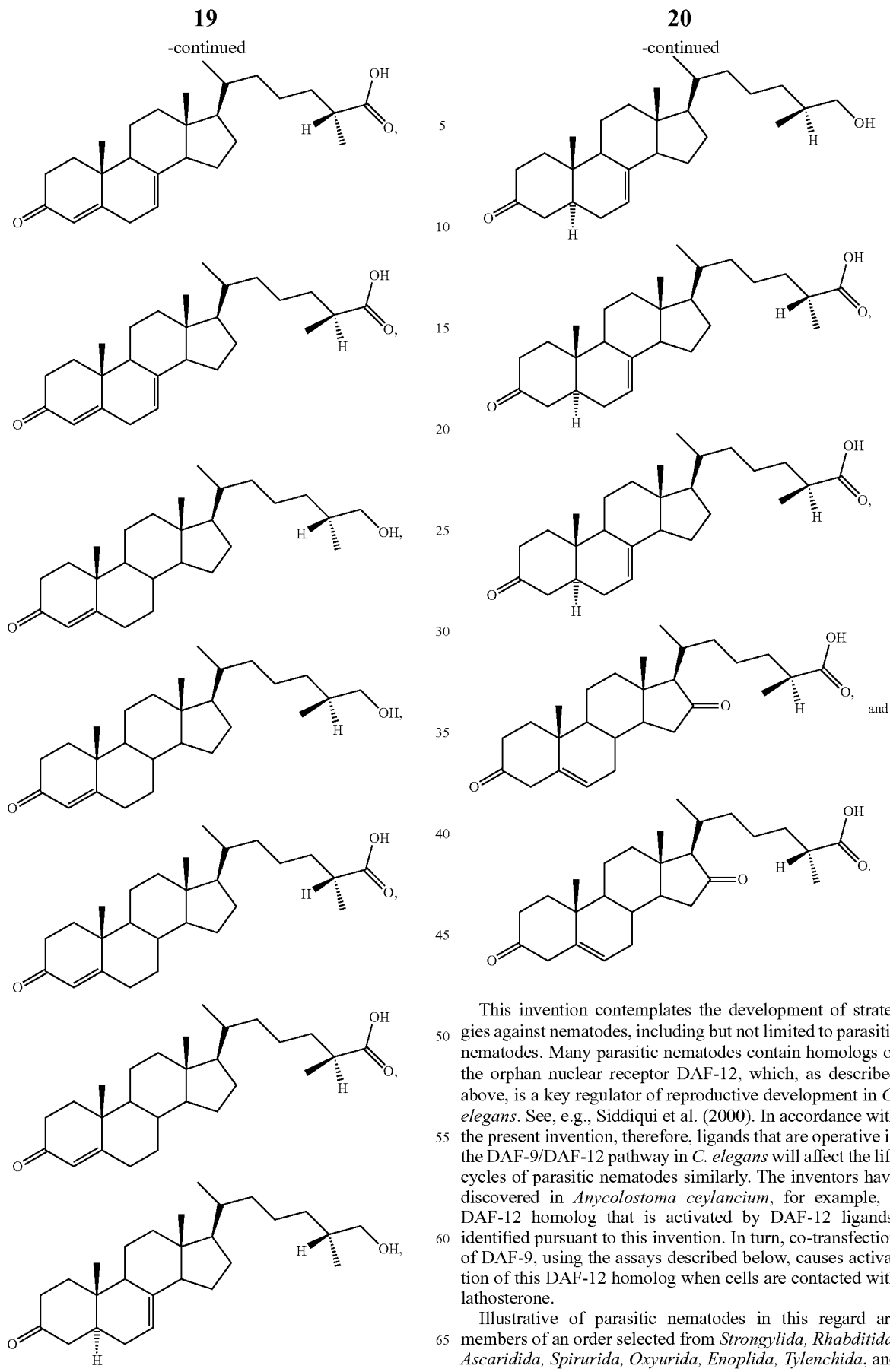

This invention contemplates the development of strategies against nematodes, including but not limited to parasitic nematodes. Many parasitic nematodes contain homologs of the orphan nuclear receptor DAF-12, which, as described above, is a key regulator of reproductive development in *C. elegans*. See, e.g., Siddiqui et al. (2000). In accordance with the present invention, therefore, ligands that are operative in the DAF-9/DAF-12 pathway in *C. elegans* will affect the life cycles of parasitic nematodes similarly. The inventors have discovered in *Anycolostoma ceylancium*, for example, a DAF-12 homolog that is activated by DAF-12 ligands, identified pursuant to this invention. In turn, co-transfection of DAF-9, using the assays described below, causes activation of this DAF-12 homolog when cells are contacted with lathosterone.

Illustrative of parasitic nematodes in this regard are members of an order selected from *Strongylida, Rhabditida, Ascaridida, Spirurida, Oxyurida, Enoplida, Tylenchida*, and *Dorylaimida* nematode orders. Other examples of parasitic nematode include members of a genus selected from *Haemonchus, Oestertagia, Trichostrongylus, Cooperia, Dictyocaulus, Strongylus, Oesophagostomum, Syngamus, Nematodirus, Heligmosomoides, Nippostrongylus, Metastrongylus, Angiostrongylus, Acyclostoma, Necator, Uncinaria, Bunostomum, Strongyloides, Steinernema, Ascaris, Parascaris, Toxocara, Toxascaris, Baylisascaris, Anisakis, Pseudoterranova, Heterakis, Wuchereria, Brugia, Onchocerca, Dirofilaria, Loa, Thelazia, Dracunculus, Gnathostoma, Enterobius, Oxyuris, Syphacia, Trichinella, Trichuris, Capillaria, Globodera, Heterodera, Meloidogyne, Anguina, Ditylenchus, Hirschmanniella, Naccobus, Pratylenchus, Radopholus, Criconema, Tylenchulus, Paratylenchus, Aphelenchus, Bursaphelenchus, Longidorus, Xiphinema, Trichodorus*, and *Paratrichodorus*. Specific parasites include *Strongyloides Stercoralis* and *Acycolostoma ceylanicum*.

In another embodiment, the invention provides a method for reducing or preventing nematode infestation of a plant that is infested or susceptible to infestation by a nematode population, comprising administering to the plant a biologically effective amount of at least one compound according to formula I or a stereoisomer, solvate, or pharmaceutically acceptable salt thereof:

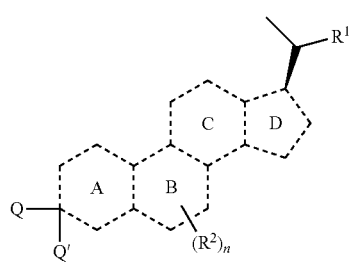

I wherein one of Q or Q' is OH or SH and the other of Q or Q' is hydrogen, or Q and Q' together with the carbon atom to which they are attached form a carbonyl or thiocarbonyl group.

$R^1$ is selected from the group consisting of:

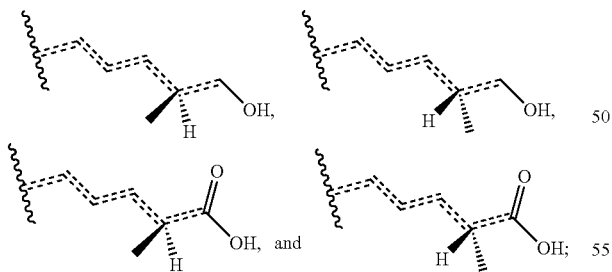

wherein each instance of ⁃⁃⁃ independently is a single bond, a double bond, or a triple bond; and wherein $R^1$ is optionally substituted with 1 to 8 substituents, each of which is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', OR, and SR.

$R^2$ is a substituent on one or more carbon atoms in rings A, B, C, and D and, in each instance, is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', oxo, thione, OR, and SR.

$R^2$ is a substituent on one or more carbon atoms in rings A, B, C, and D and, in each instance, is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', oxo, thione, OR, and SR.

R and R' are independently selected from the group consisting of hydrogen, $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl.

Variable n is selected from the group consisting of 0, 1, 2, 3, 4, 5, 6, 7, 8, 9, and 10.

Each instance of ⁃⁃⁃ independently is a single bond or a double bond; wherein one of ⁃⁃⁃ is optionally absent so that one of rings A, B, C or D is no longer a cyclic ring or part of a cyclic ring, and wherein when ⁃⁃⁃ is absent, the two resultant terminal carbon atoms are substituted with one or more hydrogen atoms to satisfy the carbon atom valencies.

In some aspects of the inventive method, administering comprises treating with the compound, soil in which the plant is grown. In other aspects, the administering comprises treating, with the compound, a seed from which the plant is to be grown.

In another embodiment, the invention provides a method of reducing or preventing a nematode infestation in a mammal, comprising administering to the mammal a therapeutically effective amount of at least one compound according to formula I or a stereoisomer, solvate, or pharmaceutically acceptable salt thereof:

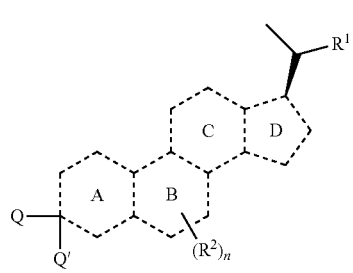

I wherein one of Q or Q' is OH or SH and the other of Q or Q' is hydrogen, or Q and Q' together with the carbon atom to which they are attached form a carbonyl or thiocarbonyl group;

$R^1$ is selected from the group consisting of:

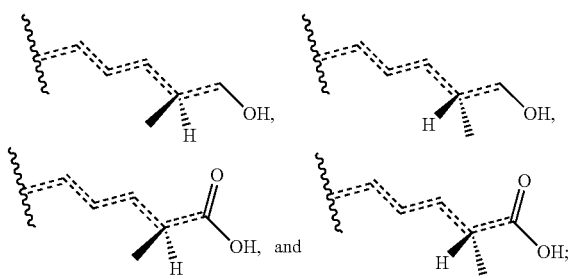

wherein each instance of ≡≡≡ independently is a single bond, a double bond, or a triple bond; and wherein $R^1$ is optionally substituted with 1 to 8 substituents, each of which is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', OR, and SR.

$R^2$ is a substituent on one or more carbon atoms in rings A, B, C, and D and, in each instance, is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', oxo, thione, OR, and SR.

$R^2$ is a substituent on one or more carbon atoms in rings A, B, C, and D and, in each instance, is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', oxo, thione, OR, and SR.

R and R' are independently selected from the group consisting of hydrogen, $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl.

Variable n is selected from the group consisting of 0, 1, 2, 3, 4, 5, 6, 7, 8, 9, and 10.

Each instance of ---- independently is a single bond or a double bond; wherein one of ---- is optionally absent so that one of rings A, B, C or D is no longer a cyclic ring or part of a cyclic ring, and wherein when ---- is absent, the two resultant terminal carbon atoms are substituted with one or more hydrogen atoms to satisfy the carbon atom valencies.

In another embodiment, the invention provides a pharmaceutical composition comprising a pharmaceutically acceptable carrier and a compound according to formula I or a stereoisomer, solvate, or pharmaceutically acceptable salt thereof:

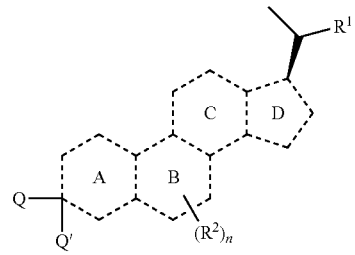

wherein one of Q or Q' is OH or SH and the other of Q or Q' is hydrogen, or Q and Q' together with the carbon atom to which they are attached form a carbonyl or thiocarbonyl group.

$R^1$ is selected from the group consisting of:

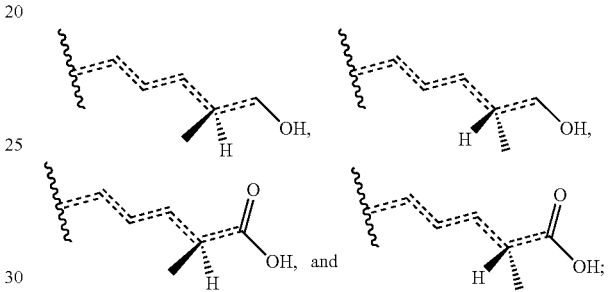

wherein each instance of ≡≡≡ independently is a single bond, a double bond, or a triple bond; and wherein $R^1$ is optionally substituted with 1 to 8 substituents, each of which is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', OR, and SR.

$R^2$ is a substituent on one or more carbon atoms in rings A, B, C, and D and, in each instance, is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', oxo, thione, OR, and SR.

$R^2$ is a substituent on one or more carbon atoms in rings A, B, C, and D and, in each instance, is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', oxo, thione, OR, and SR.

R and R' are independently selected from the group consisting of hydrogen, $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl.

Variable n is selected from the group consisting of 0, 1, 2, 3, 4, 5, 6, 7, 8, 9, and 10.

Each instance of ---- independently is a single bond or a double bond; wherein one of ---- is optionally absent so that one of rings A, B, C or D is no longer a cyclic ring or part of a cyclic ring, and wherein when ---- is absent, the two resultant terminal carbon atoms are substituted with one or more hydrogen atoms to satisfy the carbon atom valencies.

In some embodiments, the composition contains a compound is selected from the group consisting of:

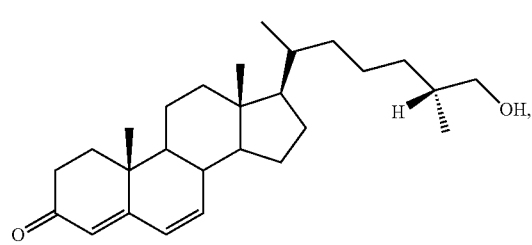

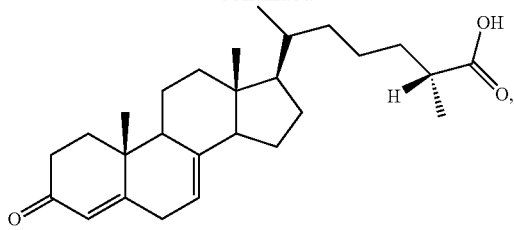

-continued

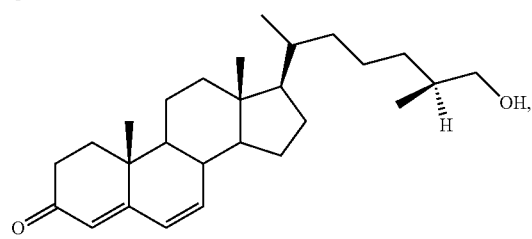

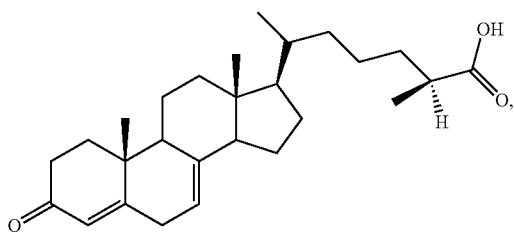

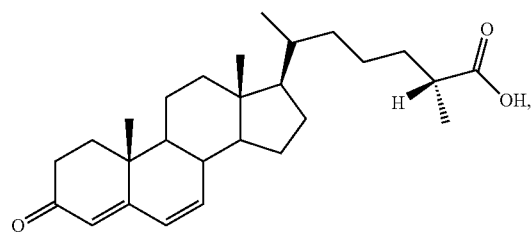

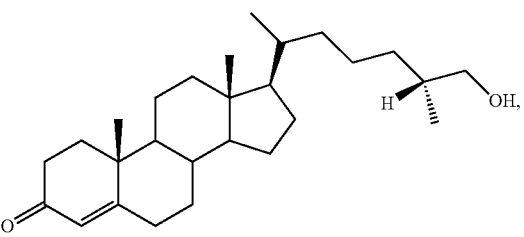

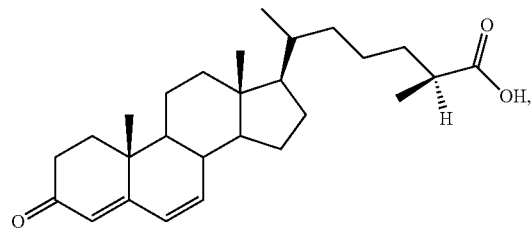

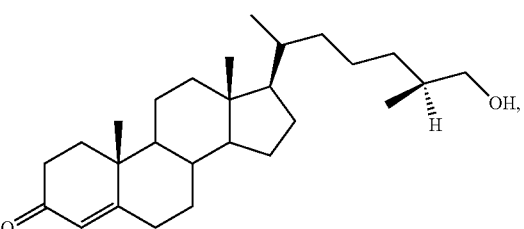

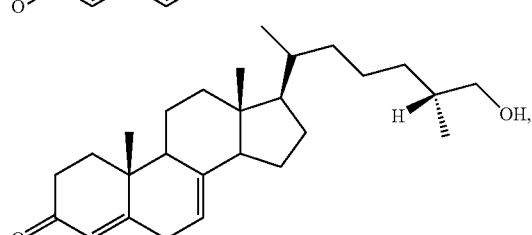

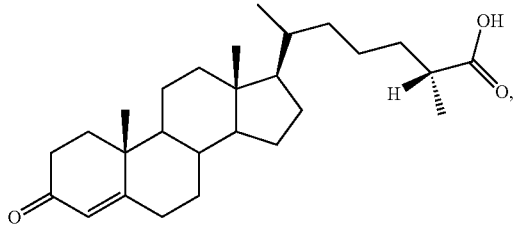

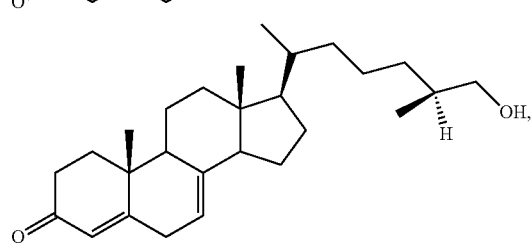

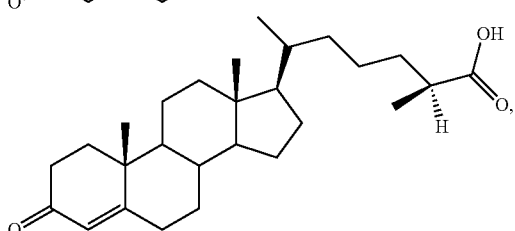

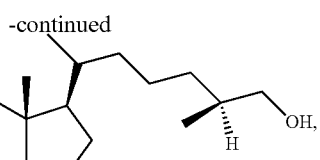

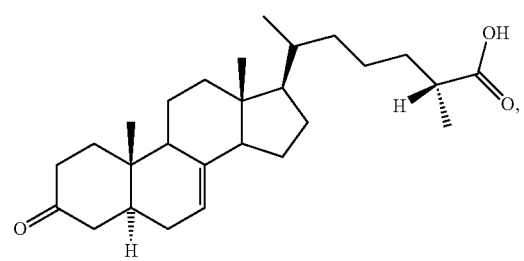

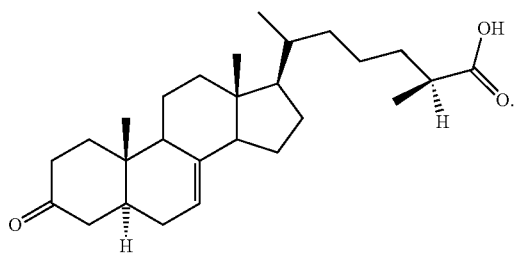

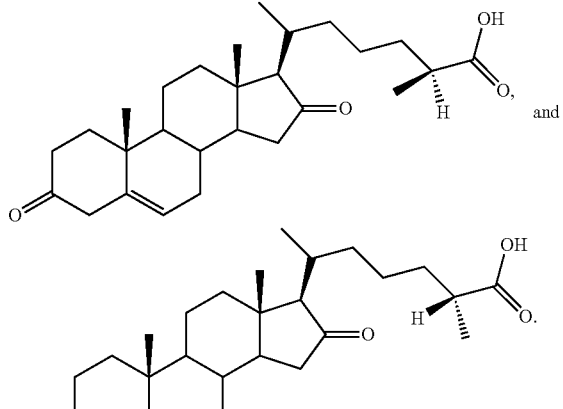

and

In general, the compounds of this invention will be administered in a therapeutically effective amount by any of the accepted modes of administration for agents that serve similar utilities. The actual amount of the compound, as the active ingredient, will depend upon numerous factors, such as the severity of the disease to be treated, the age and relative health of the subject, the potency of the compound used, the route and form of administration, and other factors. The drug can be administered more than once a day, and preferably once or twice a day. All of these factors are within the skill of the attending clinician.

Therapeutically effective amounts of compounds of formula I may range from approximately 0.05 to 50 mg per kilogram body weight of the recipient per day; preferably about 0.1-25 mg/kg/day, more preferably from about 0.5 to 10 mg/kg/day. Thus, for administration to a 70 kg person, the dosage range would most preferably be about 35-70 mg per day. Modes of administration include oral, systemic (e.g., transdermal, intranasal, or suppository), intrathecal, and parenteral (e.g., intramuscular, intravenous, or subcutaneous).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

In general, the compositions of the invention are comprised of a compound of formula I in combination with at least one pharmaceutically acceptable carrier or excipient. Acceptable excipients are nontoxic, aid administration, and do not adversely affect the therapeutic benefit of the compound of formula I. Such excipient may be any solid, liquid, semi-solid or, in the case of an aerosol composition, gaseous excipient that is generally available to the field.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in REMINGTON'S PHARMACEUTICAL SCIENCES, 18$^{th}$ ed. (Mack Publishing Co., 1990).

The amount of the compound in a formulation can vary within the full range employed by those skilled in the art. Typically, the formulation will contain, on a weight percent (wt %) basis, from about 0.01-99.99 wt % of a compound of formula I based on the total formulation, with the balance being one or more suitable pharmaceutical excipients. Preferably, the compound is present at a level of about 1-80 wt %.

In another embodiment the invention provides a culture system for preparing a compound having formula I or a stereoisomer thereof:

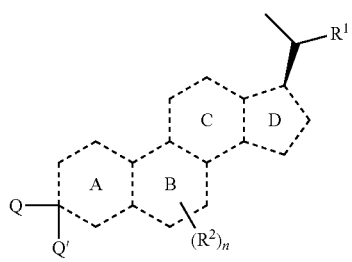

wherein one of Q or Q' is OH or SH and the other of Q or Q' is hydrogen, or Q and Q' together with the carbon atom to which they are attached form a carbonyl or thiocarbonyl group.

$R^1$ is selected from the group consisting of:

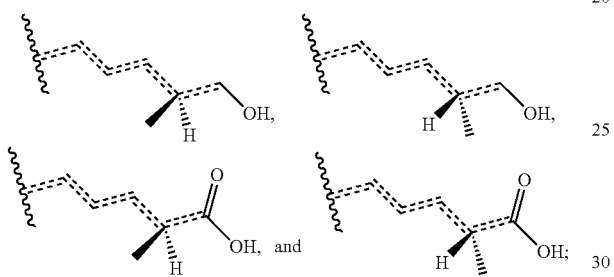

wherein each instance of ≡≡≡ independently is a single bond, a double bond, or a triple bond; and wherein $R^1$ is optionally substituted with 1 to 8 substituents, each of which is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', OR, and SR.

$R^2$ is a substituent on one or more carbon atoms in rings A, B, C, and D and, in each instance, is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', oxo, thione, OR, and SR.

R and R' are independently selected from the group consisting of hydrogen, $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl.

Variable n is selected from the group consisting of 0, 1, 2, 3, 4, 5, 6, 7, 8, 9, and 10.

Each instance of ---- independently is a single bond or a double bond; wherein one of ---- is optionally absent so that one of rings A, B, C or D is no longer a cyclic ring or part of a cyclic ring, and wherein when ---- is absent, the two resultant terminal carbon atoms are substituted with one or more hydrogen atoms to satisfy the carbon atom valencies.

The system comprises cells expressing DAF-9 and media containing a steroid precursor of formula I wherein $R^1$ is:

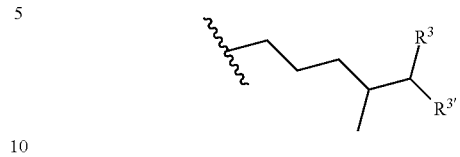

wherein $R^1$ is optionally substituted with 1 to 8 substituents, each of which is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', OR, and SR; and wherein $R^3$ and $R^{3'}$ are independently hydrogen or hydroxy or $R^3$ and $R^{3'}$ together with the carbon atom to they are attached form a carbonyl group.

In some embodiments, the compound produced by the culture is selected from the group consisting of

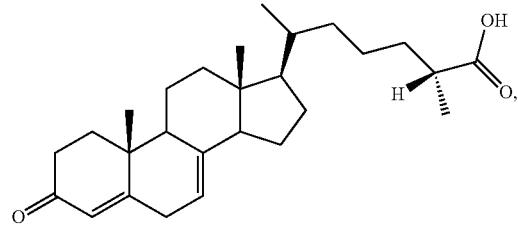

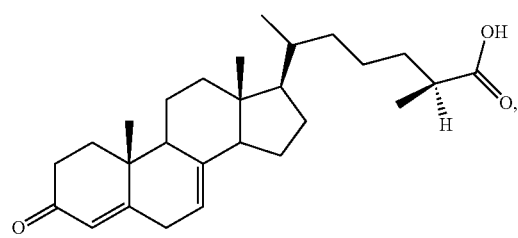

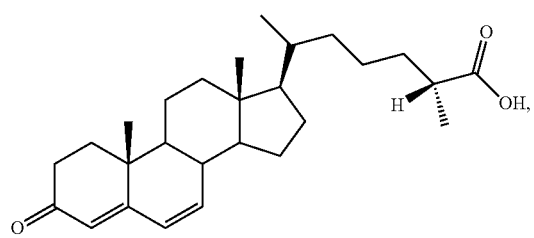

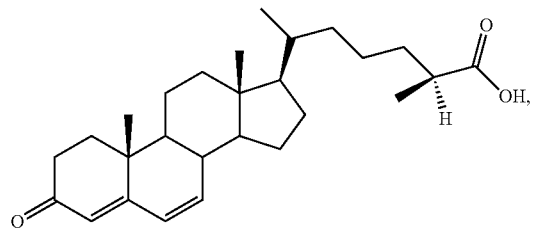

-continued

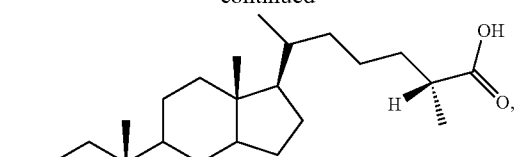

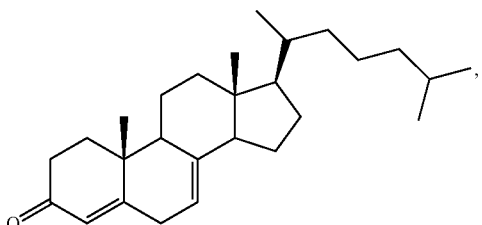

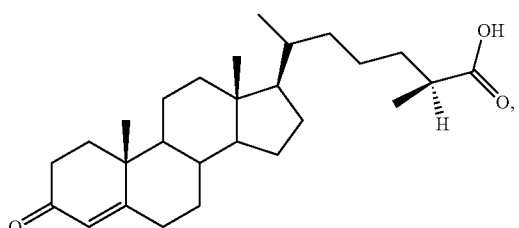

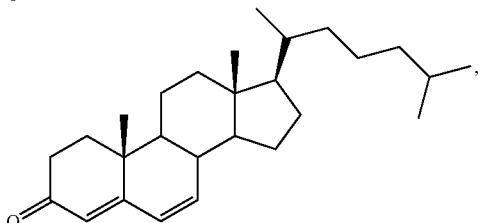

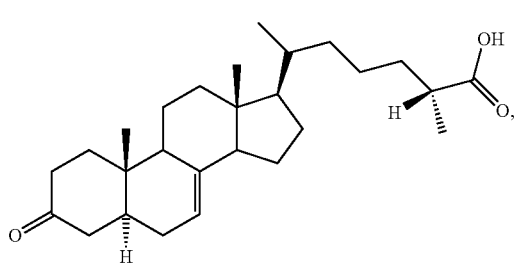

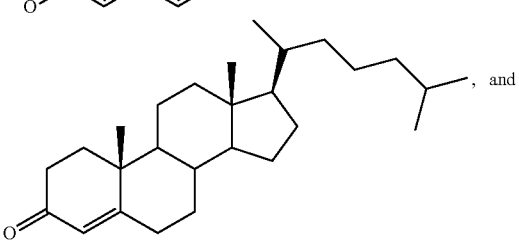,

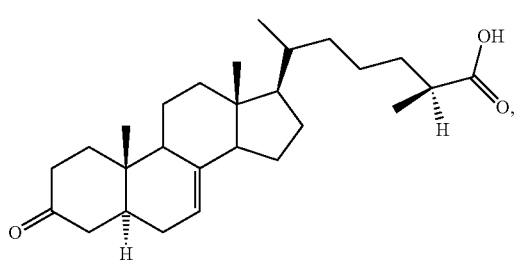

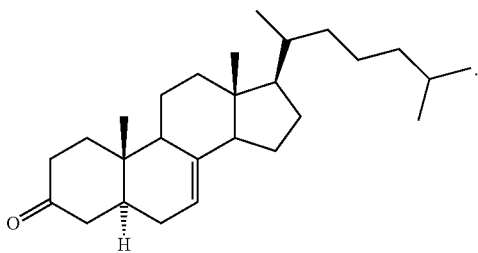, and

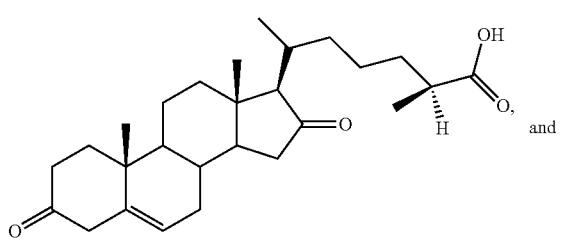

and the steroid precursor is selected from the group consisting of

The compounds of formula I can be produced by means of an insect cell expression system, involving, for example, baculovirus-mediated gene transfer to Sf9 insect cells grown in liquid suspension. Such a baculovirus expression system is readily scaled to industrial level and is used extensively for protein expression. See, e.g., S. R. Hood et al. (1996).

In one such method, Sf9 cells are infected with baculovirus expressing DAF-9 and the human cytochrome P450 oxidoreductase. After supplementation with the appropriate heme precursors and Fe supplements, infected cells are grown for 60 hours in the presence of DAF-9 substrates. Certain DAF-9 substrates are commercially available (4-cholesten-3-one and 4,6-cholestadiene-3-one) while others can be synthesized from commercially available starting materials using cholesterol oxidase to produce 4,7-cholestadiene-3-one from 7-dehydrocholesterol or Dess Martin to produce lathosterone from lathosterol. After about 60 hours, cells and media are harvested and the substrate and products are recovered by extracting with organic solvents. Alternatively, membrane-bound enzyme can be obtained by subcellular fractionation, and the resulting membranes are incubated in a cell-free system with appropriate reducing agents and substrates.

This technique is powerful because it also may be used to reconstitute the entire pathway from cholesterol. In addition, it is possible that enzymes in *C. elegans* modify DAF-12 ligands to convert them into antagonists or partial agonists. Such enzymes could be used in this system for enzymatic synthesis as well.

The compounds of formula I also can be synthesized by chemical methods. For example, various compounds of formula I may be synthesized, via known chemical transformations, from diosgenin or yamogenin:

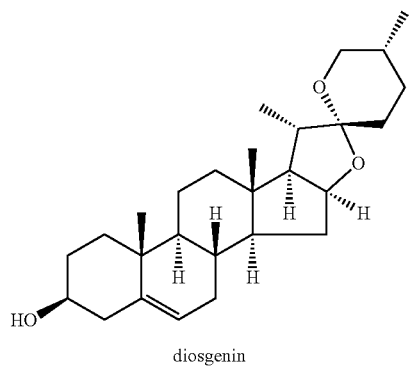

diosgenin

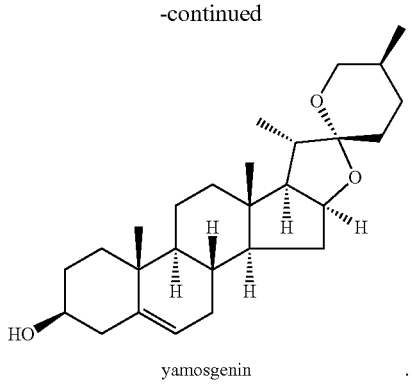

yamosgenin

Thus, diosgenin is converted to 25R-cholest-5-ene-3β,26-diol 3β,26-di-TBDMS ether (1), pursuant to the protocol of Kim et al. (1989), which entails, seriatim, a Clemmensen reduction, a 3,26-diprotection with t-butyldimethylsilylchloride, an oxidation to the 16-keto form, and a deoxygenation of the 16-keto (reactions "a" in Scheme I below).

Scheme I

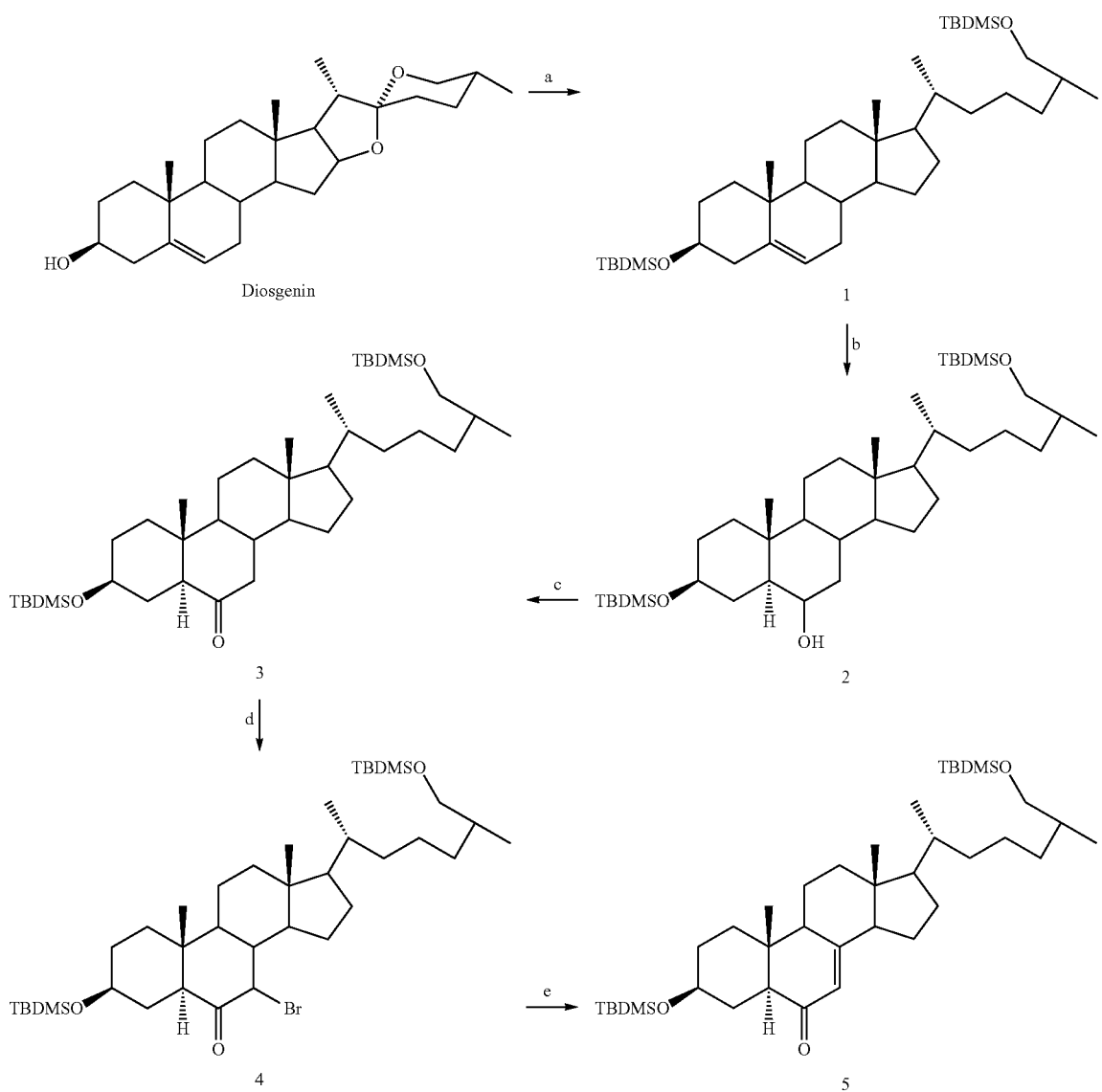

Schemes I-III feature protecting groups at the 3- and 26-hydroxyl groups as t-butyldimethylsilyl groups (TBDMS), yet in some routes these groups must be replaced with acetate or other protecting groups for specific steps as is standard procedure in the art. In the work immediately below, compounds 3, 4, and 5 are also or exclusively described as the 3,26-diacetates.

Via a procedure adapted from Yu et al. (2002), 1 is subject to hydroboration, yielding 5α-25R-cholest-3β,6β,26-triol 3β,26-di-TBDMS ether (2, reactions "b"), and subsequent oxidation of 2 provides 5α-25R-cholest-3β,26-diol-6-one 3β,26-di-TBDMS ether (3, reactions "c"). The procedure is as follows:

To a stirred solution of 1 (1.62 g, 2.57 mmol) in THF (30 mL) is added neat $BH_3 \cdot Me_2S$ (0.7 mL, 7.71 mmol) under positive pressure of argon, and the reaction mixture is stirred for 12 hours at room temperature. After quenching by drop-wise addition of water, an aqueous solution of NaOH (30%, 20 ml) and then $H_2O_2$ (30%, 20 mL) is added, and stirring continues overnight. After an adjustment of pH to 7 with dilute aqueous HCl, the solution is poured into saturated aqueous NaCl (40 mL) and extracted with diethyl ether (60 mL×4). The organic layer is concentrated in vacuo, to afford a residue (1.55 g of crude 2). The crude product is dissolved in 30 mL of dichloromethane, and Dess-Martin periodinane (1.11 g, 2.61 mmol) is added slowly, with stirring. After stirring at room temperature for 5 hours, the suspension is filtered and concentrated in vacuo. The residue is purified by flash chromatography on silica gel with 20:1 petroleum ether/ethyl acetate, to provide 3 (1.21 g, 73% yield from 1) as white solid.

Compound 3 then is converted to its diacetate (aqueous HF, followed by acetic anhydride in pyridine) and subjected to bromination, yielding 5α-25R-cholest-7-bromo-3β,26-diol-6-one 3β,26-diacetate (4, reaction "d"), via the following procedure, adapted from Yu et al (2002): a solution of the diacetate of 3 (0.05 g, 0.099 mmol) in 5 mL dry THF was treated with pyridinium tribromide (0.083, 0.261 mmol) at 0° C. and brought to room temperature. After stirring at room temperature for 1.5 h, saturated $Na_2S_2O_3$ solution (2 mL) was added to quench the reaction. The product was extracted twice into 10 mL of diethyl ether, which was washed with 20 mL each water and brine. The residue was purified by flash chromatography, eluting with 14% ethyl acetate/hexanes to afford 4 (0.045 g, 78%) as a white solid.

Elimination of 4 to 5α-25R-cholest-7-ene-3β,26-diol-6-one 3β,26-diacetate (5, reaction "e") was effected by a procedure adapted from Jiang et al. (2003), as follows: a mixture of 4 (0.012 g, 0.02 mmol), $Li_2CO_3$ (0.0003 g, 0.004 mmol) and LiBr (0.002 g, 0.02 mmol) in 5 mL DMF is heated at 125° C. under nitrogen for 24 hours. After cooling to room temperature, ethyl acetate (30 mL) is added, and the organic layer is washed with water until neutral pH, then dried over $Na_2SO_4$. The solvent is removed in vacuo, and the residue is purified by flash chromatography on silica gel (eluting with 2:3 ethyl acetate/hexanes) to give 5 (0.008 g, 77%) as a white solid.

Compound 5 may be converted into active DAF-12 ligands with a variety of chemical configurations in the A/B ring system and an alcohol or acid at the 26 position. Scheme II describes chemistry, completed or prophetic, for obtaining desired configurations in the A/B ring system. Scheme III describes a common set of reactions applied to the products of Scheme II or to compound 5 itself to complete the synthesis of DAF-12 ligands by removing protecting groups and adjusting the oxidation states of carbon atoms 3 and 26. For example compound 5 is reduced and deoxygenated/isomerized to compound 7 according to the procedures of Haag et al. (1988) and Zheng et al. (2003) (reactions "f"). Several approaches as described below are useful to convert compound 5 to compound 6, in which the A/B ring system is configured according to one of the endogenous DAF-12 ligands identified in this invention. Several intermediates in the synthesis of the final compounds may also be agonists or antagonists (pure, partial, and inverse) for DAF-12 and related receptors in other nematode species.

Scheme II

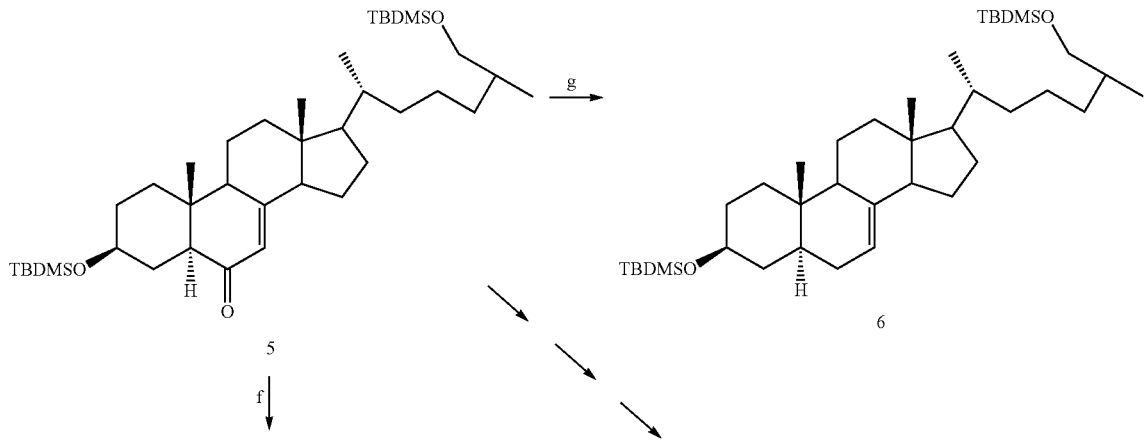

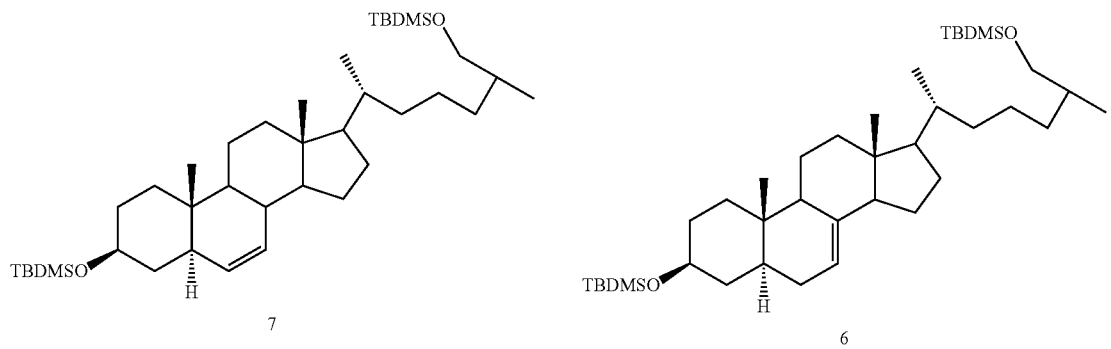

7   6

Compound 5 (0.020 g, 0.034 mmol) was dissolved in a mixture of dry dichloromethane (1 ml) and dry THF (2 ml). After addition of methanol (3 ml), CeCl$_3$.7H$_2$O (0.014 g, 0.037 mmol) was added followed by NaBH$_4$ (0.002 g, 0.05 mmol) at 0° C., and the solution was then allowed to reach room temperature slowly with stirring. After 1 h, the reaction was diluted with chloroform (5 ml) and quenched with 10 mL water. The organic phase was washed with 10 mL each water and brine, and the product was purified by flash chromatography, eluting with 22% ethyl acetate in hexanes to afford a mixture of the 6-alcohols (0.018 g, 90%) as a white solid. The mixture of 6-alcohols (0.0042 g, 0.008 mmol) was dissolved in methylene chloride (5 ml) and cooled to 0° C. Triethylsilane (7.6 μl, 0.048 mmol) was added to the solution, and then boron trifluoride etherate (10 μl, 0.08 mmol) was added dropwise. After the mixture was stirred for 15 min, 10% sodium carbonate (2 ml) was added. The aqueous layer was extracted with 10 mL methylene chloride. The combined methylene chloride extracts were washed with 10 mL brine, dried over anhydrous Na$_2$SO$_4$, and evaporated in vacuo. The residue was purified by flash chromatography, and the product 7 eluted with 14% ethyl acetate in hexanes as a white solid (0.0038 g, 94%).

Several synthetic routes from compound 5 to compound 6 are described below, either as a single reaction sequence (reaction "g"):

1) Modified Wolff-Kishner reduction of ketone 5 (or TBDMS analog) with hydrazine hydrochloride/hydrazine hydrate and potassium hydroxide;
2) Conversion of ketone 5 to the thioketal with ethanedithiol/BF$_3$ etherate and reduction with Raney nickel;

or as multiple-step routes (triple arrows):

1) Reduction of 6-ketone 5 to the 6-alcohols as described above, followed by conversion to 6-bromide with either PBr$_3$ (or 1,2-phenylene phosphorobromidite), or CBr$_4$/triphenylphosphine, followed by
   a) reduction using hydrogen gas/catalyst, zinc dust, sodium or lithium metal.
   b) formation of Grignard reagent with Mg turnings and quenching with ethanol.
2) Reduction of 6-ketone 5 to the 6-alcohols as described above, followed by conversion to 6-iodide with iodine/triphenylphosphine/imidazole followed by reduction with SmI$_2$.
3) Reduction of 6-ketone 5 to the 6-alcohols as described above, followed by elimination using methylsulfonyl chloride/triethylamine to the 5,7-diene; selective 5α-reduction of the delta-5 olefin with H$_2$ gas and Raney nickel or other suitable catalyst.

Scheme III depicts a general route from the diprotected intermediates to the DAF-12 ligands. Thus, deprotection of the TBDMS (or acetate) groups yields the 3,26-diols (e.g., compound 8). Oxidation with CrO$_3$ (Jones reagent) in acetone gives the 3-keto-26-acids directly (Ia, reactions "h"). The 3-keto-26-alcohols (Ib) may be prepared by selective protection of the 26-hydroxyl with TBDMS chloride in methylene chloride (yielding compound 9, reactions "i"), oxidation with Dess-Martin periodinate or pyridinium dichromate (yielding compound 10, reactions "j"), followed by deprotection with aqueous HF (reaction "k"). The 3-hydroxy-26-acids (not shown) are prepared by acetylation of the 26-TBDMS ether with acetic anhydride in pyridine, deprotection/oxidation with Jones reagent, and deprotection of the 3-hydroxyl with aqueous sodium methoxide.

Scheme III

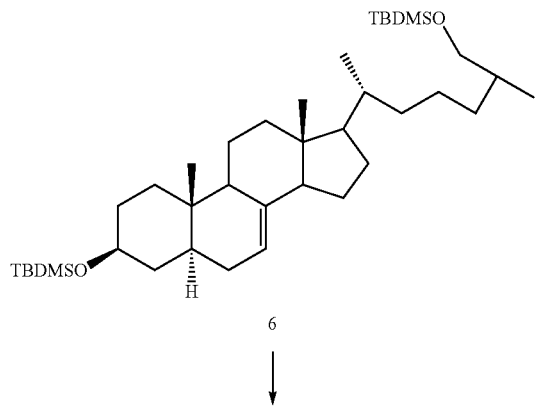

6

↓

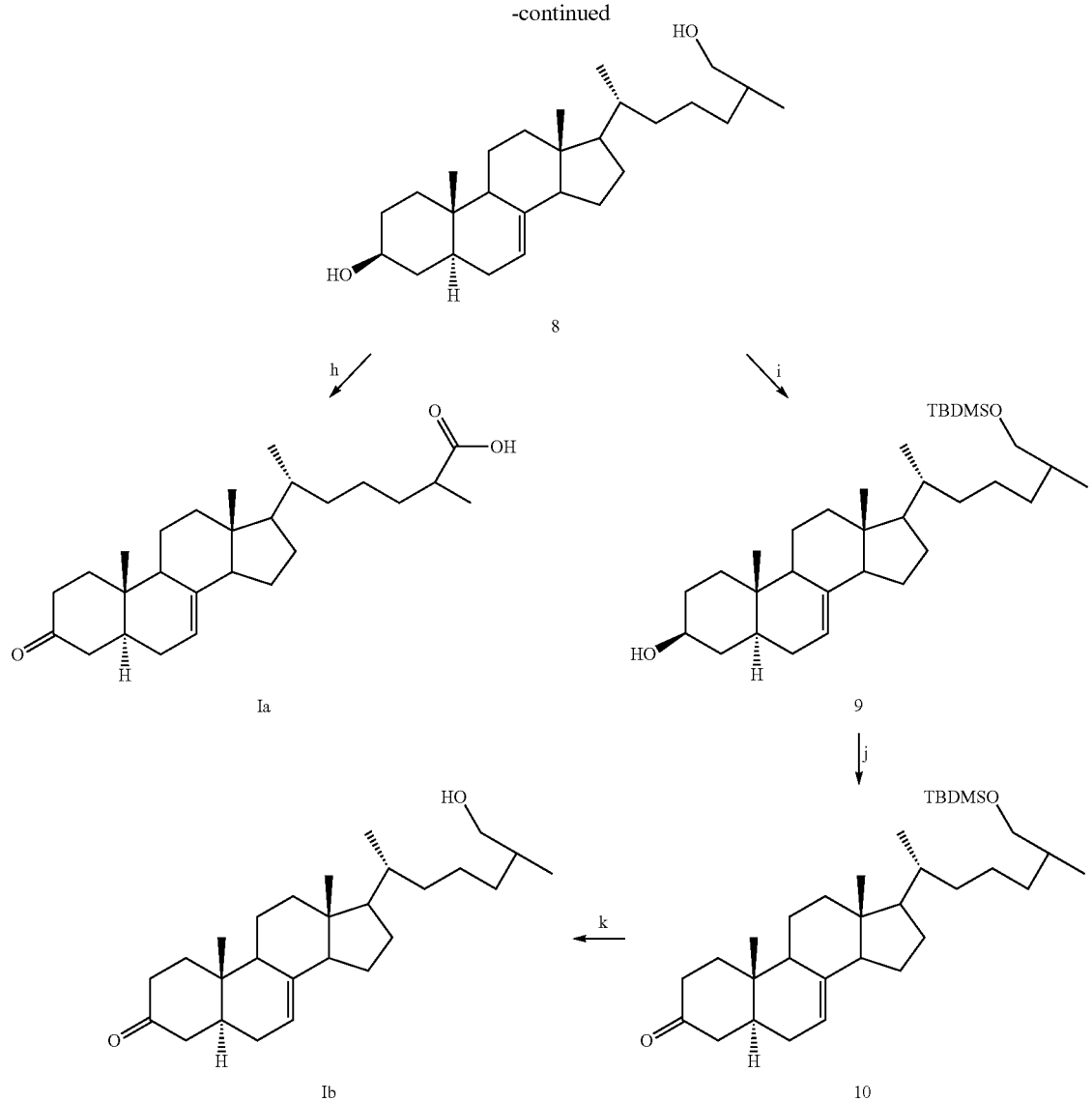

These routes afford several compounds that are 25R isomers from diosgenin and 25S isomers from yamogenin. A scheme for generating 25S isomers from 25R,26-acids (and vice-versa) can be carried out as follows: the 25R acids are converted to their acyl chlorides with $(COCl)_2$ in dimethylformamide. The acyl chlorides are treated with (−)-carenediol and dimethylaminopyridine in THF to yield the carenediol esters. The 25 position is isomerized with potassium t-butoxide in t-butanol at room temperature to the 25R/S mixture. The isomers are separated by reverse phase HPLC and isolated. Hydrolysis of the esters with LiOH in aqueous THF yields the individual acids.

According to another of its aspects, the present invention provides a methodology for identifying a modulator of DAF-12 or a DAF-12 homolog. In general terms, the inventive method employs a cell line, typically mammalian or insect, that is characterized by the presence of an heterologous polynucleotide sequence coding for (i) a polypeptide that contains the full length DAF-12 or ligand-binding domain of DAF-12 ("the DAF-12 polypeptide") and (ii) a DAF-12-responsive reporter, respectively (see below). Cells of such a line are brought into contact with putative modulators, as may be presented in the form of a library of small molecules or peptides, in order to screen for compounds that bind to the DAF-12 domain. In a variation of this approach, the aforementioned cell line is engineered to express DAF-9 as well, and the resultant cells are used to screen for a compound that DAF-9 metabolizes into DAF-12 ligand, which can activate DAF-12 to prevent dauer formation or to drive recovery from dauer.

In accordance with the invention, therefore, an assay can be performed to identify antagonists of either the enzyme, DAF-9, or the receptor, DAF-12, with essentially the same outcome in each instance. Moreover, the assay can be adapted to effect high-throughput compound screens, which may be automated by means of commercially available robotic screening systems, such as CRS Ultra High Throughput Screening System, a product of the Thermo Electron Corporation (Waltham, Mass.).

By way of illustration of such an assay, one can employ conventional recombinant DNA technology, along the lines described by Makishima et al. (1999), to fuse the modular ligand-binding domain of DAF-12 to the C-terminus of the DNA binding domain of the yeast transcription factor, GAL4. The resulting fusion protein can bind specifically to a GAL4 DNA response element in a GAL4-responsive reporter gene plasmid, encoding a detectable marker such as luciferase, whereby receptor activity can be monitored after treatment with putative ligand.

Alternatively, the full-length DAF-12 receptor is used, along with a DAF-12-responsive reporter that also contains one or more DAF-12 DNA response elements, as described, for example, by Shostak et al. (2004). Although similar in certain respects to the foregoing illustration, this assay mode employs a DAF-12-specific reporter gene rather than a GAL4-specific reporter gene. The specificity resides in the DAF-12 DNA response element(s), which were identified within fragments of C. elegans genomic DNA in screens for genomic DNA fragments that bind to DAF-12 in vitro. When linked to a reporter gene such as GFP, these DNA fragments drive expression of GFP in vivo in a DAF-12-dependent manner. With these endogenous DAF-12 response elements, the full-length DAF-12 receptor, containing both natural DNA binding domain and ligand binding domain, must be used in the screen as opposed to the GAL4-hybrid polypeptide. It is possible, however, that these response elements may be regulated by mammalian nuclear receptors; hence, activation of the reporter would need to be tested in absence of DAF-12, to control for the presence of competing nuclear receptors that are endogenous to the cell lines used.

The above-discussed GAL4-responsive luciferase reporter is preferred, because GAL4 is specific to yeast and its DNA response elements are bound only by GAL4. Accordingly, there is no potential for interference from nuclear receptors that may be endogenous to the cell line.

As noted, compound libraries can be screened for agonists/antagonists of DAF-12, once cells are provided that harbor the appropriate receptor and reporter plasmids. It has not been possible to identify antagonists of DAF-12 heretofore, for the simple fact that no one had identified an agonist of DAF-12. Pursuant to the present invention, one can screen for compounds that antagonize activation of DAF-12 by one or more of the DAF-12 ligands described presently, preferably employing a ligand concentration in the range between about $EC_{50}$ and about $EC_{80}$, e.g., approximately 200 nM to 4 µM.

Another approach, according to the invention, is to attack both DAF-9 and DAF-12 together. This can be done by screening for compounds that inhibit the ability of DAF-9 to metabolize its substrates into ligands of DAF-12. This type of antagonist screen would not be possible without the identification of DAF-9 substrates, per the present inventors' discovery. Such a screen allows for detection of compounds that antagonize reporter gene activity at the level of DAF-9 ligand production or DAF-12 activation. The primary target, DAF-9 versus DAF-12, can be determined by removing DAF-9 from the assay and testing the "hit" for antagonism of the DAF-12 ligands described here. Other controls systems may be employed to test for DAF-9 specificity, such as a similar co-transfection system, described by Cheng et al. (2003), that involves cytochrome P450 2R1-mediated activation of the Vitamin D receptor. Briefly, 1αOH vitamin $D_3$ is supplied to cells co-transfected with both CYP2R1 and the vitamin D receptor. The conversion of 1αOHvitamin $D_3$ to 1α,25-dihydroxyvitamin $D_3$ is monitored through activation of the Vitamin D receptor. Lack of inhibition of this system by candidate DAF-9 antagonists would indicate the antagonist properties were specific to the DAF-9 P450 and not a general inhibitor of mammalian P450s.

The DAF-12 ligand and DAF-9 substrates used in the assay include compounds of formula I

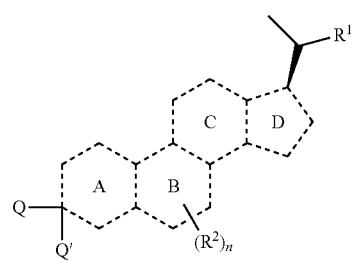

wherein $R^2$ is a substituent on one or more carbon atoms in rings A, B, C, and D and, in each instance, is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', oxo, thione, OR, and SR.

R and R' are independently selected from the group consisting of hydrogen, $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl.

Variable n is selected from the group consisting of 0, 1, 2, 3, 4, 5, 6, 7, 8, 9, and 10.

Each instance of ---- independently is a single bond or a double bond; wherein one of ---- is optionally absent so that one of rings A, B, C or D is no longer a cyclic ring or part of a cyclic ring, and wherein when ---- is absent, the two resultant terminal carbon atoms are substituted with one or more hydrogen atoms to satisfy the carbon atom valencies. For the DAF-12 ligand, $R^1$ is selected from the group consisting of:

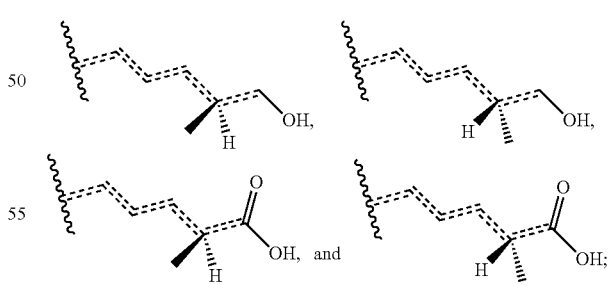

wherein each instance of ≡≡≡ independently is a single bond, a double bond, or a triple bond; and wherein $R^1$ is optionally substituted with 1 to 8 substituents, each of which is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$ heterocycloalkyl($C_1$-$C_6$)alkyl, heteroaryl($C_1$-$C_6$)alkyl, aryl ($C_1$-$C_6$)alkyl, NRR', OR, and SR.

For the DAF-9 substrate, $R^1$ is

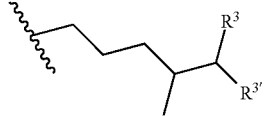

wherein $R^1$ is optionally substituted with 1 to 8 substituents, each of which is independently selected from the group consisting of halo, ($C_1$-$C_8$)alkyl, ($C_2$-$C_8$)alkenyl, ($C_2$-$C_8$) alkynyl, ($C_1$-$C_4$)alkoxy($C_1$-$C_4$)alkyl, ($C_1$-$C_8$)haloalkyl, ($C_1$-$C_8$)hydroxyalkyl, ($C_3$-$C_8$)cycloalkyl, ($C_3$-$C_8$)heterocycloalkyl, heteroaryl, aryl, ($C_3$-$C_8$)cycloalkyl($C_1$-$C_6$)alkyl, ($C_3$-$C_8$)heterocycloalkyl($C_1$-$C_6$)alkyl, heteroaryl($C_1$-$C_6$) alkyl, aryl($C_1$-$C_6$)alkyl, NRR', OR, and SR; and wherein $R^3$ and $R^{3'}$ are independently hydrogen or hydroxy or $R^3$ and $R^{3'}$ together with the carbon atom to they are attached form a carbonyl group.

In some embodiments of the assay, the DAF-12 ligand is selected from the group consisting of

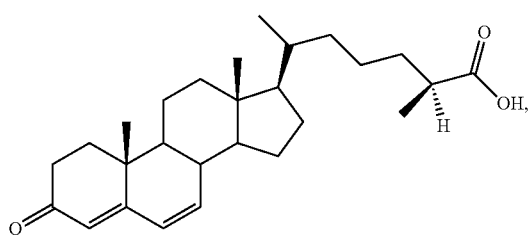

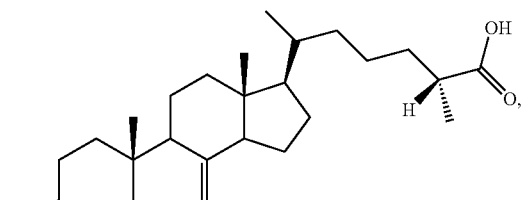

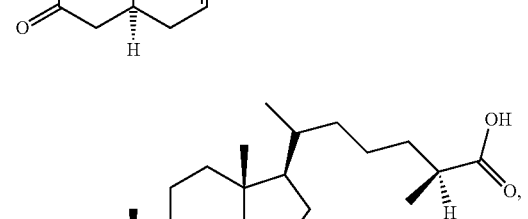

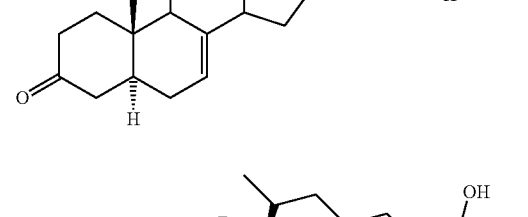

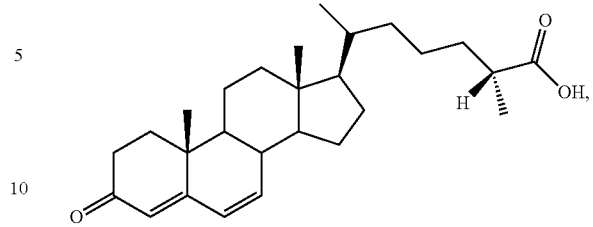

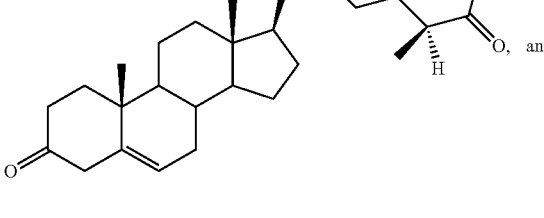

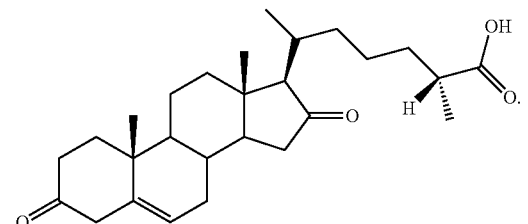

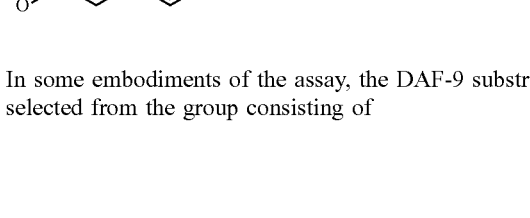

In some embodiments of the assay, the DAF-9 substrate is selected from the group consisting of

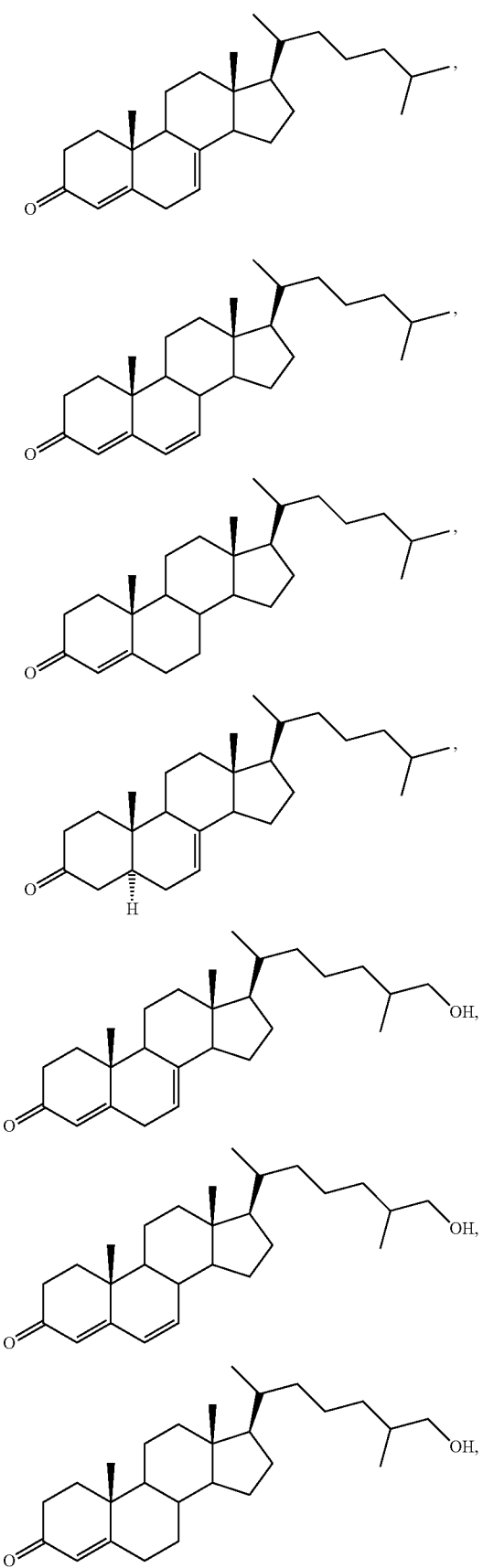

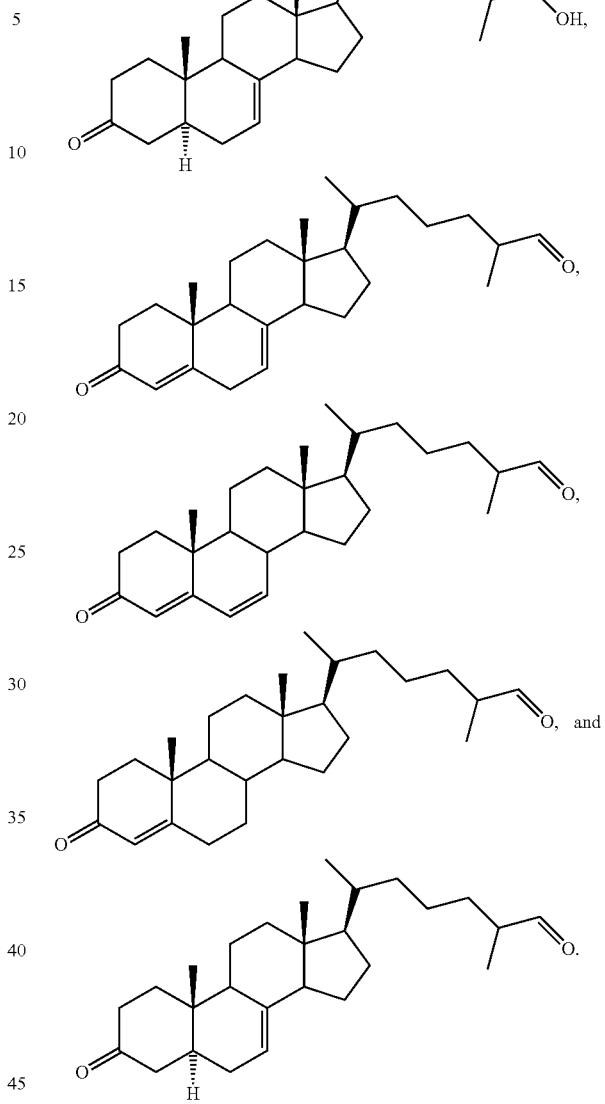

The assay methodology of the present invention can accommodate any of a range of detectable markers, including but not limited to a detectable polypeptide, such as a fluorescent polypeptide, a chemiluminescent polypeptide, an epitope tag, and an enzyme. Thus, a suitable marker can be selected from among human growth hormone, luciferase, chloramphenicol acetyl transferase, xanthine-guanine phosphoribosyl transferase, and β-galactosidase, or a variant of any of these.

According to the invention, the category of DAF-12 modulators includes compounds that act as agonists or antagonists. Screening for agonists entails testing for activation of DAF-12 relative to a vehicle control, using ligands, such as those described here, as a positive control. On the other hand, an antagonist inhibits or reduces (partially antagonizes) the activation of DAF-12 by a DAF-12 ligand, through an ability to bind DAF-12, competitively or non-competitively. The category of DAF-12 modulators also encompasses inverse antagonists, which bind elsewhere than the ligand-binding pocket of DAF-12, to stabilize the inactive conformation of the receptor.

Compounds that modulate DAF-12 through activation can be identified in a screen, pursuant to the present invention. Such compounds may be more potent or efficacious than the endogenous DAF-12 ligand, thereby representing not only a potent activator of DAF-12 but also a new tool to be used in the study of nematode physiology.

In another embodiment, therefore, the invention encompasses a kit for identifying DAF-12 modulators, comprising a compound of formula I or a stereoisomer thereof:

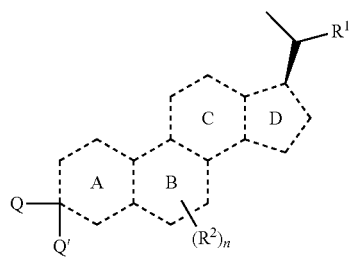

I wherein one of Q or Q' is OH or SH and the other of Q or Q' is hydrogen, or Q and Q' together with the carbon atom to which they are attached form a carbonyl or thiocarbonyl group.

$R^1$ is selected from the group consisting of:

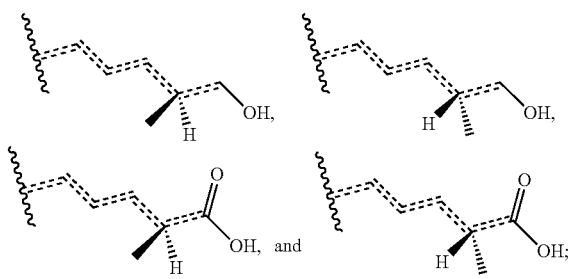

wherein each instance of ≡≡≡ independently is a single bond, a double bond, or a triple bond; and wherein $R^1$ is optionally substituted with 1 to 8 substituents, each of which is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', OR, and SR.

$R^2$ is a substituent on one or more carbon atoms in rings A, B, C, and D and, in each instance, is independently selected from the group consisting of halo, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$haloalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl, aryl$(C_1-C_6)$alkyl, NRR', oxo, thione, OR, and SR.

R and R' are independently selected from the group consisting of hydrogen, $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl.

Variable n is selected from the group consisting of 0, 1, 2, 3, 4, 5, 6, 7, 8, 9, and 10.

Each instance of ---- independently is a single bond or a double bond; wherein one of ---- is optionally absent so that one of rings A, B, C or D is no longer a cyclic ring or part of a cyclic ring, and wherein when ---- is absent, the two resultant terminal carbon atoms are substituted with one or more hydrogen atoms to satisfy the carbon atom valencies.

In one embodiment, the kit contains a cDNA for a DAF-12 polypeptide comprised of a ligand binding domain or a portion thereof and a DNA binding domain or portion thereof, in a DNA plasmid that allows expression of said cDNA in a mammalian cell line. In some aspects, the plasmid is a pCMX-GAL4-DAF12 plasmid.

In another embodiment, the kit contains a cDNA encoding DAF9 polypeptide or modified version thereof with equivalent enzymatic activity in a DNA plasmid that allows expression of said cDNA in a mammalian cell line, such as pCMX-DAF9 plasmid.

In other embodiments, the kit contains a reporter gene DNA plasmid whose expression is driven by activated DAF-12 polypeptide. In some aspects the plasmid is a pMH100x4-luc plasmid that has the firefly luciferase cDNA adjacent to the thymidine kinase promoter and four copies of the GAL4-DNA response element.

In still other embodiments, the kit contains reagents for detecting the expression of the reporter gene, such as the Dual-Luciferase® Reporter Assay System marketed by Promega, Inc. (Madison, Wis.).

In another embodiment, the kit contains a suitable cell line for expression and assay of DAF-12. In some aspects the cell line is a human embryonic kidney (HEK-293) cell line (American Type Culture Collection, Catalog #CRL-1573, Manassas, Va.), or a cell line that stably incorporates and expresses said DAF-12 cDNA in its genome.

In other embodiments, the kit contains reagents for inserting the desired DNA plasmids into the cell line, such as the FuGENE6® reagent (Roche Biochemicals, Indianapolis, Ind.).

* * *

The following examples are provided to illustrate certain aspects of the present invention and to aid those of skill in the art in practicing the invention. These examples are in no way to be considered to limit the scope of the invention.

EXAMPLES

Chemical Reagents

4-Cholesten-3-one, lathosterol, 20S-hydroxycholesterol, 22S-hydroxycholesterol, 22R-hydroxycholesterol, 24S-hydroxycholesterol, 25-hydroxycholesterol, 3-keto-lithicholic acid, 7-keto-lithocholic acid, 12-keto-lithocholic acid were purchased from Steraloids, Inc. (Newport, R.I.). Lophenol, (25S),26-hydroxycholesterol, and (25R),26-hydroxycholesterol were purchased from Research Plus (Manasquan, N.J.). Unless otherwise noted, all other reagents were purchased from Sigma. All sterols were dissolved in ethanol and stored at −20° C.

Sterol Synthesis

The 3-keto-Δ$^4$-oxysterol derivatives in FIG. 3A were generated with cholesterol oxidase and catalase as described (Zhang et al. 2001). The 3-keto sterols of lathosterol and lophenol (lathosterone and lophenone) were generated by chemical oxidation with Dess-Martin periodinane reagent. Briefly, 2.5 molar equivalents of Dess-Martin reagent were reacted with one equivalent of each sterol at room temperature. Reactions were monitored by TLC using 95:5 hexane:ethylacetate. Lophenone and lathosterone were purified from starting materials using silica chromatography with 95:5 hexane:ethylacetate. Structures were confirmed by $^{13}C$ and $^{1}H$-NMR. To oxidize (25R) and (25S),26-hydroxy-4-cholesten-3-one into C-26 acids, Jones reagent (0.14 mL, 0.15 mmol) was added slowly and dropwise to a stirred solution of the alcohol (12 mg, 0.03 mmol) in acetone (4 mL) at 0° C. After stirring for 1 hour, the reaction was quenched with isopropanol, and the product extracted with diethyl ether. The organic phase was washed with saturated $NaHCO_3$, dried over solid $Na_2SO_4$, filtered, and concentrated in vacuo. Crude extracts were chromatographed on silica gel, and the product (10 mg, 90% yield) eluted with 40% ethyl acetate in hexane. All structures were confirmed by MS, UV spectra, and $^{13}C$- and $^{1}H$-NMR (FIG. 11).

Alternate Syntheses of Compounds of Formula I

The following examples illustrate synthetic routes other than those depicted in Schemes I-III above by which to make compounds of Formula I.

25(R)-cholest-5-en-3β,26-diacetate (II)

To a solution of 25(R)-cholest-5-en-3β, 26-diol (1.31 g, 3.25 mmol, prepared as described in the procedure above for 1; Scheme 1, reaction "a") in dry pyridine (15 mL), were added acetic anhydride (3 mL) and N,N-dimethylaminopyridine (4 mg, 0.027 mmol). The mixture was stirred at room temperature under nitrogen for 18 h. Water (5 mL) was added, and the product was extracted with ethyl acetate. The organic layer was washed with $NaHCO_3$, then water, and dried over $Na_2SO_4$. The solvent was evaporated to dryness. The crude product was subjected to MPLC (silica gel 60-200 mesh, 1.0×12 inch column, elution with ethyl acetate-hexanes 6:100) to give II (1.21 g, 76%).

25(R)-7-bromo-cholest-5-ene-3β,26-diol-3β,26-diacetate (III)

To a solution of II (0.081 g, 0.166 mmol) in benzene-hexane 1:1 (10 mL) was added N,N-dibromohydantoin (0.023 g, 0.083 mmol). The mixture was refluxed under nitrogen for 10 min in a preheated oil bath at 100° C. and then placed in an ice bath to cool. Insoluble material was removed by suction filtration, followed by evaporation of the filtrate to a yellow solid. The crude product can be purified and the unreacted starting material recovered/recycled, or crude III can be used directly in the next reaction.

25(R)-cholest-5,7-diene-3β,26-diol-3β,26-diacetate (IV)

To a solution of the yellow solid (crude III) in anhydrous tetrahydrofuran (8 mL) was added tetrabutylammonium bromide (0.016 g, 0.049 mmol). The resulting solution was stirred for 75 min under nitrogen at room temperature and then treated with tetrabutyl ammoniumfluoride (0.35 ml, 1M solution in THF, 0.35 mmol, 2.1 equivalents). The resultant dark brown solution was stirred for an additional 50 min, followed by rotatory evaporation to a brown solid. The residue was dissolved in ethyl acetate (100 mL), washed with water (3×25 mL), and dried over $Na_2SO_4$. Evaporation of solvent gave crude IV (0.1 g), which was subjected to MPLC on $AgNO_3$ impregnated silica to afford 0.02 g (25%). Unreacted II is recovered following MPLC.

25(R)-cholest-7-ene-3β,26-diol-3β,26-diacetate (V)

To a solution of IV (0.015 g, 0.03 mmol) in freshly distilled ethyl acetate (7 mL) was added platinum (IV) oxide catalyst (Aldrich P345). The mixture was stirred at ambient temperature for 2 h in 1 atm of hydrogen gas. After completion of reaction, the reaction mixture was filtered through a small plug of silica gel and purified on silica gel 60-200 mesh by standard column chromatography, eluting with 6% ethyl acetate in hexanes to afford 0.014 g (89%).

25(R)-cholest-7-ene-3β,26-diol (VI)

To a solution of diacetate V (0.012 g, 0.024 mmol) in moist methanol was added 200 mg of KOH. After refluxing for 4 h, the reaction mixture was neutralized with dilute HCl, and the methanol was removed under reduced pressure. The residue was dissolved in diethyl ether, which was washed with 2% $NaHCO_3$ and dried over $Na_2SO_4$. After evaporation under reduced pressure, the product was chromatographed on silica gel 60-200 mesh by standard column chromatography and eluted with 22% ethyl acetate in hexanes to afford 0.009 g VI (90%).

25(R)-cholest-7-ene-26-al-3-one (VII)

To a solution of diol VI (0.008 g, 0.019 mmol) in dry dichloromethane (4 mL) at ambient temperature was added Dess-Martin periodinane (0.017 g, 0.04 mmol). After 4 h, the reaction was quenched with saturated $Na_2S_2O_3$ solution and diluted with 100 mL dichloromethane. The organic phase was washed with 3×25 mL saturated $Na_2S_2O_3$ solution and brine, then dried over $Na_2SO_4$. After evaporation under reduced pressure, the residue was chromatographed on silica gel 60-200 mesh by standard column chromatography, and the product eluted with 6% ethyl acetate in hexanes to afford 0.007 g VII (88%).

25(R)-cholest-7-ene-3-one-26-oic acid [25(R)-$\Delta^7$-dafachronic acid] (VIII)

To a stirred solution of aldehyde VII (0.006 g, 0.015 mmol) in methanol (3 mL) was added isobutene (0.016 µl, 0.15 mmol), then 0.0028 g of 1.25 M $NaClO_2$ in 20% $NaH_2PO_4$,** and stirring was continued at room temperature for 1 h. The reaction was quenched with saturated $NH_4Cl$ solution and diluted with 100 mL of diethyl ether. The organic phase was washed with 3×25 mL 2% $NaHCO_3$ solution, then brine, and dried over $Na_2SO_4$. After evaporation under reduced pressure, the residue was chromatographed on silica gel 60-200 mesh by standard column chromatography, and the product eluted with 32% ethyl acetate in hexanes to afford 0.005 g VIII (80%).

**1.25 M $NaClO_2$ in 20% $NaH_2PO_4$ was prepared by adding 0.57 g $NaClO_2$ to a 20% solution of $NaH_2PO_4$ in $H_2O$ (1 g $NaH_2PO_4$+5 mL $H_2O$)

The following procedures can be adapted to compounds of Formula I in converting 25(R)-cholestenoic acids and precursors to their 25(S)-isomers.

Isomerization of 25(R)-cholest-7-ene-26-al-3-one (VII) to 25(R,S)-cholest-7-ene-26-al-3-one (VIIa)

(25R)-Cholest-7-ene-3-keto, 26-aldehyde

To epimerize the stereochemistry at carbon-25, 25(R)-aldehyde VII (0.007 g, 0.017 mmol) was dissolved in THF (5 mL), and 1,8-diazabicyclo[5.4.0]undec-7-ene (0.3 mL) was added, followed by stirring at ambient temperature for 48 h. The THF was evaporated under reduced pressure, and the residue was dissolved in ethyl acetate, which was washed with brine and dried over $Na_2SO_4$. After evaporation under reduced pressure, the residue was chromatographed on silica gel 60-200 mesh by standard column chromatography, and the product eluted with 6% ethyl acetate in hexanes to afford 0.006 g VIIa (85%). $^{1}H$-NMR shows epimerization of aldehyde proton (two doublets).

The resulting aldehydes are oxidized to epimeric acids VIII or reduced to epimeric alcohols VI. The epimers can be resolved by high-performance liquid chromatography before or after derivatization as chiral esters with chiral auxiliaries, such as (−)-carenediol or Mosher ester.

The reactions below are described with model compound and precursor 25(R)-cholest-5-ene-3β,16β,26-triol (IX), which contains an extra 16-hydroxyl group relative to compounds of Formula I. The procedures therefore can be carried out to make compounds of this invention.

25(R)-cholest-5-ene-3β,16β-diol-26-tosylate (X)

To a solution of triol IX (0.2 g, 0.47 mmol) in pyridine (4 mL) was added slowly p-toluenesulfonyl chloride (0.1 g, 0.52 mmol) at −10° C., and the reaction was stirred at room temperature for 24 h. After completion of reaction, ether (100 mL) was added, and the organic phase was washed with saturated $CuSO_4$ (3×25 mL), dried over $Na_2SO_4$, and evaporated. The residue was purified by column chromatography with silica gel 60-200 mesh using 22% ethyl acetate in hexanes, which afforded X (0.16 g, 60%).

25(R)-26-iodo-cholest-5-ene-3β,16β-diol (XI)

A mixture of tosylate X (0.15 g, 0.26 mmol), acetone (6 mL, freshly purified with $KMnO_4$ and distilled from $K_2CO_3$) and NaI (0.14 g, 0.96 mmol) was stirred in the dark at 80° C. for 6 h. After completion of reaction, ethyl acetate (100 mL) was added, and the organic phase was washed with water (3×25 mL), dried over $NaSO_4$, and evaporated to dryness. The residue was purified by column chromatography with silica gel 60-200 mesh using 20% ethyl acetate in hexanes, affording iodide XI (0.11 g, 80%).

25(R)-cholest-5,25(26)-diene-3β,16β-diol (XII)

To a stirred solution of iodide XI (0.14 g, 0.26 mmol) in dry pyridine (4 mL) was added under argon silver fluoride (0.065 g, 0.52 mmol). The reaction mixture was stirred at ambient temperature for 12 h and then diluted with diethyl ether (100 mL), which was washed with a saturated solution of $CuSO_4$ (3×25 mL) and dried over $Na_2SO_4$. After evaporation of the solvent, the residue was purified by column chromatography with silica gel 60-200 mesh using 18% ethyl acetate in hexanes to afford diene XII (80 mg, 75%).

The above diene can be regioselectively and stereoselectively converted to the 25(S) alcohol by hydroboration with (−)-diisopinocamphenylborane and oxidative work up with $H_2O_2$. The steps described above can be used to convert II to its 25(S) isomer. The synthetic methodology can be used to convert II to the 25(S)-3-keto-7,(5α)-cholestenoic acid VIII.

Alternatively, intermediate compounds can be subjected to Oppenaur oxidation/isomerization, using aluminum isopropoxide and N,N-dimethylamino pyridinone, to make 25(R)- or 25(S) 3-keto-4-cholestenoic acids.

Nematode and Bacterial Strains

Worms were grown on NGM agar seeded with OP50 bacteria at 20° C. unless noted otherwise (Brenner, 1974). Strains used were: daf-9(dh6) dhEx24 (containing the cosmid T13C5 and pTG96 (sur-5::gfp)), daf-9(rh50), daf-12(rh273), and daf-12(rh61), daf-2(e1368), daf-2(e1370) daf-7(m62) and N2.

Plasmids

Inserts of the various cDNAs described below were cloned in to mammalian expression plasmids and their derivatives containing the VP16 activation domain or GAL4 DNA binding domain as described (Umesono et al., 1991; Willy et al., 1995). Full length cDNAs for NHR-8 (Genbank NM_171382, wormbase F33D4.1a), NHR-23 (C01H6.5b), DAF-9 (Genbank NM_171699, wormbase T13C5.1b), and DIN-1S (wormbase F07A11.6d), were obtained by RT-PCR from mixed stage or L2/L3 staged animals. pCMV-hCYP27A1, pCMV-mCYP27A1, and pCMV-adrenodoxin were gifts from David Russell. Human P450 oxidoreductase cDNA was purchased from Open Biosystems. GAL4 fusions were generated based on the following amino acid sequences: 184-754aa (DAF-12), 92-561aa (NHR-8), 78-361aa (NHR-23), 2-567aa (DIN-1S). VP16-DAF-12 fusion was generated using 2-754aa of DAF-12. The R564C and R564H mutants of DAF-12 were generated by site directed mutagenesis. The lit-1K-tk-luc reporter was generated by inserting the 4.2 genomic fragment from pODLO_82 into the reporter plasmid tk-luc. Baculovirus expression plasmids containing DAF-9 and hOR were created using the pFastBac Dual system (Invitrogen).

Cell Culture and Cotransfection Assay

Cotransfection assays in HEK293 cells were performed as previously described using a 96-well format (Makishima et al., 1999). DNA was delivered to cells containing 50 ng of luciferase reporter, 20 ng CMX-β-galactosidase reporter, 15 ng of CMX receptor expression plasmid, and enough control plasmid to maintain 150 ng/well and/or normalize levels of CMV promoter-based plasmids across conditions. Candidate ligands were added at 4000-fold dilution 8 h posttransfection. Luciferase activities were determined and normalized to the β-galactosidase control. Data represent the mean±SD of triplicate assays.

Preparation of DAF-9 and Control Microsomes from Sf9 Cells

Sf9 (2×106 cells/ml) were cultured in SF-900 SFM and were infected with baculovirus at an MOI of 2-4. Cells were supplemented with 0.5 μg/mL hemin chloride, 100 μM δ-amino-levulinic acid, and 100 μM ferric citrate at the time of infection. Infected cells were harvested 60 hours post-infection and microsomes prepared according to methodology described, for instance, by Hood et al. (1996).

DAF-9 Microsomal Incubations

Microsomes containing hOR or hOR and Daf-9 generated from Sf9 cells were thawed on ice and added to a final concentration of 0.5 mg/mL in 0.1M potassium phosphate buffer in the presence of an NADPH regenerating system (50 U/mL DL-isocitrate dehydrogenase, 0.1 M isocitrate and 0.1 M $MgCl_2$). Substrates were added from stock solutions at $10^{-2}$ M to a final concentration of 100 μM (final reaction volume of 0.5 mL). The mixture was preincubated for 3 min at 37° C. and the reaction was initiated by the addition of NADPH (1 mM). After 16 hrs, the reactions were stopped by extraction with 2×2 mL of methyl-tert-butyl-ether and the top layers were combined and dried under nitrogen. In some experiments, 0.5 μg of 1,4-cholestadiene-3-one was added as an internal standard for the extraction.

Rescue Assays

Microsomal reactions were extracted with methyl-tert-butyl ether, dried under nitrogen, resuspended in 50 μl methanol, and mixed with 5× concentration of HB101 bacterial paste. The resulting mixtures were vacuum dried, resuspended in 100 μl of 5× concentrated HB101, and plated on 3 cm plates containing 4 mL NG agar. For rescue, ~200 embryos from a 4-8 hour egg laying were transferred onto the dried bacterial lawn. Mixtures of daf-9(+),gfp(+) and daf-9(−),gfp(−) embryos were placed on agar plates containing a mixture of bacteria and extracts from either DAF-9 or control microsomal reactions. daf-9(+),gfp(+) animals were removed after 48 hrs and the remaining daf-9(−),gfp(−) animals were later scored for dauer arrest. For rescue experiments using pure steroids, 10 μl of compounds were mixed with 5× (90 μl) concentrated OP50 bacteria and plated. Final concentrations in the agar were calculated as equally distributed over the total volume of agar (3-4 mL/plate). Strains tested were grown reproductively onto regular NG agar for 2 generations at 20° C.

*C. elegans* Lipid Extracts

Worms were grown on twenty 10 cm NGM plates seeded with HB101 bacteria. Gravid adults were bleached and the resulting embryos incubated in 2.8 L Fernbach flasks containing 100-350 mL S-medium supplemented with 5 μg/mL Nystatin, 50 μg/mL streptomycin sulfate overnight to allow synchronization of L1s (Stiernagel, 1999). Two successive rounds of growth (with 1-2% HB101) and lysis of gravid adults were performed until ~100-300 million synchronized L1 larvae were obtained. Final growth to the L3/L4 stage was performed in a 15 L New Brunswick BiofloIV fermentor, with a working volume of 10.5 L at 20° C. with agitation (100 RPM, 25% O2 saturation). Worms were harvested and bacteria and debris were removed by sucrose flotation, then frozen in liquid nitrogen and stored at −80° C. Thawed worms were lyophilized for measurement of dry weight, resuspended in 0.1M NaCl and homogenized using an Emulsi-flex C-5 homogenizer (Avestin, Ottawa, Canada). Total lipids were extracted using 2:1 chloroform:methanol. The resulting chloroform layer was collected and back-extracted with two-thirds volume of water. The final chloroform layer was dried with $Na_2SO_4$, filtered through Whatman filter paper and then concentrated in vacuo. The resulting lipid extract was re-suspended in chloroform and adsorbed to a silica column. Lipids were eluted from the column in three fractions using 100 mL chloroform, 200 mL 9:1 acetone:methanol, and 200 mL methanol. The 9:1 acetone:methanol extract was further fractionated by silica chromatography using chloroform and increasing concentrations of methanol to 100%. Fractions were dried under a stream of $N_2$ and tested for DAF-12 activation.

LC/MS Analysis

Samples were analyzed by LC/MS using a DAD in tandem with an MSD single quadropole instrument (Agilent Technologies, Palo Alto, Calif.) with API-ES in both positive and negative ion modes. Samples were dissolved in methanol and loaded onto a pre-column (Zorbax $C_8$, 4.6× 12.5 mm, 5 μm, Agilent) at 4 ml/min for 1 min with 30:70 methanol/water, both containing 5 mM $NH_4Ac$, and then back flushed onto the analytical column at 0.4 ml/min (Zorbax $C_{18}$, 4.6×50 mm, 5 μm, Agilent). The mobile phase consisted of methanol (A) and methanol/acetonitrile/water (60:20:20) (B), both containing 5 mM ($NH_4Ac$). The following gradient was run for a total of 20 min: 0-6.5 min, 75% to 100% (A); 6.5-18 min, 100% (A); 18.1-20 min, 75% (A). MS parameters were as follows: gas temperature 350° C., nebulizer pressure 30 psig, drying gas (nitrogen) 12 L/min, VCap (positive and negative) 4000V, fragmentor voltage 150V (positive ions) or 200V (negative ions). For experiments in scan mode (positive or negative), mass ranges between m/z 250-500 were used. Using selective ion monitoring (in positive ion mode), signals for $[M+H]^+$ ions were observed for 4-cholesten-3-one (m/z 385, retention time (RT) 12.5 min), lathosterone (m/z 384, RT 14.0 min), 1,4-cholestadien-3-one (m/z 383, RT 10.2 min), (25R/S),26-hydroxy-4-cholesten-3-one (m/z 401, RT 5.7 min), (25R/S), 26-3-keto-4-cholestenoic acid. Selective ion monitoring (SIM) in negative ion mode gave signals for $[M-H]^-$ ions of (25R/S),26-3-keto-4-cholestenoic acid (m/z 413, RT 4.0 min). Both positive and negative ions were monitored simultaneously for samples run in SIM mode. Separation of 4-cholesten-3-one oxysterols was achieved as described (Uomori et al., 1987). Briefly, samples were loaded onto the pre-column as described above and back flushed onto a TSK-gel ODS-120T column (4.6×250 mm, 5 μm, Tosoh Biosep, Montgomeryville, Pa.) running 1 ml/min 7% water in methanol (both with 5 mM $NH_4Ac$). Total run time was 30 min and the analytes were monitored by UV absorbance at 240 nm.

Binding Assays

DAF-12 ligand binding domain (aa 507-753) was expressed in BL21(DE3) cells as a 6×His-GST fusion protein using pET24a (Novagen). Ligand binding was determined by AlphaScreen assays from Perkin-Elmer (Xu et al., 2002) with approximately 40 nM receptor and 40 nM of biotinylated SRC1-4 (QKPTSGPQTPQAQQK-SLLQQLLTE) peptide in the presence of 5 μg/mL donor and acceptor beads in a buffer containing 50 mM MOPS, 50 mM NaF, 50 mM CHAPS, and 0.1 mg/mL bovine serum albumin at pH 7.4. $EC_{50}$ binding values were determined from nonlinear least square fit of the data based on an average of three experiments.

To screen for sterol-derived ligands of DAF-12 a co-transfection assay in HEK293 cells was performed using a chimeric GAL4-DAF-12 receptor and a GAL4-responsive luciferase reporter. Assays were performed in the presence or absence of co-transfected DAF-9 due to the strong genetic evidence suggesting it plays an important role in the synthesis of the DAF-12 ligand (Gerisch and Antebi, 2004; Gerisch et al., 2001; Gill et al., 2004; Jia et al., 2002; Mak and Ruvkun, 2004). Our initial compound screen consisted of bile acids and known vertebrate steroid and endocrine hormones as these compounds are ligands for PXR, VDR and LXR, the closest vertebrate homologs of DAF-12 (Antebi et al., 2000; Mooijaart et al., 2005).

Figure 1A:
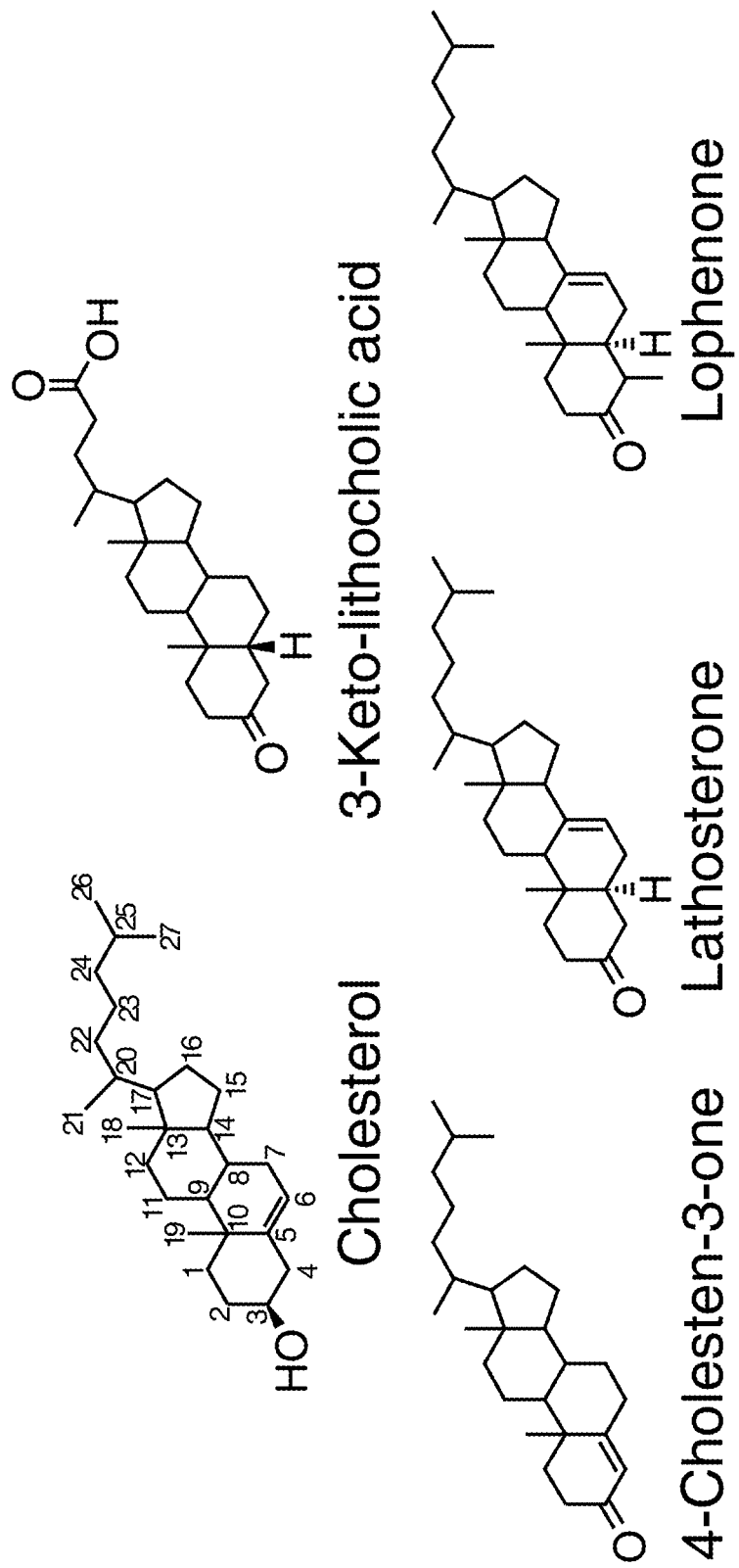
FIG. 1 (A) shows structures of DAF-12 ligand precursors relative to cholesterol and 3-keto-lithocholic acid.
Figure 1C:
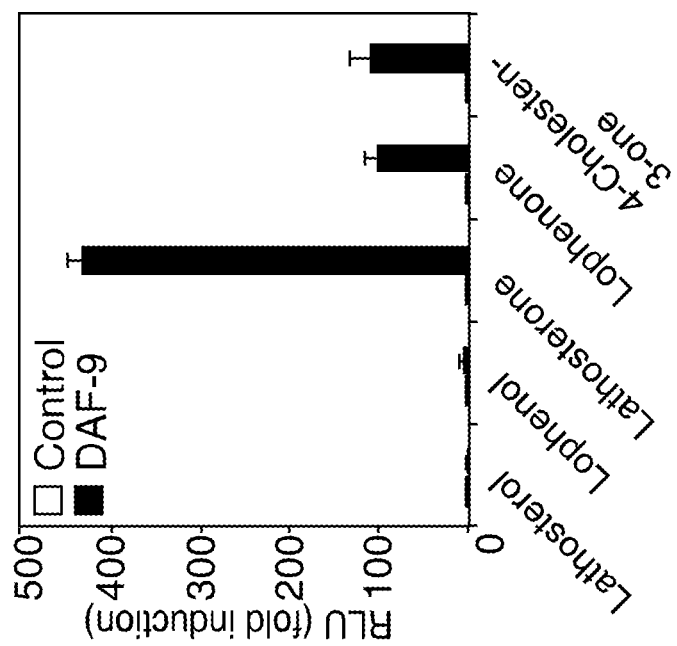
Figure 1B:
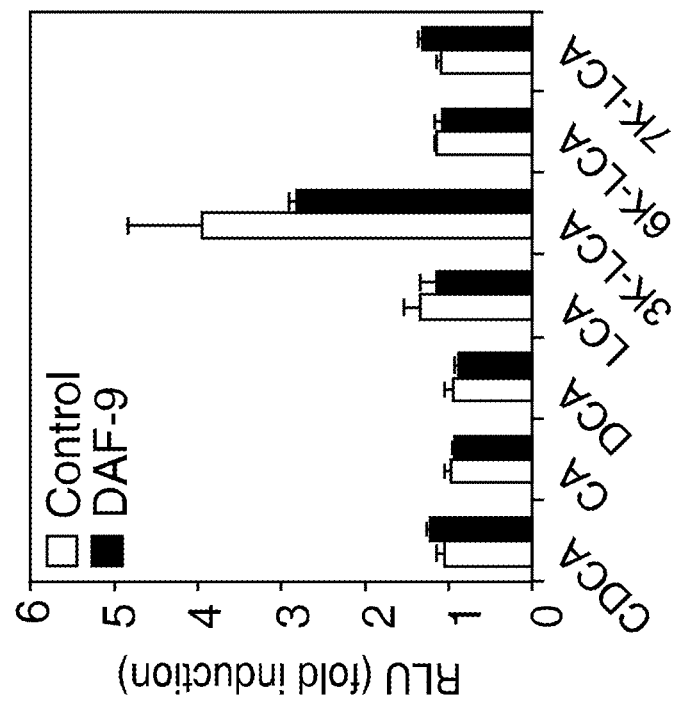

The initial screen identified the bile acid, 3-keto-lithocholic acid (3K-LCA, FIG. 1A) as a weak, micromolar activator of DAF-12 independent of DAF-9 (FIG. 1B). Interestingly, lithocholic acid (LCA), which differs from 3K-LCA by an α-hydroxyl group at C-3, did not exhibit activity on its own or in the presence of co-transfected DAF-9 (FIG. 1B). These results suggested that a C-3 ketone was required for DAF-12 activation by 3K-LCA. No other bile acids or endocrine hormones tested activated DAF-12, including cholic acid (CA), chenodeoxycholic acid (CDCA), deoxycholic acid (DCA), 6-keto-lithocholic acid (6K-LCA), 7-keto-lithocholic acid (7K-LCA), progesterone, pregnenolone, testosterone, estradiol, corticosterone, 1,25-dihydroxyvitamin D3, and 20-hydroxyecdysone (FIG. 1B).

The foregoing data suggested that endogenous 3-keto sterols from C. elegans are candidate DAF-12 ligands. Lathosterol and its 4-methyl-derivative, lophenol, are cholesterol metabolites that have distinct effects on the nematode life cycle (Chitwood et al., 1983; Matyash et al., 2004; Merris et al., 2003). When given as the sole dietary sterol, lathosterol supported full reproductive growth (Merris et al., 2003), while worms grown only in the presence of lophenol constitutively entered dauer diapause (Matyash et al., 2004). These studies suggest lathosterol but not lophenol may be a direct precursor to the DAF-12 ligand. Since activation by 3K-LCA required a C-3 ketone, lathosterol and lophenol were tested along with their respective 3-keto derivatives, lathosterone and lophenone, for activity in the co-transfection assay. Upon co-transfection with DAF-9, activation of DAF-12 was markedly increased by lathosterone (433-fold) and lophenone (103-fold), but not by their respective 3β-hydroxy derivatives (FIG. 1C). In addition, 4-cholesten-3-one, a natural oxidation product of cholesterol, activated DAF-12 (109-fold) in the presence of DAF-9 (FIG. 1C). Unlike 3K-LCA, activation of DAF-12 by lathosterone, lophenone, and 4-cholesten-3-one required the presence of DAF-9. Structurally, 3K-LCA differs from these 3-keto-sterols in the length and oxidation state of the side chain and in the saturation of the sterol nucleus (FIG. 1A). These results revealed that DAF-9 metabolizes 3-keto-sterols, possibly through side-chain oxidation, into DAF-12 activators.

DAF-9 Metabolites of 3-Keto-sterols Rescue Daf-9 Null Worms

The 3-keto-sterol metabolites were tested for their ability to rescue the Daf-c and Mig phenotypes of daf-9 null animals (Albert and Riddle, 1988; Gerisch et al., 2001; Jia et al., 2002). Individual 3-keto sterols and their respective 3β-hydroxy sterols were incubated with Sf9 cell microsomes co-expressing DAF-9 and the human P450 oxidoreductase (hOR). As a control, microsomes from cells expressing hOR alone were used. For rescue experiments daf-9(dh6)dhEx24, which carries an unstable extrachromosomal array of daf-9 (+) and the nuclear marker sur-5:GFP, was utilized (Gerisch et al., 2001). Extracts from DAF-9 microsomes incubated with either 4-cholesten-3-one or lathosterone resulted in 100% rescue of the Daf-c phenotypes of animals lacking the daf-9(+) array (FIG. 1D). Remarkably, these animals were indistinguishable from wild-type adults. Indeed, they bypassed dauer, exhibited normal gonadal migration, and produced all Daf-c progeny upon passage to plates lacking microsomal extracts. Rescue by 4-cholesten-3-one and lathosterone required metabolism by DAF-9, since incubation of these sterols with control microsomes did not rescue any daf-9 phenotypes. Interestingly, extracts from DAF-9 microsomes incubated with lathosterol only partially rescued (83%) the Daf-c phenotype (FIG. 1D). However, the rescued animals exhibited the Mig phenotype and were sterile. This effect also required DAF-9 as no effect was seen after incubation of lathosterol with control microsomes. Finally, although incubation of lophenone with DAF-9 microsomes resulted in rescue of Daf-c, none of these animals were normal (58% were Mig and the remaining 42% failed to enter dauer, had molting defects, or were dead) (FIG. 1D). This effect was dependent on DAF-9 and the C-3 ketone in lophenone, since lophenol had no effect on daf-9 animals after incubation with DAF-9 or control microsomes. Notably, no effect was seen after incubation of cholesterol with DAF-9 or control microsomes. Altogether, the in vivo rescue assays revealed that DAF-9 microsomes metabolize 4-cholesten-3-one and lathosterone into activities that completely rescued both the Daf-c and Mig phenotypes of daf-9 null animals.

Identification of DAF-9 Metabolites of 4-Cholesten-3-one

Figure 2A:
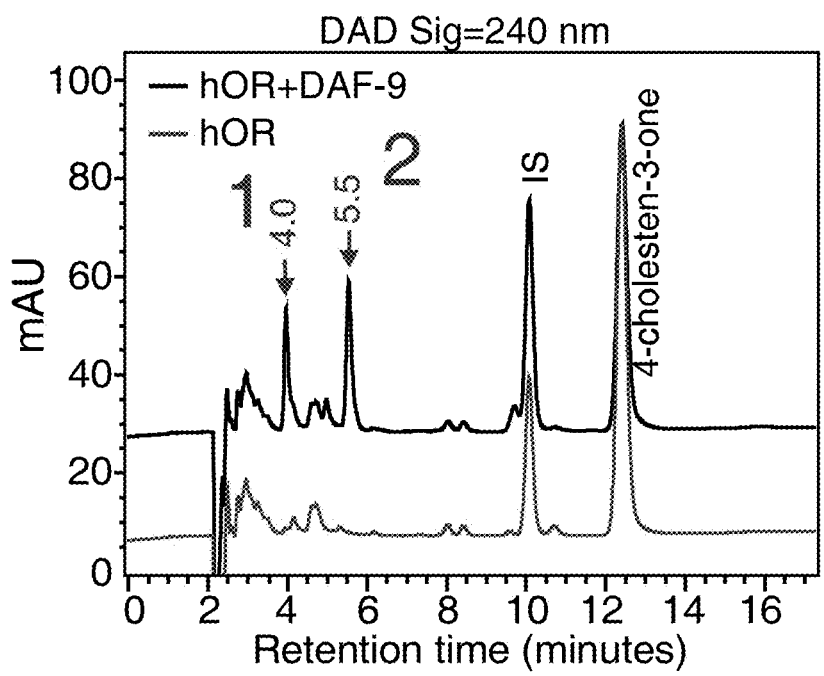
FIG. 2 (A) shows representative UV chromatogram of 4-cholesten-3-one and (B) shows reconstructed total-ion-current chromatogram of lathosterone after incubation of 100 μM substrate with DAF-9 (upper line) or control (lower line) microsomes. Product peaks unique to DAF-9 and their retention times are indicated by the arrows. IS, internal standard of 1,4-cholestadien-3-one.
Figure 2B:
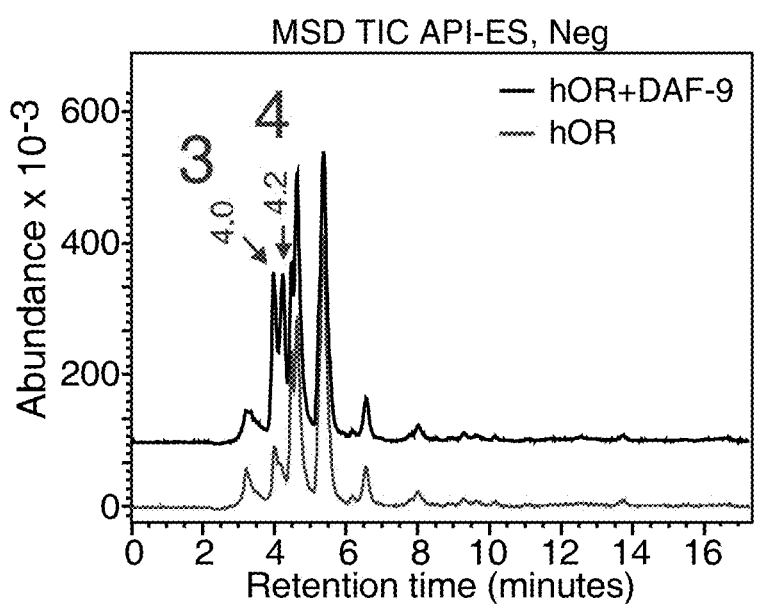
Figure 2C:
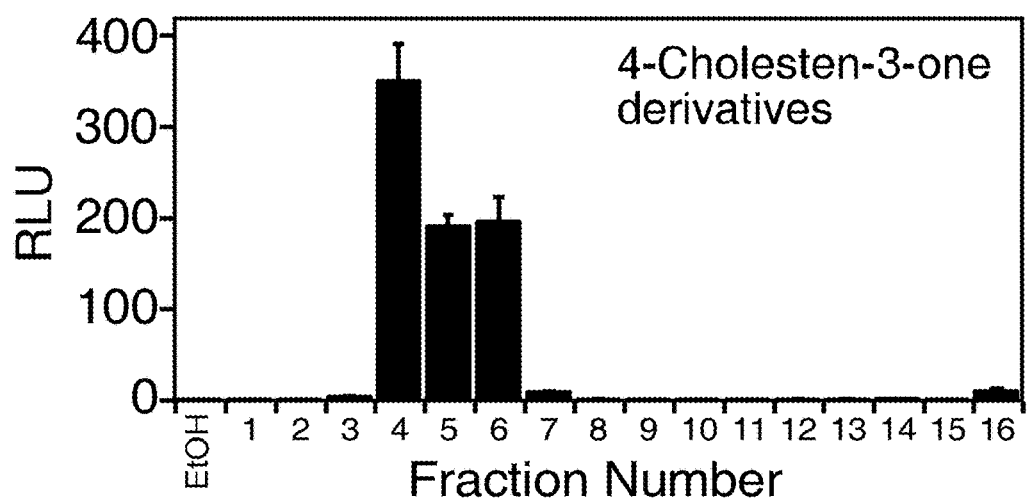
Figure 2D:
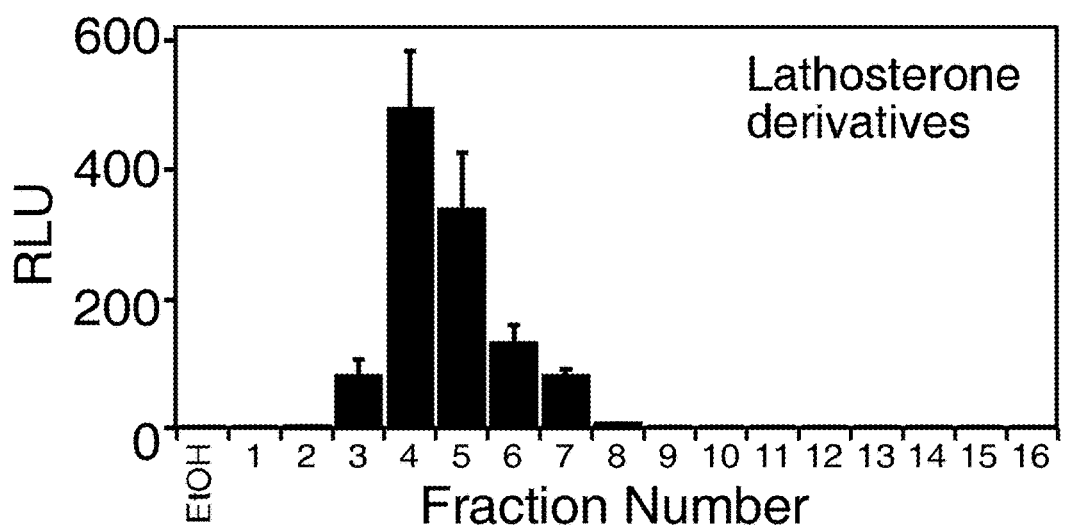
Figure 2E:
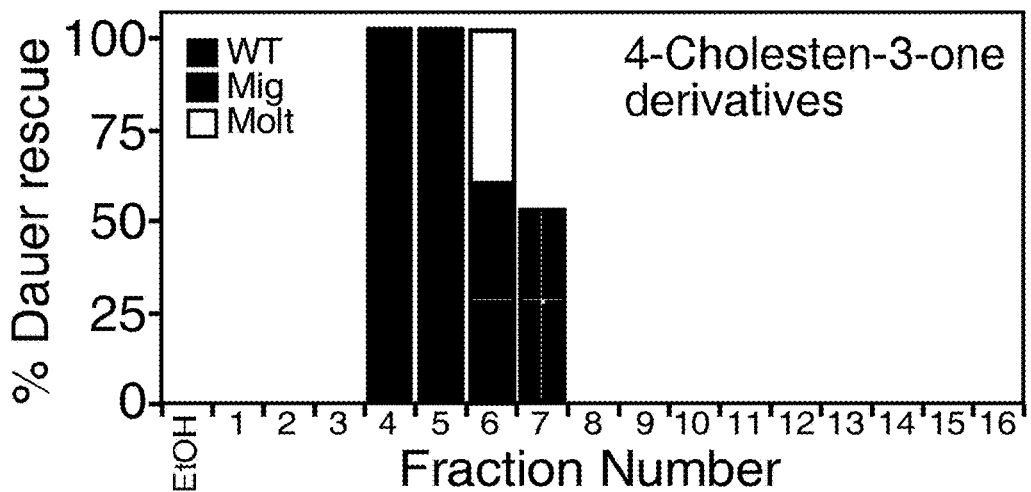
Figure 2F:
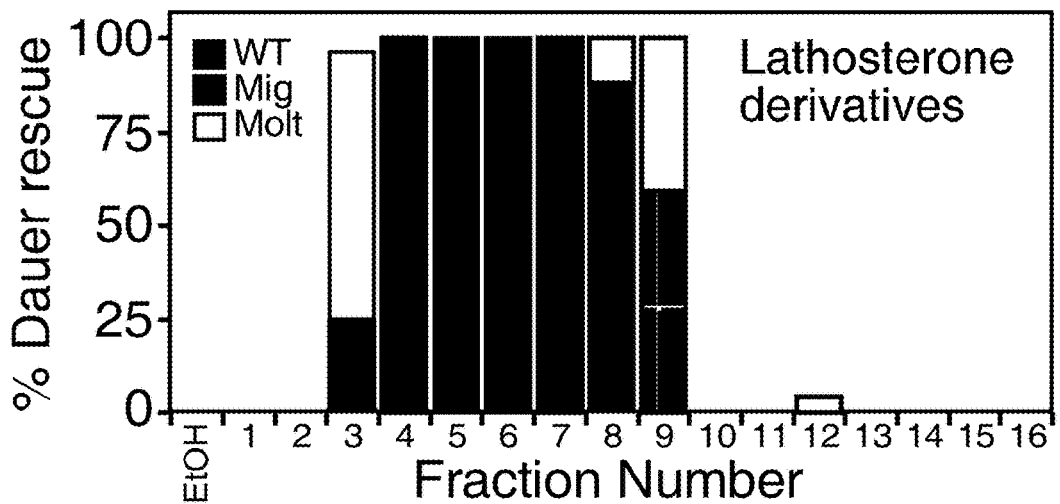

The data above suggested that DAF-9 has enzymatic activity that metabolizes 4-cholesten-3-one and lathosterone into DAF-12 ligands. Although the absolute potency of these DAF-9 metabolites could not be determined using the rescue assay, dose response curves from the co-transfection assay revealed that lathosterone metabolites were either significantly more potent or more abundantly produced than 4-cholesten-3-one metabolites (FIG. 1E). DAF-9 metabolites were identified with liquid chromatography/mass spectrometry (LC/MS). The 3-keto-$\Delta^4$-enone structure present in 4-cholesten-3-one has significant UV absorbance at 240 nm, permitting detection of the metabolites. Incubation of 4-cholesten-3-one with DAF-9 microsomes yielded two new peaks at 240 nm that were not present in the control microsomes (FIG. 2A). These metabolites eluted at 4.0 (peak 1) and 5.5 (peak 2) minutes on a reverse phase $C_{18}$ column, indicating they were oxygenated derivatives of 4-cholesten-3-one which elutes at 13 min (FIG. 2A). Since lathosterone is not UV active, its DAF-9 metabolites were scanned in negative ion mode revealing two peaks that were not present in the control microsome reactions. DAF-9 metabolites of lathosterone eluted much earlier than lathosterone at 4.0 and 4.2 minutes (peaks 3 and 4), analogous to the pattern seen for 4-cholesten-3-one (FIG. 2B). Fractions from DAF-9 microsomal reactions subjected to reverse phase-HPLC were also tested for DAF-12 activation and rescue of daf-9 null animals (FIG. 2C-F). Fractions corresponding to peaks 1-4 (i.e., the 4-cholesten-3-one and lathosterone metabolites) activated DAF-12 several hundred-fold independent of DAF-9 (FIGS. 2C and D) and rescued daf-9 null animals (FIGS. 2E and F). Interestingly, the lathosterone metabolites were stronger at activating DAF-12 and rescuing daf-9, suggesting these metabolites may be more potent.

Figure 2G:
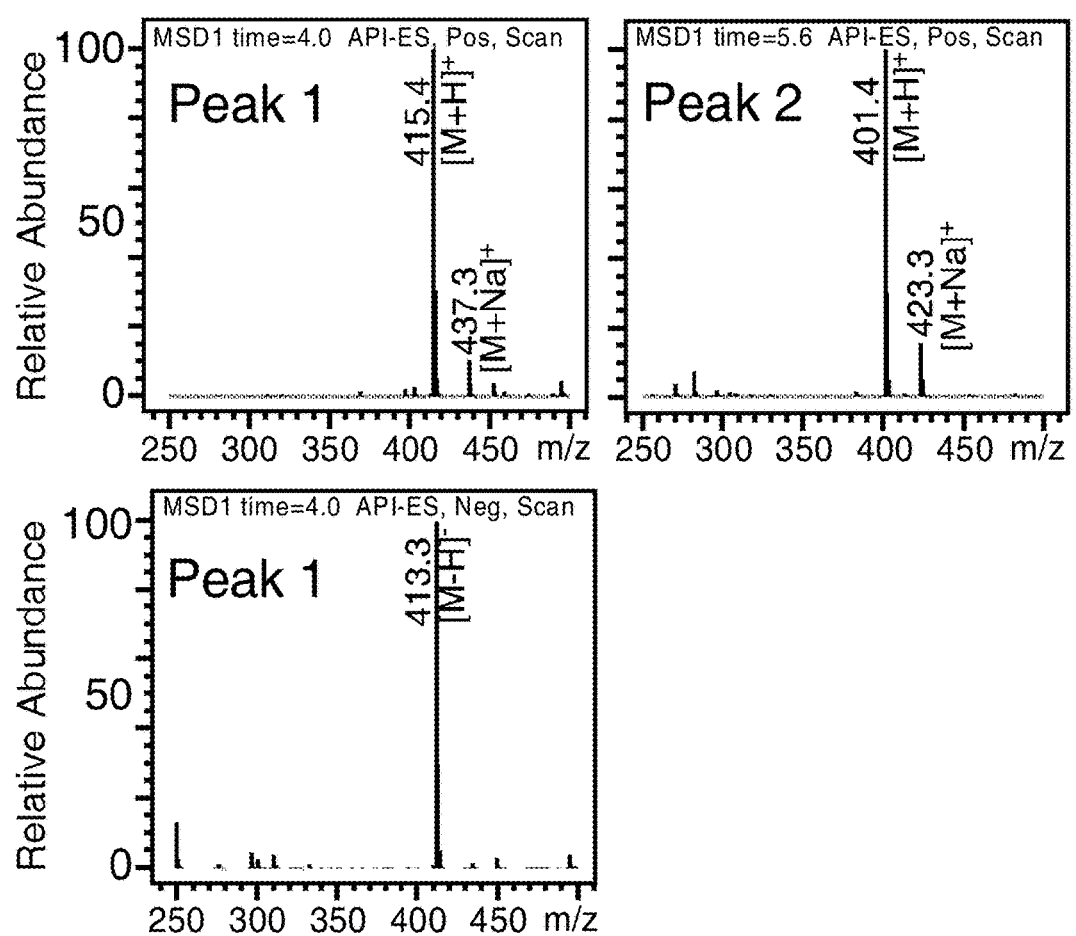
Figure 2H:
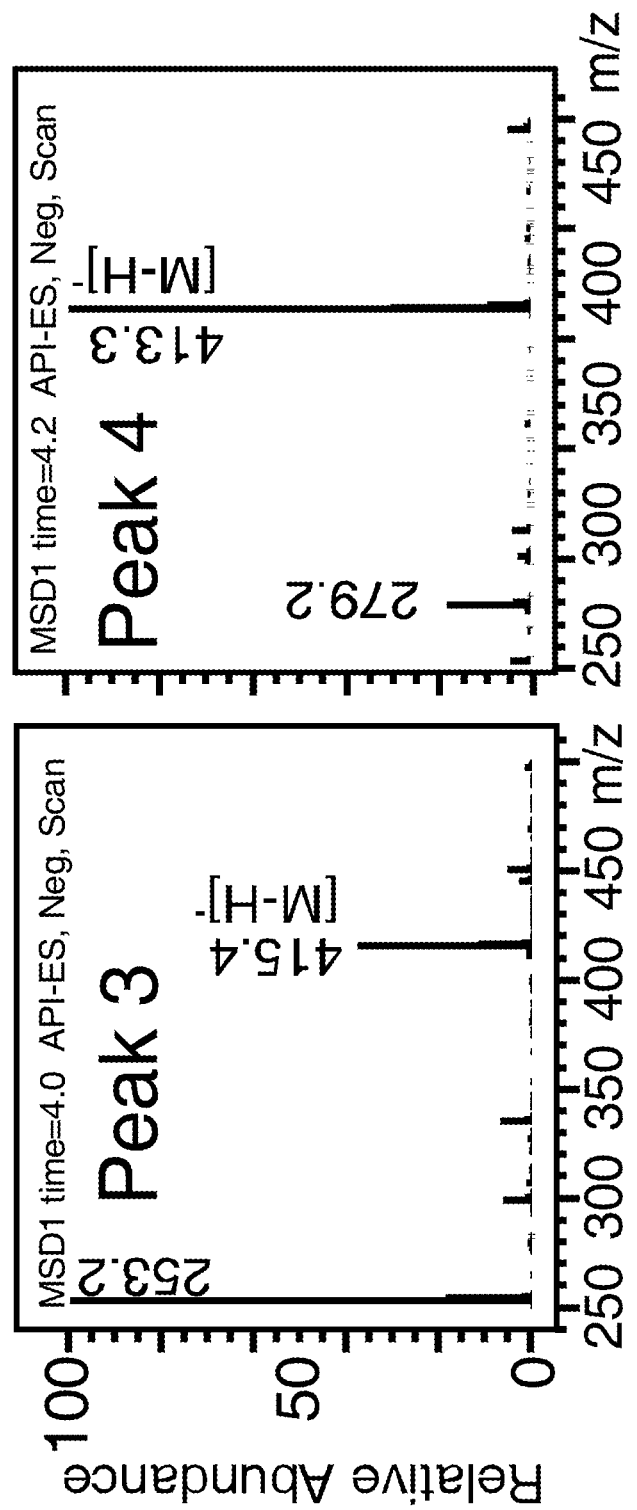

Next, LC/MS was used as a first step in the identification of the activities in peaks 1-4. Based on the molecular weight of 4-cholesten-3-one ([M+H]$^+$ m/z=385) and the retention times and mass spectra of the new metabolites, peak 2 is consistent with a mono-hydroxylated derivative of 4-cholesten-3-one ([M+H]$^+$ m/z=401) and peak 1 is consistent with a carboxylic acid derivative ([M+H]$^+$ m/z=415) (FIG. 2G). Further evidence that peak 1 represented a carboxylic acid metabolite was found after a negative ion scan in which a unique peak at 4.0 min was found only in the DAF-9 microsomes with a base peak at m/z 413 (FIG. 2G). Peak 4, which was scanned in negative ion mode, yielded similar mass spectra to peak 1, consistent with the conclusion that peak 4 is the carboxylic acid derivative of lathosterone (FIG. 2H). Finally, peak 3 contained one DAF-9 specific metabolite at m/z 415 (FIG. 2H). Although the identity of this peak remains unknown, the observed activity tracks predominantly with peak 4 and not peak 3.

DAF-9 is a 3-Keto-sterol-26-monooxygenase

Figure 3B:
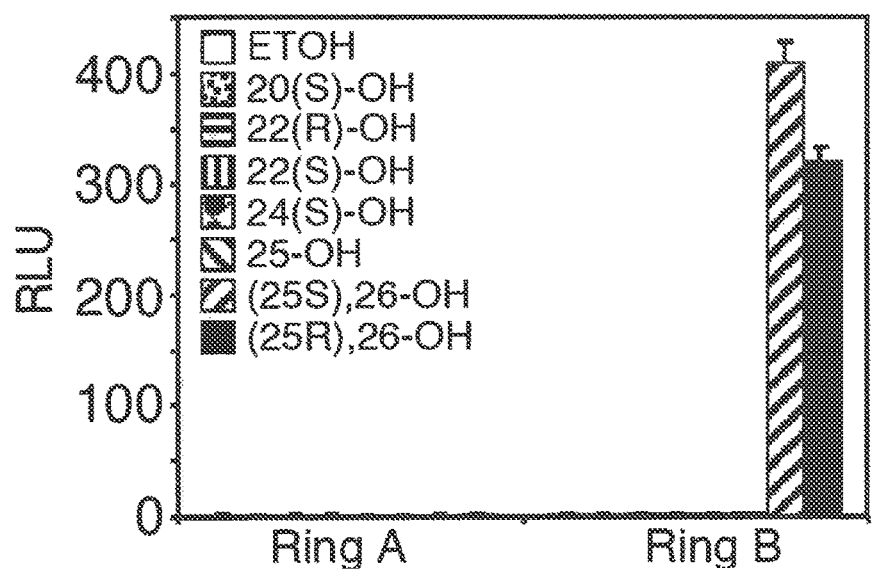
FIG. 3 (A) shows side chain substitutions of 5-cholesten-3β-ol (Ring A or delta-5) and 4-cholesten-3-one (Ring B or delta-4) derivatives.
Figure 3C:
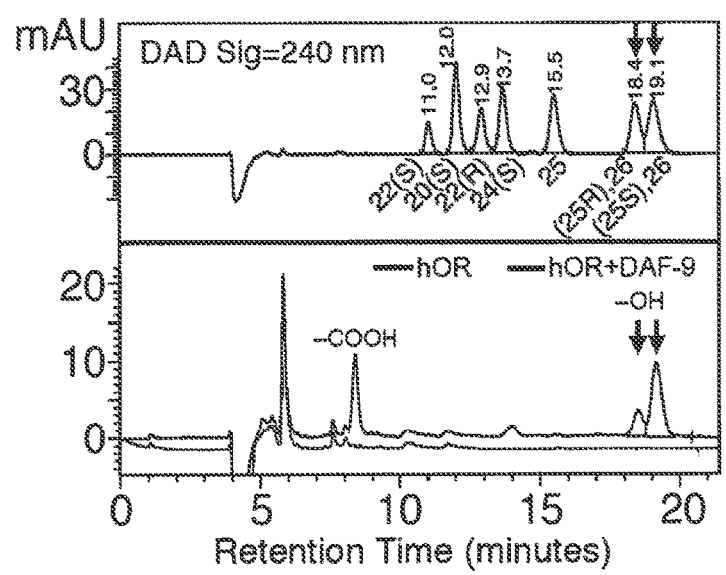

The finding that 3K-LCA was a weak activator of DAF-12 suggested that the position of oxidation of DAF-9 metabolites was on the side-chain. The commercial availability of monohydroxylated derivatives of cholesterol permitted us to focus on defining the site of oxidation on the 4-cholesten-3-one metabolites of DAF-9. A panel of side-chain oxidized 4-cholesten-3-one derivatives was generated by converting 5-cholesten-3β-ol (Ring A, 3β-hydroxy-$\Delta^5$) oxysterols (20 (S)—OH—, 22(R)—OH—, 22(S)—OH—, 24-OH—, 25-OH—, (25R),26-OH—, and (25S),26-OH-cholesterol) into their respective 4-cholesten-3-one (Ring B, 3-keto-$\Delta^4$) oxysterols using cholesterol oxidase (FIG. 3A). Generation of 4-cholesten-3-one oxysterols was confirmed by MS ([M+H]+m/z 401) and UV spectra (240 nm). When tested in the co-transfection assay independent of DAF-9, two diastereomers of 26-hydroxy-4-cholesten-3-one ((25S),26-hydroxy-4-cholesten-3-one and (25R),26-hydroxy-4-cholesten-3-one) were strongly active (FIG. 3B). In contrast, the corresponding Ring A oxysterols were inactive, confirming the idea that DAF-12 ligands require a 3-keto group. Chromatographic separation of the Ring B oxysterol panel and comparison to the 4-cholesten-3-one metabolites of DAF-9 resolved peak 2 into two peaks that co-eluted with the diastereomers of 26-hydroxy-4-cholesten-3-one (FIG. 3C). These results revealed that DAF-9 is a non-stereoselective 4-cholesten-3-one 26-hydroxylase.

Figure 3D:
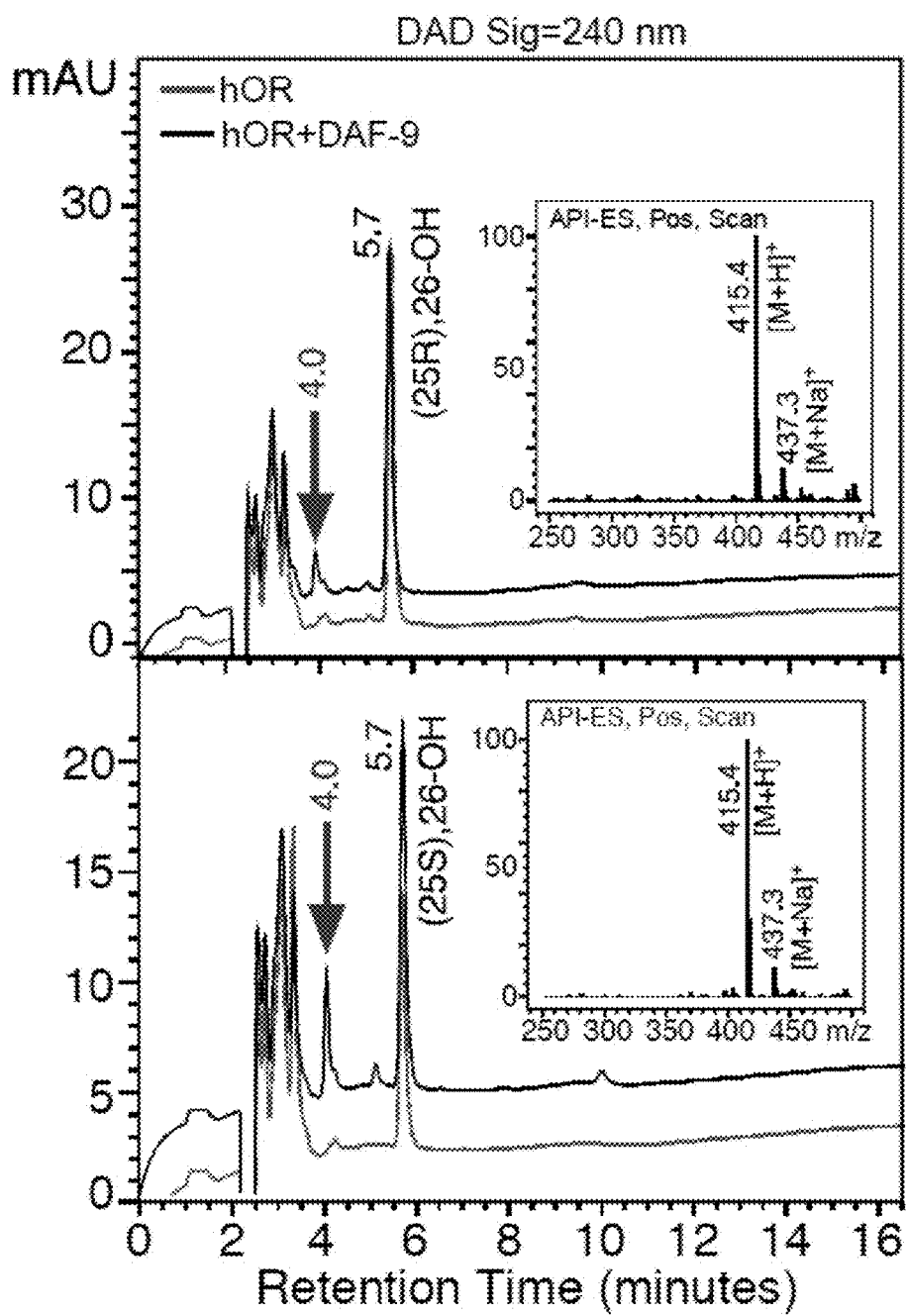
Figure 3E:
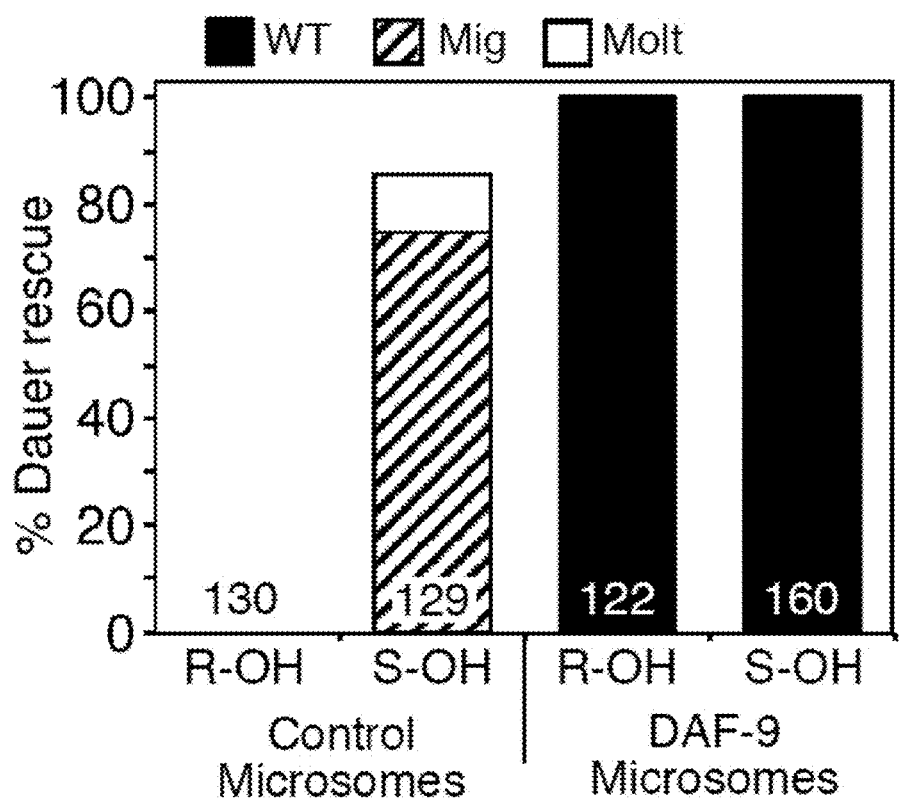

Given that DAF-9 microsomes produced both hydroxylated and carboxylated metabolites of 4-cholesten-3-one, the possibility that DAF-9 oxidizes 4-cholesten-3-one at C-26 to produce both diastereomers of 26-hydroxy-4-cholesten-3-one and then subsequently oxidizes them again into carboxylic acids was investigated. Indeed, incubation of either (25S) or (25R),26-hydroxy-4-cholesten-3-one with DAF-9 microsomes resulted in the production of a single major UV active peak with 4 min retention times and mass spectra at m/z 415 in positive ion mode (FIG. 3D). These retention times and mass spectral properties were identical to the carboxylated metabolite found after incubation 4-cholesten-3-one with DAF-9 microsomes (FIG. 2A, peak 1) and were not detected in control microsomal reactions (FIG. 3D). Conversion of the diastereomers of 26-hydroxy-4-cholesten-3-one into their C-26 carboxylic acids required a 3-keto-$\Delta^4$ structure as the 3β-hydroxy-$\Delta^5$-sterols, (25R),26-hydroxycholesterol and (25S),26-hydroxycholesterol, were not oxidized into their carboxylated metabolites. Finally, incubation of either diastereomer of 26-hydroxy-4-cholesten-3-one with DAF-9 dramatically increased their ability to rescue daf-9 phenotypes. Extracts from control microsome incubations with (25R),26-hydroxy-4-cholesten-3-one had no biological effect, while (25S),26-hydroxy-4-cholesten-3-one produced only an incomplete rescue (10% molt defects, 75% sterile Mig adults), resembling the activity in peak 2 of FIG. 2A (FIG. 3E). In contrast, incubation of either sterol with DAF-9 microsomes resulted in complete rescue of Daf-c and Mig phenotypes in 100% of animals tested (FIG. 3E). Taken together, these results demonstrated that DAF-9 metabolizes 4-cholesten-3-one into daf-9 rescuing activities through successive oxygenations at C-26, resulting in the production of carboxylic acid metabolites.

DAF-9 and Mammalian CYP27A1 are Functional Orthologs

Figure 8:
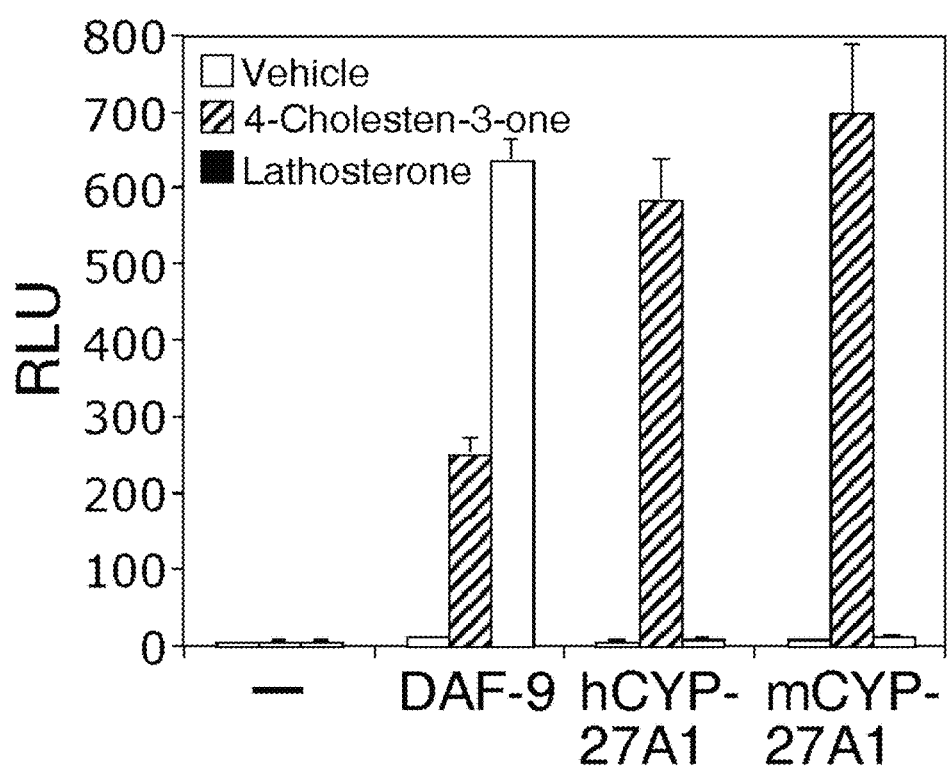
FIG. 8. HEK293 cells were co-transfected with GAL4-DAF-12, tk-MH100x4-Luc, bovine adrenodoxin, and the indicated P450 expression plasmids or empty expression vector (solid line). 4-Cholesten-3-one and lathosterone were added at 25 μM and activation was compared to vehicle control (n=3±SD).

Successive oxidation of sterol side chains has been demonstrated for the mammalian cytochrome P450, CYP27A1. Like DAF-9, CYP27A1 successively oxidizes sterol substrates at C-26 to produce both a (25R),26-hydroxy metabolite (e.g., 27-hydroxycholesterol) and (25R),26-carboxylic acid metabolite (e.g., cholestenoic acid) (Cali and Russell, 1991). Notably, in vitro studies have shown that CYP27A1 utilizes 4-cholesten-3-one more efficiently than cholesterol (Norlin et al., 2003). Therefore, the ability of CYP27A1 to metabolize 4-cholesten-3-one into a DAF-12 activator was tested. Co-transfection of HEK293 cells with GAL4-DAF-12, human or mouse CYP27A1, and bovine adrenodoxin resulted in potent activation of the GAL4-DAF-12 (FIG. 8). In contrast, DAF-12 was not activated by 4-cholesten-3-one in the presence of bovine adrenodoxin alone. Interestingly, in the presence of 25 μM lathosterone, co-transfection of CYP27A1 had no effect. These results revealed that DAF-9 and CYP27A1 have similar enzymatic activities and overlapping, but distinct, substrate specificities.

3-Keto-4-cholestenoic Acid is a Hormonal Activator of DAF-12

Figure 9:
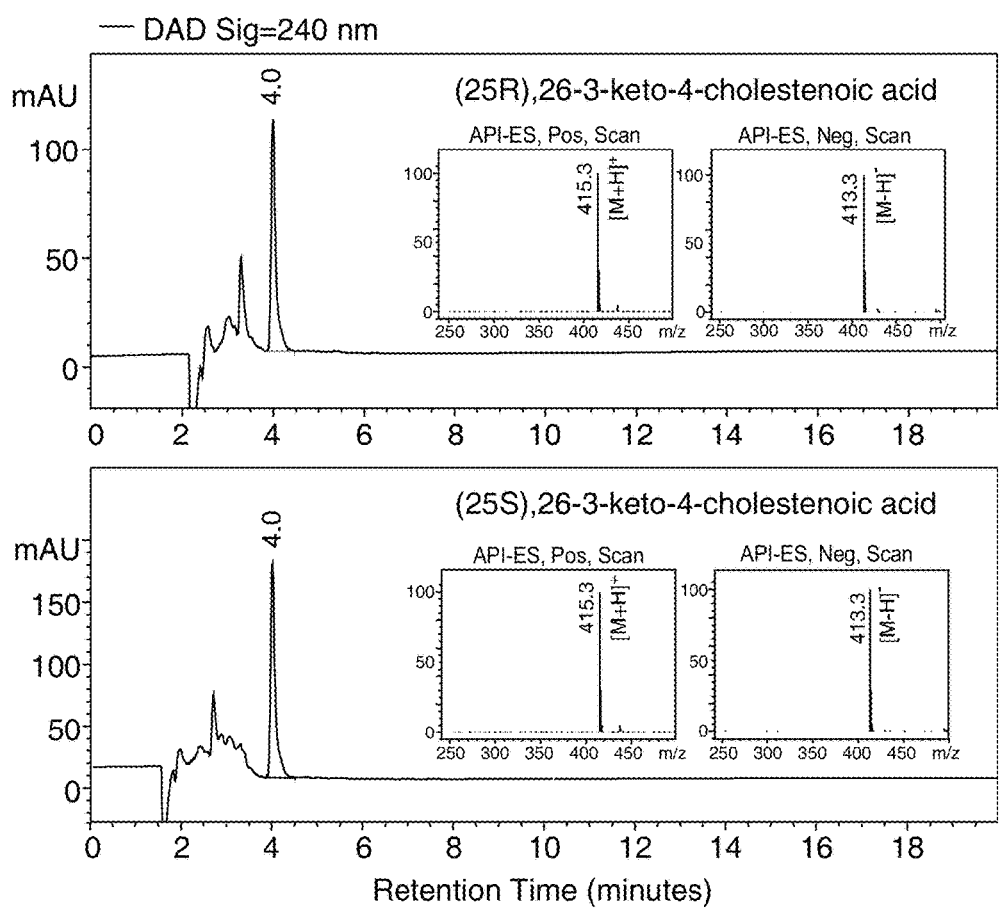
FIG. 9 shows UV chromatogram and mass spectra of 3-keto-4-cholestenoic acid.

To confirm the identity of the most potent DAF-9 metabolites as C-26 carboxylic acids of 4-cholesten-3-one (i.e., 3-keto-4-cholestenoic acid), the diastereomers of 3-keto-4-cholestenoic acid (FIG. 4A) was synthesized and tested along with the diastereomers of 26-hydroxy-4-cholesten-3-one, to transactivate DAF-12. The synthetic compounds exhibited chromatographic and mass spectral properties identical to the acidic metabolites obtained from incubation of 4-cholesten-3-one with DAF-9 microsomes (FIG. 9). When tested in the co-transfection assay, DAF-12 responded to all 4 steroids with the following rank order of potencies: (25S),26-3-keto-4-cholestenoic acid (EC50=100 nM); (25R),26-3-keto-4-cholestenoic acid (EC50=1 μM); (25S), 26-hydroxy-4-cholesten-3-one (EC50=1 μM); (25R),26-hydroxy-4-cholesten-3-one (EC50=2 μM) (FIG. 4B). Activation by (25S),26-3-keto-4-cholestenoic acid was specific to DAF-12 and not observed with other nuclear receptors tested, including the closest C. elegans, Drosophila, and human homologs (FIG. 10). In addition, the DAF-12 ligand binding domain mutants (R564C, R564H) were dramatically attenuated in their response to (25S),26-3-keto-4-cholestenoic acid (FIG. 10) and did not respond to (25R),26-3-keto-4-cholestenoic acid.

Figure 4A:
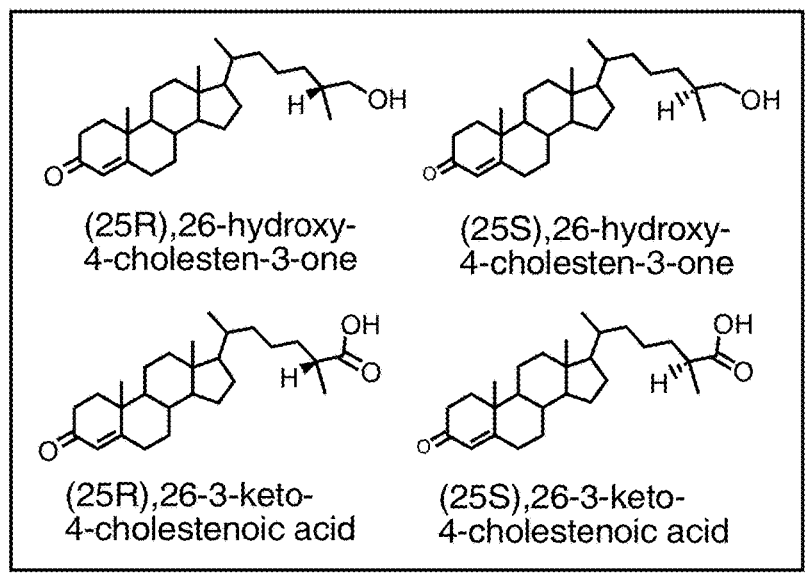
FIG. 4 (A) shows structures of 4-cholesten-3-one metabolites of DAF-9
Figure 4B:
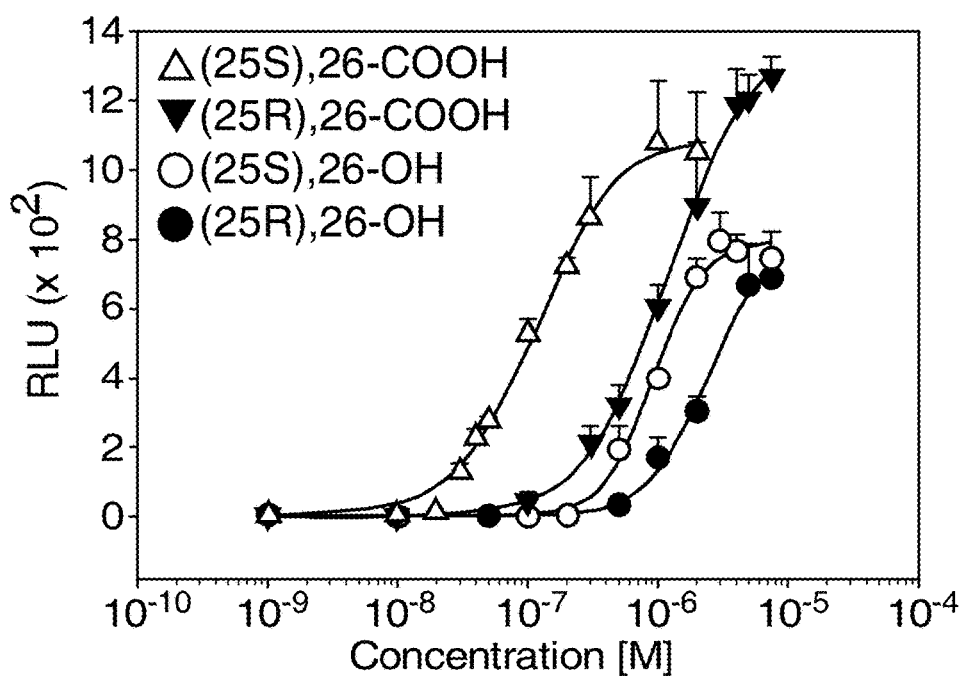
Figure 4C:
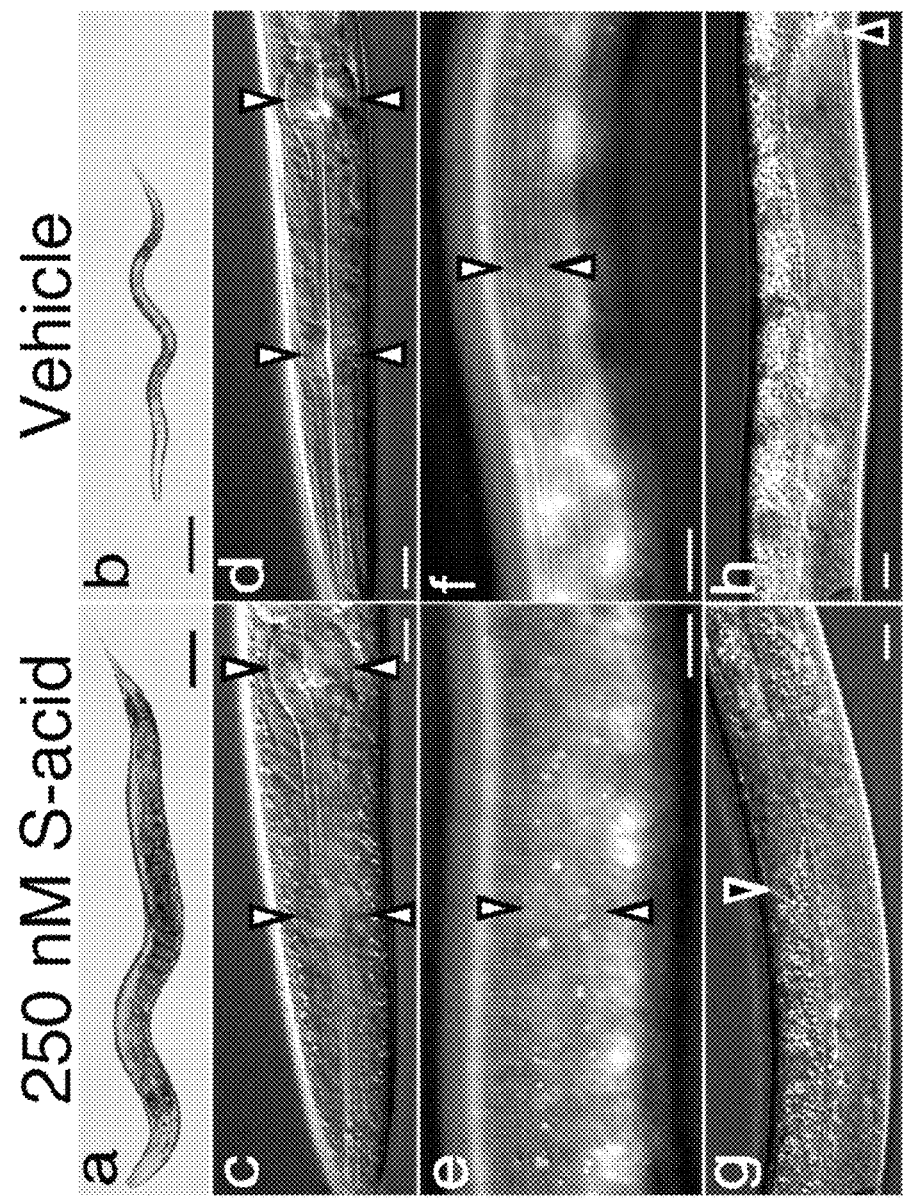
Figure 4D:
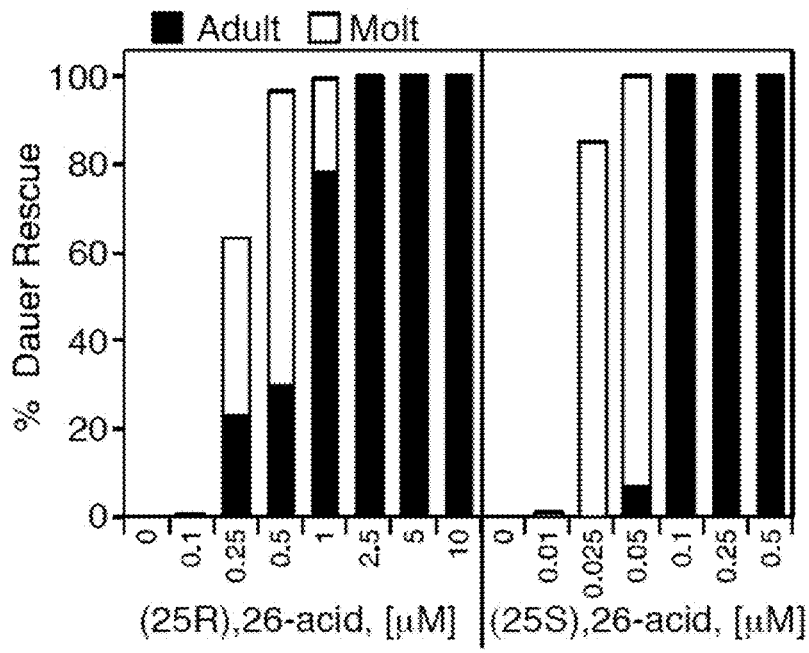
Figure 4E:
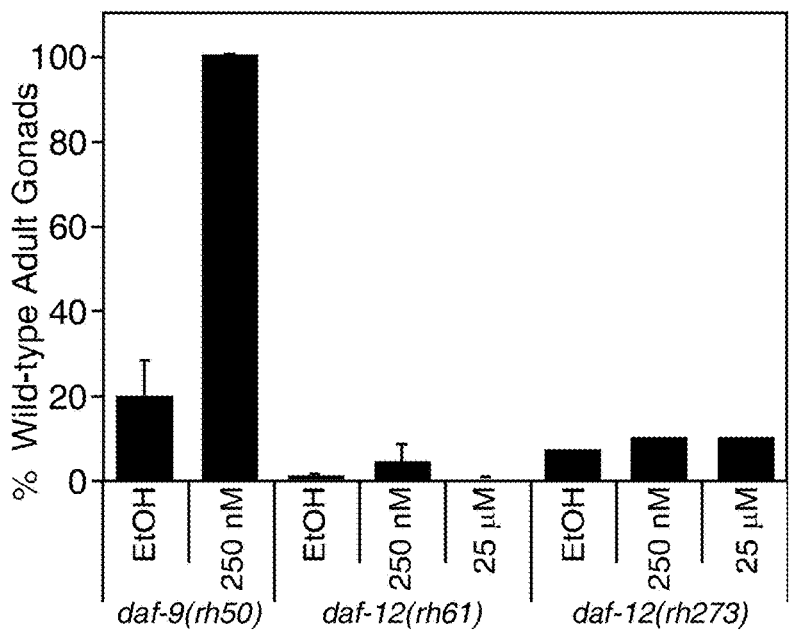

Consistent with its function as a DAF-12 hormonal ligand, (25S),26-3-keto-4-cholestenoic acid rescued Daf-c and Mig daf-9 phenotypes (FIGS. 4C and D). At hormone concentrations of 250 nM, daf-9 animals were indistinguishable from wild type: they bypassed dauer diapause to become reproductive adults (FIGS. 4C and D), and produced broods comparable to wild type (~300 offspring, n=5 worms). Rescued animals also exhibited properly turned gonads, lacked dauer alae, and displayed normal pharyngeal expansion (FIG. 4C). When placed on plates seeded without hormone, animals produced all dauer progeny, confirming their genotype as daf-9 null and demonstrating a lack of maternal rescue. Similarly, the Mig phenotype of the weak allele daf-9(rh50) was reversed at 250 nM hormone (FIG. 4E). At intermediate concentrations (50-100 nM), a proportion of null mutants exhibited Mig and molting defects, suggesting these phenotypes arise from a reduction in hormone levels (FIG. 4D). The 25R diastereomer of 3-keto-4-cholestenoic acid also rescued daf-9 phenotypes, albeit at roughly 5-10-fold higher concentrations (FIG. 4D). Consistent with the data above (FIG. 3E), (25R),26-hydroxy-4-cholesten-3-one had no effect on daf-9 nulls, even at concentrations as high as 33 μM, while (25S),26-hydroxy-4-cholesten-3-one caused 93% of worms (n>60) to bypass dauer, but still exhibit Mig and/or molting defects, and sterility. These results revealed that 3-keto-4-cholestenoic acid functions as a C. elegans hormone that inhibits dauer formation and promotes reproductive development.

As predicted by co-transfection assays (FIG. 10), daf-12 LBD mutants were compromised in their ability to respond to (25S),26-3-keto-4-cholestenoic acid (FIG. 4E). For example, hormone had no effect on daf-12(rh61), which truncates the receptor ligand binding domain and results in strong Mig phenotypes (FIG. 4E). Another mutant, daf-12 (rh273) contains a missense lesion in a predicted ligand contact site, and gives Daf-c, Mig, and molting defects. Interestingly, at ≥250 nM (25S),26-3-keto-4-cholestenoic acid, Daf-c but not Mig or molt phenotypes were rescued (FIGS. 4E and F), consistent with the conclusion that this mutation decreases ligand binding affinity.

Figure 4F:
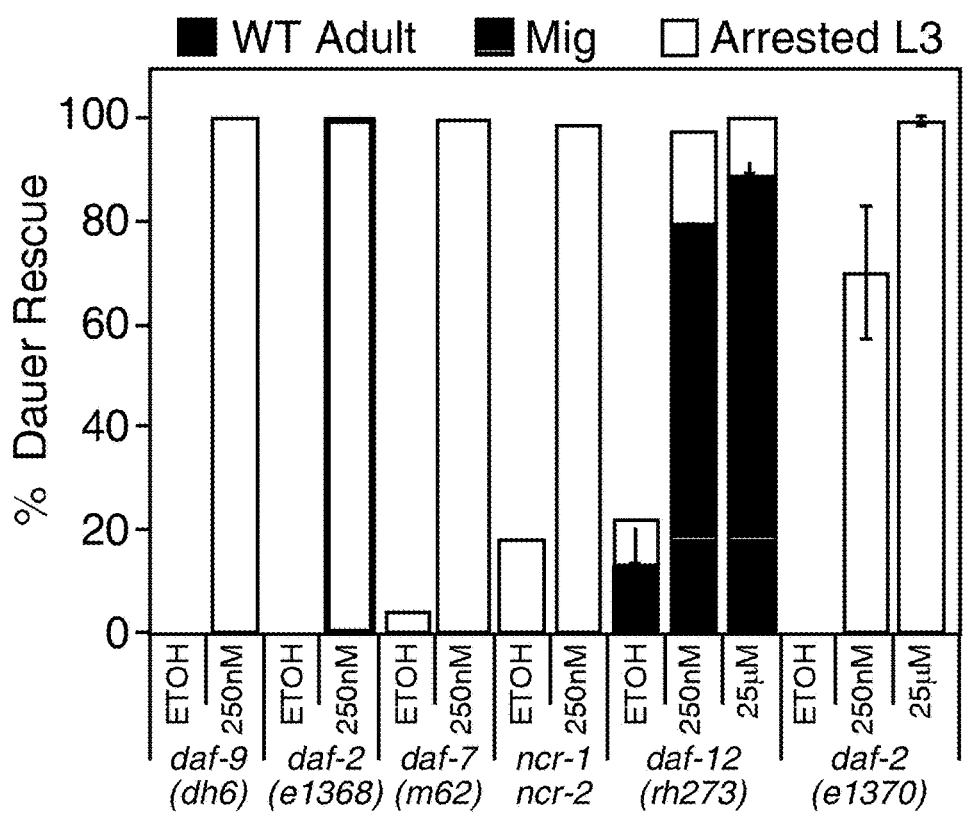

3-Keto-4-cholestenoic Acid Acts Downstream of Insulin, TGFβ, and Cholesterol Lysosomal Transport Pathways To investigate further the biological activity of 3-keto-4-cholestenoic acid the ability of (25S),26-3-keto-4-cholestenoic acid to rescue the dauer constitutive phenotypes of worms carrying mutations in the insulin-like receptor and TGFβ signaling genes positioned upstream of daf-9 and daf-12 was tested. Accordingly, it was found that (25S),26-3-keto-4-cholestenoic acid rescued the Daf-c phenotypes of daf-7(m62)/TGFβ peptide and daf-2/insulin-like receptor mutants (FIG. 4F). Whereas weak daf-2(e1368) mutants responded similar to daf-9 by bypassing dauer diapause and becoming gravid adults, the strong daf-2(e1370) mutants circumvented dauer morphogenesis but remained developmentally arrested as dark L3-like larvae, even at the highest concentrations. These results imply that insulin/IGF signaling must impinge upon the pathway both upstream, downstream, or parallel to hormone production. Finally, (25S), 26-3-keto-4-cholestenoic acid effectively rescued the Daf-c phenotypes of ncr-1;ncr-2 double mutants (FIG. 4F), which encode homologs of the human Niemann-Pick type C1 lysosomal transport protein involved in sterol transport (Li et al., 2004).

3-Keto-4-cholestenoic Acid Binds DAF-12 as a Bona Fide Ligand

A hallmark of nuclear receptor agonists is their ability to diametrically regulate interactions with co-repressors and co-activators. DIN-1S, a homolog of the mammalian co-repressor, SHARP, is thought to function as a DAF-12 co-repressor in the absence of ligand and thereby repress target genes that promote reproduction (Ludewig et al., 2004). To test this hypothesis, a mammalian two-hybrid assay was designed. In the absence of ligand, GAL4-DIN-1S interacted with VP16-DAF-12 as predicted (FIG. 5A). This interaction was completely abolished by addition of 1 µM (25S),26-3-keto-4-cholestenoic acid, supporting the conclusion that the hormone disrupts dauer-promoting complexes involving DAF-12 and DIN-1S. Importantly, hormone did not disrupt the interaction between GAL4-DIN-1S and a VP16-DAF-12 protein carrying the R564C mutation (FIG. 5A). Likewise, it was observed that DIN-1S-dependent repression of GAL4-DAF-12 basal activity could be reversed by addition of 100 nM (25S),26-3-keto-4-cholestenoic acid (FIG. 5B). A similar two-hybrid analysis was used to show hormone-dependent recruitment of co-activator to DAF-12. (25S),26-3-Keto-4-cholestenoic acid caused a ligand-dependent interaction between the fourth receptor interaction domain (ID4) of the mammalian co-activator protein SRC-1 (GAL4-SRC-1 ID4) and VP16-DAF-12, but not VP16-DAF-12-R564C (FIG. 5C). Also tested was the ability of the hormone to transactivate full-length DAF-12 on a luciferase reporter plasmid containing the DAF-12 binding sites of Lit-1 kinase, a proposed DAF-12 target gene (Shostak et al., 2004). In the presence of (25S),26-3-keto-4-cholestenoic acid, DAF-12 transactivated the Lit-1 kinase reporter plasmid in a dose-dependent manner (EC50=100 nM) (FIG. 5D).

Figure 6B:
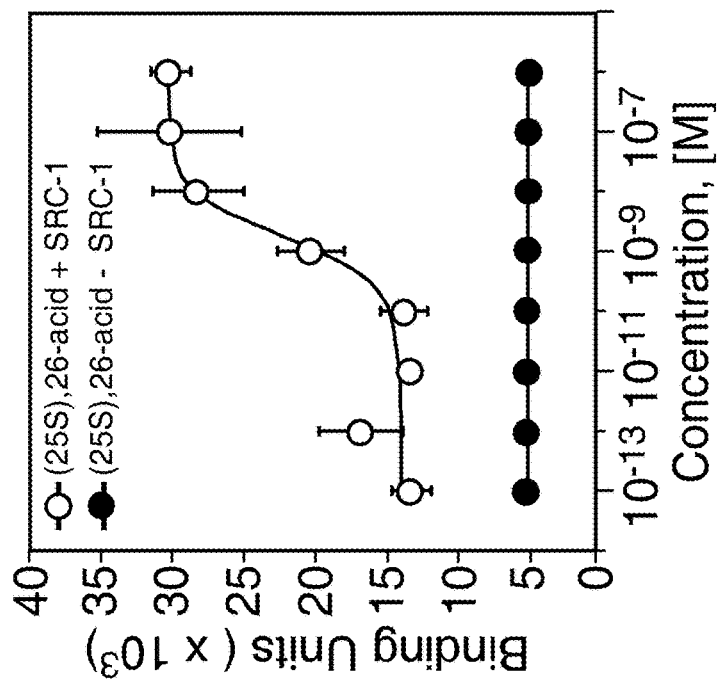
FIG. 6 (A-C) shows alpha screen assay for ligand-dependent co-activator recruitment to the DAF-12 ligand binding domain, where empty vector (CMX) or CMX VP16 were used as controls. Reactions were performed in the presence of the indicated sterols (1 μM) (A), with increasing concentrations of (25S),26-3-keto-4-cholestenoic acid (B), or with a 1:5000 dilution of DAF-9 or control microsomes incubated with 100 μM lathosterone. Results are expressed as arbitrary binding units from triplicate assays (±SD).
Figure 6A:
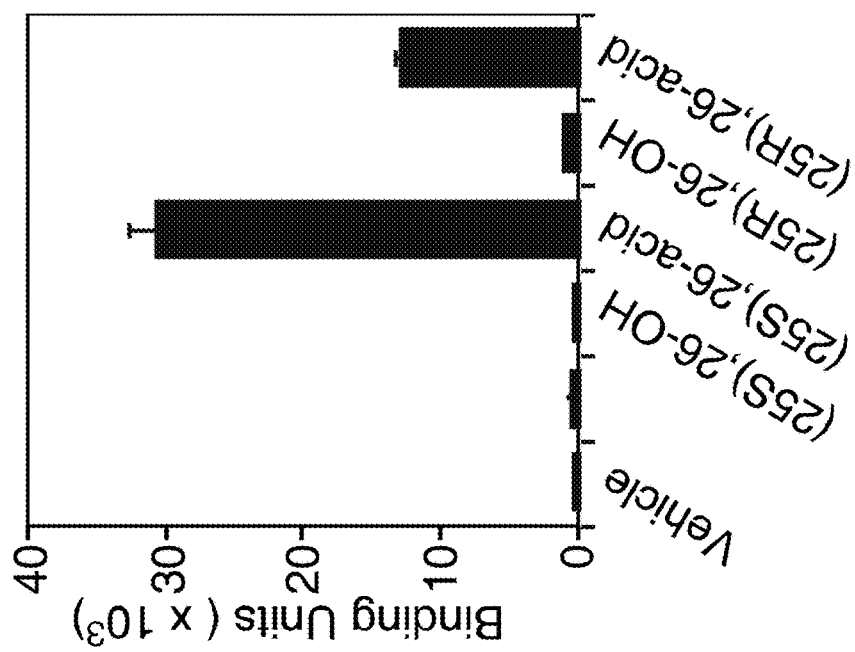
Figure 6C:
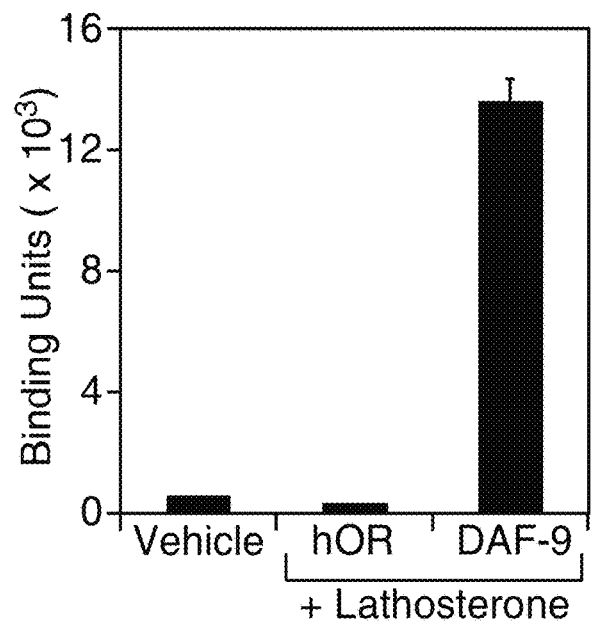
Figure 6D:
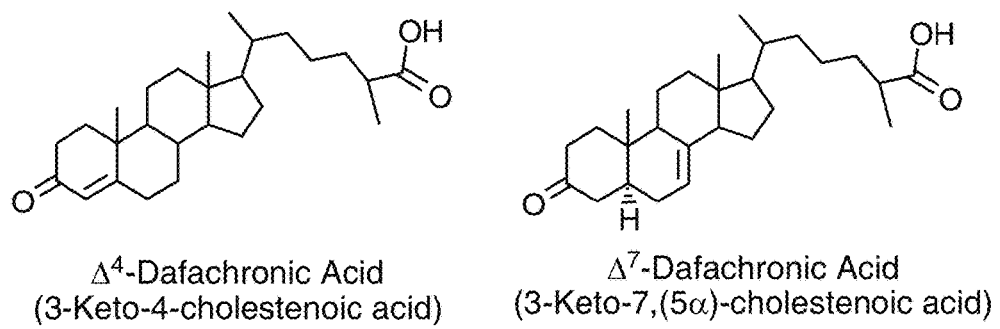

Finally, to determine the in vitro ligand binding properties of DAF-12 with the various 4-cholesten-3-one metabolites shown in FIG. 4A, an Alpha Screen assay that can detect ligand-dependent interactions between receptors and co-activator peptides was employed (Xu et al., 2002). At 1 µM, the (25S) and (25R),26-3-keto-4-cholestenoic acids produced 58-fold and 24-fold increases in binding units, respectively, compared to vehicle control (FIG. 6A). In contrast, the hormone precursor, 4-cholesten-3-one, and the hydroxyl intermediate, (25S),26-hydroxy-4-cholesten-3-one, showed no significant binding. Weak binding activity (2-fold) was detected for the weaker activating diastereomer, (25R),26-hydroxy-4-cholesten-3-one. Saturation binding kinetics revealed that (25S),26-3-keto-4-cholestenoic acid binds DAF-12 with high affinity (EC50=1 nM) (FIG. 6B). A similar analysis revealed (25R),26-3-keto-4-cholestenoic acid binds DAF-12, but with at least a 10-fold lower affinity. Although the C-26 carboxylic acid derivative of lathosterone is not available, a strong ligand binding activity was detected in the DAF-9 microsomes that were incubated with lathosterone (FIG. 6C) and were shown to contain the presumed carboxylic acid metabolite (FIG. 2). These results support the conclusion that both the 3-keto-4-cholestenoic acid and lathosterone carboxylic acid hormones mediate their effects in vivo through direct binding to DAF-12.

3-Keto-4-cholestenoic Acid is an Endogenous *C. elegans* Hormone

Figure 7:
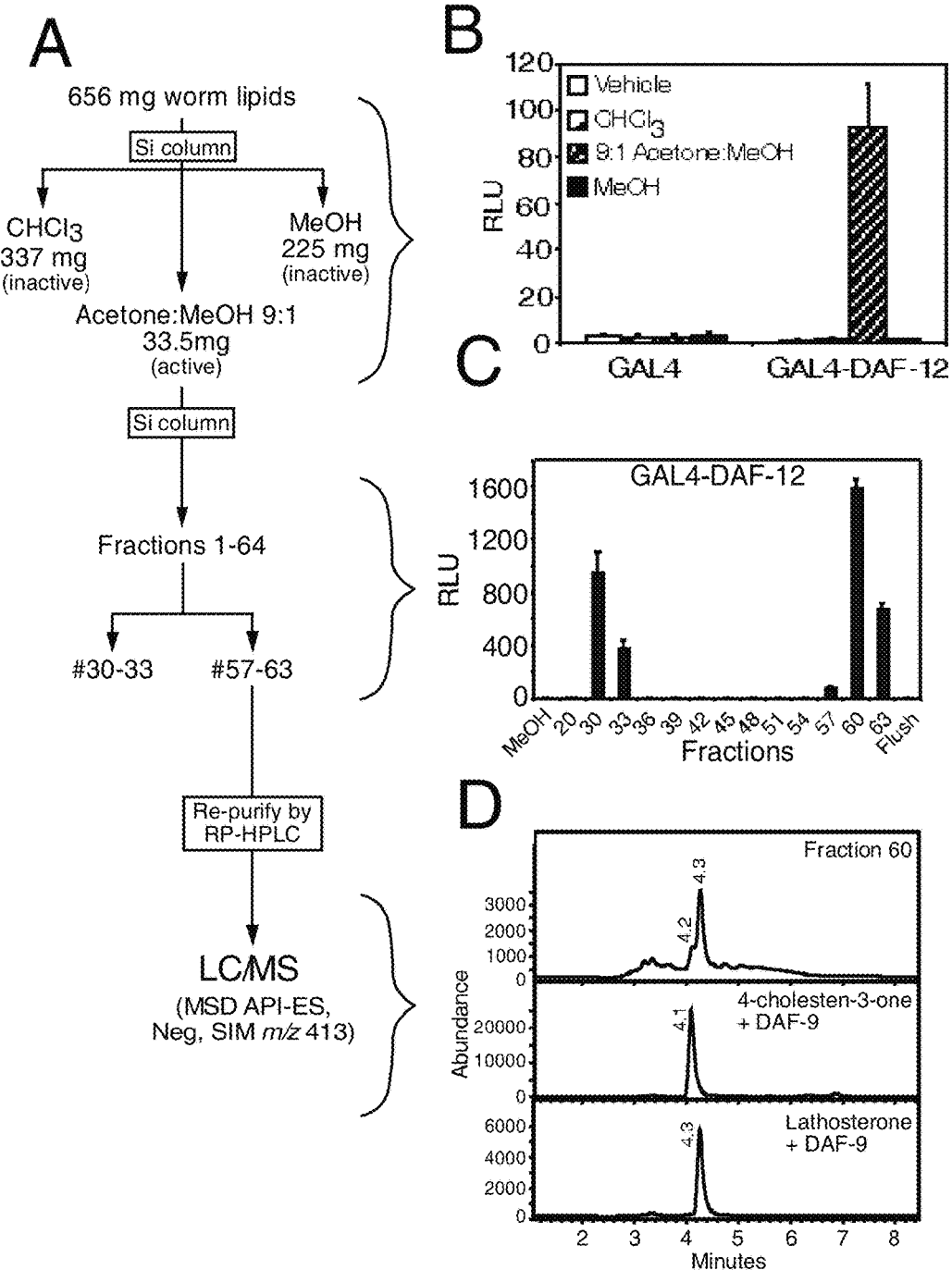
FIG. 7 (A) shows a strategy for purifying endogenous DAF-12 agonists from C. elegans lipid extracts.

To determine whether the DAF-12 ligands identified above are present in vivo, lipid extracts from L3-L4 staged worms were generated and tested for DAF-12 activity in a co-transfection assay. Crude extracts containing activity were fractionated by silica column chromatography (FIG. 7A) and the DAF-12 activating fraction was determined to be in the acetone:methanol eluate (FIG. 7B). Subsequent fractionation of this activity revealed the presence of two distinct DAF-12 activity peaks at fractions 30-33 and 57-63 (FIG. 7C). Although the level of activity in fraction 30-33 was too low for further analysis, its chromatographic properties were consistent with the alcohol derivatives of 4-cholesten-3-one and lathosterone. After pooling and re-purification by HPLC of fractions 57-63, however, enough material was obtained to look for the presence of the carboxylic acid derivatives by LC/MS (FIG. 7D, upper panel). Selective ion monitoring (SIM) identified a peak at m/z 413 in negative ion mode with a retention time similar to the 3-keto-4-cholestenoic acid metabolite of DAF-9 (FIG. 7D, middle panel). This signal correlated with DAF-12 activity, as it was not present in neighboring fractions that lacked activity. In addition, a second, higher abundance peak was detected that co-migrated with the carboxylic acid of lathosterone (FIG. 7D, bottom panel). As expected, lipids from these pooled fractions rescued the Daf-c and Mig phenotypes in 100% of daf-9 null worms tested (n>300).

Transactivation of *C. elegans* nuclear hormone receptor DAF-12 by (25S),26-3-keto-4-cholestenoic acid ($\Delta^4$ dafachronic S acid), 3-keto-7,(5a)-cholesten-25(R)-26-oic acid ($\Delta^7$ dafachronic R acid), and 3β-ol-5-cholesten-25(S)-26-oic acid.

HEK cells were transfected in 96 well plates with plasmids as follows: 50 ng of mh100-tk-luc reporter, 10 ng CMX-β-galactosidase reporter, 15 ng CMX-Gal4-c.eDAF-12LBD which expresses a fusion protein of Gal4 DNA-binding domain with ligand-binding domain of *C. elegans* nuclear hormone receptor DAF-12. Indicated dose of ligands were added 6 hours later and luciferase as well as β-galactosidase activities were measured 24 hours after transfection. Relative luciferase unit (RLU) was then calculated by normalizing the luciferase activity to the β-galactosidase control. The transactivation of the nuclear hormone receptor was represented by fold change of RLU induced by treatment of indicated concentration of ligands. Data represent the mean±S.D. of triplicate assays (FIG. 12).

Infections by hookworms, which are parasitic nematodes, are a major reason for anemia and growth retardation, especially in children and pregnant women. Hookworms and *C. elegans* belong to the same evolutionary clade and have many features in common. In particular, the infective L3 (iL3) larval stage, the only one during hookworm development when the parasite is able to infect a host, is similar to the dauer larval stage of *C. elegans*.

The present inventors have cloned DAF-12 homologs from three notorious hookworm species, *Necator americanus, Ancylostomiasis ceyelanicum*, and *A. caninum*. These homologs were evaluated to assess their susceptibility to activation by dafachronic acids, as well as by a structurally-related steroid analog, called "3β-5-cholestenoic acid," which is found in hookworm hosts (i.e., humans, hamsters, and dog).

As illuminated in the following examples, the data show that these compounds are able to activate all three hookworm homologs of DAF-12, thereby evidencing a conserved signaling pathway that controls the infectious and adult stages in hookworm as it does in *C. elegans*. Thus, the data underscore the targeting of these homologs as a feasible strategy for pharmacological intervention of hookworm infection, which affects over one billion people worldwide.

Transactivation of human hookworm *N. americanus* nuclear hormone receptor DAF-12 by (25S),26-3-keto-4-cholestenoic acid ($\Delta^4$ dafachronic S acid), 3-keto-7,(5a)-cholesten-25(R)-26-oic acid ($\Delta^7$ dafachronic R acid), and 3β-ol-5-cholesten-25(S)-26-oic acid.

HEK cells were transfected in 96 well plates with plasmids as follows: 50 ng of mh100-tk-luc reporter, 10 ng CMX-β-galactosidase reporter, 15 ng CMX-Gal4-n.a.DAF- 12LBD which expresses a fusion protein of Gal4 DNA-binding domain with ligand-binding domain of *N. americanus* nuclear hormone receptor DAF-12. Indicated dose of ligands were added 6 hours later and luciferase as well as β-galactosidase activities were measured 24 hours after transfection. Relative luciferase unit (RLU) was then calculated by normalizing the luciferase activity to the β-galactosidase control. The transactivation of the nuclear hormone receptor was represented by fold change of RLU induced by treatment of indicated concentration of ligands. Data represent the mean±S.D. of triplicate assays (FIG. 13).

Transactivation of human/hamster hookworm *A. ceyelanicum* nuclear hormone receptor DAF-12 by (25S),26-3-keto-4-cholestenoic acid ($\Delta^4$ dafachronic S acid), 3-keto-7,(5a)-cholesten-25(R)-26-oic acid ($\Delta^7$ dafachronic R acid), and 3β-ol-5-cholesten-25(S)-26-oic acid.

HEK cells were transfected in 96 well plates with plasmids as follows: 50 ng of mh100-tk-luc reporter, 10 ng CMX-β-galactosidase reporter, 15 ng CMX-Gal4-a.cey-DAF-12LBD which expresses a fusion protein of Gal4 DNA-binding domain with ligand-binding domain of *A. ceyelanicum* nuclear hormone receptor DAF-12. Indicated dose of ligands were added 6 hours later and luciferase as well as β-galactosidase activities were measured 24 hours after transfection. Relative luciferase unit (RLU) was then calculated by normalizing the luciferase activity to the β-galactosidase control. The transactivation of the nuclear hormone receptor was represented by fold change of RLU induced by treatment of indicated concentration of ligands. Data represent the mean±S.D. of triplicate assays (FIG. 14).

Transactivation of dog hookworm *A. caninum* nuclear hormone receptor DAF-12 by (25S),26-3-keto-4-cholestenoic acid ($\Delta^4$ dafachronic S acid), 3-keto-7,(5a)-cholesten-25(R)-26-oic acid ($\Delta^7$ dafachronic R acid), and 3β-ol-5-cholesten-25(S)-26-oic acid.

HEK cells were transfected in 96 well plates with plasmids as follows: 50 ng of mh100-tk-luc reporter, 10 ng CMX-β-galactosidase reporter, 15 ng CMX-Gal4-a.c.DAF-12LBD which expresses a fusion protein of Gal4 DNA-binding domain with ligand-binding domain of *A. caninum* nuclear hormone receptor DAF-12. Indicated dose of ligands were added 6 hours later and luciferase as well as β-galactosidase activities were measured 24 hours after transfection. Relative luciferase unit (RLU) was then calculated by normalizing the luciferase activity to the β-galactosidase control. The transactivation of the nuclear hormone receptor was represented by fold change of RLU induced by treatment of indicated concentration of ligands. Data represent the mean±S.D. of triplicate assays (FIG. 15).

* * *

This specification refers to the following publications:

Albert, P. S., and Riddle, D. L. (1988). Mutants of *Caenorhabditis elegans* that form dauer-like larvae. Dev Biol 126, 270-293.

Antebi, A., Culotti, J. G., and Hedgecock, E. M. (1998). daf-12 regulates developmental age and the dauer alternative in *Caenorhabditis elegans*. Development 125, 1191-1205.

Antebi, A., Yeh, W. H., Tait, D., Hedgecock, E. M., and Riddle, D. L. (2000). daf-12 encodes a nuclear receptor that regulates the dauer diapause and developmental age in *C. elegans*. Genes Dev 14, 1512-1527.

Brenner, S. (1974). The genetics of *Caenorhabditis elegans*. Genetics 77, 71-94.

Cali, J. J., and Russell, D. W. (1991). Characterization of human sterol 27-hydroxylase. A mitochondrial cytochrome P-450 that catalyzes multiple oxidation reaction in bile acid biosynthesis. J Biol Chem 266, 7774-7778.

Cheng, J. B., Motola, D. L., Mangelsdorf, D. J., and Russell, D. W., *De-orphanization of cytochrome P450 2R1: a microsomal vitamin D 25-hydroxilase*. J Biol Chem, 2003. 278(39): p. 38084-93.

Chitwood, D. J. (1999). Biochemistry and function of nematode steroids. Crit Rev Biochem Mol Biol 34, 273-284.

Chitwood, D. J., Lusby, W. R., Lozano, R., Thompson, M. J., and Svoboda, J. A. (1983). Novel nuclear methylation of sterols by the nematode *Caenorhabditis elegans*. Steroids 42, 311-319.

Gerisch, B., and Antebi, A. (2004). Hormonal signals produced by DAF-9/cytochrome P450 regulate *C. elegans* dauer diapause in response to environmental cues. Development 131, 1765-1776.

Gerisch, B., Weitzel, C., Kober-Eisermann, C., Rottiers, V., and Antebi, A. (2001). A hormonal signaling pathway influencing *C. elegans* metabolism, reproductive development, and life span. Dev Cell 1, 841-851.

Gill, M. S., Held, J. M., Fisher, A. L., Gibson, B. W., and Lithgow, G. J. (2004). Lipophilic regulator of a developmental switch in *Caenorhabditis elegans*. Aging Cell 3, 413-421.

Gissendanner, C. R., Crossgrove, K., Kraus, K. A., Maina, C. V., and Sluder, A. E. (2004). Expression and function of conserved nuclear receptor genes in *Caenorhabditis elegans*. Dev Biol 266, 399-416.

Haag et al., Chem. Soc. Perkin Trans. I (1988)

Hood, S. R., Shah, G., and Jones, P. (1996). Expression of Cytochromes P450 in a Baculovirus System, In Methods in Molecular Biology, I. R. Phillips and E. A. Shephard, eds. (Totowa, N.J.: Humana Press), pp. 203-217.

Hsin, H., and Kenyon, C. (1999). Signals from the reproductive system regulate the lifespan of *C. elegans*. Nature 399, 362-366.

Jia, K., Albert, P. S., and Riddle, D. L. (2002). DAF-9, a cytochrome P450 regulating *C. elegans* larval development and adult longevity. Development 129, 221-231.

Kim, H.-S., Wilson, W. K., Needleman, D. H., Pinkerton, F. D., Wilson, D. K., Quiocho, F. A., and Schroepfer, Jr., G. J. (1989). Inhibitors of sterol synthesis. Chemical synthesis, structure, and biological activities of (25R)-3 beta,26-dihydroxy-5 alpha-cholest-8(14)-en-15-one, a metabolite of 3 beta-hydroxy-5 alpha-cholest-8(14)-en-15-one Journal Lipid Research 30:247-261.

Kimura, K. D., Tissenbaum, H. A., Liu, Y., and Ruvkun, G. (1997). daf-2, an insulin receptor-like gene that regulates longevity and diapause in *Caenorhabditis elegans*. Science 277, 942-946.

Larsen, P. L., Albert, P. S., and Riddle, D. L. (1995). Genes that regulate both development and longevity in *Caenorhabditis elegans*. Genetics 139, 1567-1583.

Li, J., Brown, G., Ailion, M., Lee, S., and Thomas, J. H. (2004). NCR-1 and NCR-2, the *C. elegans* homologs of the human Niemann-Pick type C1 disease protein, function upstream of DAF-9 in the dauer formation pathways. Development 131, 5741-5752.

Lindblom, T. H., Pierce, G. J., and Sluder, A. E. (2001). A *C. elegans* orphan nuclear receptor contributes to xenobiotic resistance. Curr Biol 11, 864-868.

Ludewig, A. H., Kober-Eisermann, C., Weitzel, C., Bethke, A., Neubert, K., Gerisch, B., Hutter, H., and Antebi, A. (2004). A novel nuclear receptor/coregulator complex controls *C. elegans* lipid metabolism, larval development, and aging. Genes Dev 18, 2120-2133.

Liu et al. (1996). Drug Therapy: Antiparasitic Drugs. New England J. Med. 334, 1178-1184.

Mak, H. Y., and Ruvkun, G. (2004). Intercellular signaling of reproductive development by the *C. elegans* DAF-9 cytochrome P450. Development 131, 1777-1786.

Makishima, M., Okamoto, A. Y., Repa, J. J., Tu, H., Learned, R. M., Luk, A., Hull, M. V., Lustig, K. D., Mangelsdorf, D. J., and Shan, B. (1999). Identification of a nuclear receptor for bile acids. Science 284, 1362-1365.

Matyash, V., Entchev, E. V., Mende, F., Wilsch-Brauninger, M., Thiele, C., Schmidt, A. W., Knolker, H. J., Ward, S., and Kurzchalia, T. V. (2004). Sterol-derived hormone(s) controls entry into diapause in *Caenorhabditis elegans* by consecutive activation of DAF-12 and DAF-16. PLoS Biol 2, e280.

Merris, M., Wadsworth, W. G., Khamrai, U., Bittman, R., Chitwood, D. J., and Lenard, J. (2003). Sterol effects and sites of sterol accumulation in *Caenorhabditis elegans*: developmental requirement for 4alpha-methyl sterols. J Lipid Res 44, 172-181.

Mooijaart, S. P., Brandt, B. W., Baldal, E. A., Pijpe, J., Kuningas, M., Beekman, M., Zwaan, B. J., Slagboom, P. E., Westendorp, R. G., and van Heemst, D. (2005). *C. elegans* DAF-12, Nuclear Hormone Receptors and human longevity and disease at old age. Ageing Res Rev 4, 351-371.

Norlin, M., von Bahr, S., Bjorkhem, I., and Wikvall, K. (2003). On the substrate specificity of human CYP27A1: implications for bile acid and cholestanol formation. J Lipid Res 44, 1515-1522.

Rahier, A (2001). Biochemistry. 40, 256-267.

Ren, P., Lim, C. S., Johnsen, R., Albert, P. S., Pilgrim, D., and Riddle, D. L. (1996). Control of *C. elegans* larval development by neuronal expression of a TGF-beta homolog. Science 274, 1389-1391.

Riddle, D. L., and Albert, P. S. (1997). Genetic and environmental regulation of dauer larva development, In *C. elegans* II, D. L. Riddle, B. Meyer, J. Priess, and T. Blumenthal, eds. (Colds Spring Harbor: Cold Spring Harbor Laboratory Press), pp. 739-768.

Russell, D. W. (2003). The enzymes, regulation, and genetics of bile acid synthesis. Ann Rev Biochem 72, 137-174.

Sangster N. C., and Gill, J. (1999). Pharmacology of anthelmintic resistance. Parasitol Today 15, 141-146.

Schackwitz, W. S., Inoue, T., and Thomas, J. H. (1996). Chemosensory neurons function in parallel to mediate a pheromone response in *C. elegans*. Neuron 17, 719-728.

Shostak, Y., Van Gilst, M. R., Antebi, A., and Yamamoto, K. R. (2004). Identification of *C. elegans* DAF-12-binding sites, response elements, and target genes. Genes Dev 18, 2529-2544.

Siddiqui, A. A., Stanley, C. S., Berk, S. L., and Skelly, P. J. (2000) A cDNA encoding a nuclear hormone receptor of the steroid/thyroid hormone-receptor superfamily from the human parasitic nematode *Strongyloides stercoralis*. Parasitol. Res. 86, 24-29.

Sluder, A. E., and Maina, C. V. (2001). Nuclear receptors in nematodes: themes and variations. Trends Genet 17, 206-213.

Stiernagel, T. (1999). Maintenance of *C. elegans*, In *C. elegans*: A Practical Approach, I. A. Hope, ed. (New York: Oxford University Press), pp. 51-67.

Umesono, K., Murakami, K. K., Thompson, C. C., and Evans, R. M. (1991). Direct repeats as selective response elements for the thyroid hormone, retinoic acid, and vitamin D3 receptors. Cell 65, 1255-1266.

Uomori, A., Seo, S., Sato, T., Yoshimura, Y., and Takeda, K. (1987) Synthesis of (25R)-[26-2H1]Cholesterol and 1H N.m.r. and H.p.l.c. Resolution of (25R)- and (25S)-26-Hydroxycholesterol. J. Chem. Soc. Perkin Trans. 1, 1713-1718.

Van Gilst, M. R., Hadjivassiliou, H., Jolly, A., and Yamamoto, K. R. (2005a). Nuclear hormone receptor NHR-49 controls fat consumption and fatty acid composition in *C. elegans*. PLoS Biol 3, e53.

Van Gilst, M. R., Hadjivassiliou, H., and Yamamoto, K. R. (2005b). From The Cover: A *Caenorhabditis elegans* nutrient response system partially dependent on nuclear receptor NHR-49. Proc Natl Acad Sci USA 102, 13496-13501.

Willy, P. J., Umesono, K., Ong, E. S., Evans, R. M., Heyman, R. A., and Mangelsdorf, D. J. (1995). LXR, a nuclear receptor that defines a distinct retinoid response pathway. Genes Dev 9, 1033-1045.

Xu, H. E., Stanley, T. B., Montana, V. G., Lambert, M. H., Shearer, B. G., Cobb, J. E., McKee, D. D., Galardi, C. M., Plunket, K. D., Nolte, R. T., et al. (2002). Structural basis for antagonist-mediated recruitment of nuclear co-repressors by PPARalpha. Nature 415, 813-817.

Yu, B. and Tao, H. (2002). Journal of Organic Chemistry. 67, 9099-9102.

Zhang, Z., L1, D., Blanchard, D. E., Lear, S. R., Erickson, S. K., and Spencer, T. A. (2001). Key regulatory oxysterols in liver: analysis as delta-4-3-ketone derivatives by HPLC and response to physiological perturbations. Journal of Lipid Research 42, 649-658.

Zheng, Y., and L1, Y. (2003). Novel stereoselective synthesis of 7beta-methyl-substituted 5-androstene derivatives. J. Org. Chem. 68, 1603-1606 (2003)

We claim:

1. A method for controlling the growth of a nematode, comprising contacting the nematode with a biologically effective amount of at least one compound according to formula I or a stereoisomer, or pharmaceutically acceptable salt thereof:

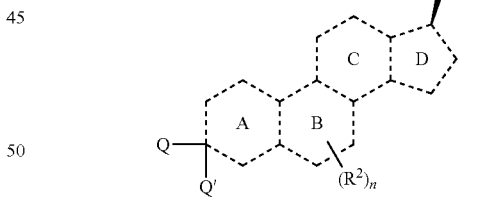

wherein each instance of _____ independently is a single bond or a double bond; one of Q or Q' is OH or SH and the other of Q or Q' is hydrogen, or Q and Q' together with the carbon atom to which they are attached form a carbonyl or thiocarbonyl group; $R^1$ is selected from the group consisting of:

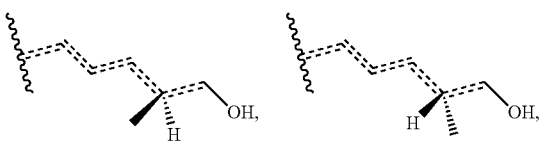

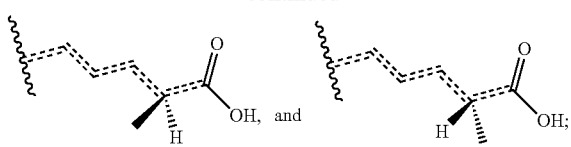

wherein each instance of ==== independently is a single bond, or a double bond; and wherein R¹ is optionally substituted with 1 to 2 substituents, each of which is independently selected from the group consisting of halo, $(C_1-C_8)$alkyl, NRR', OR, and SR; $R_2$ is a substituent on one or more carbon atoms in rings A, B, C, and D and, in each instance, is independently selected from the group consisting of halo, $(C_1-C_8)$alkyl, $(C_1-C_8)$haloalkyl, $(C_1-C_8)$hydroxyalkyl, NRR', oxo, thione, OR, and SR; R and R' are independently selected from the group consisting of hydrogen, $(C_1-C_8)$alkyl, $(C_1-C_8)$fluoroalkyl, and $(C_1-C_8)$hydroxyalkyl; and n is selected from the group consisting of 0, 1, or 2.

2. The method according to claim 1, wherein the compound is selected from the group consisting of:

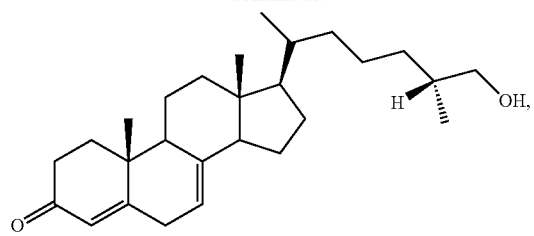

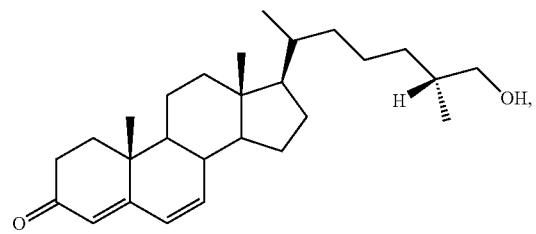

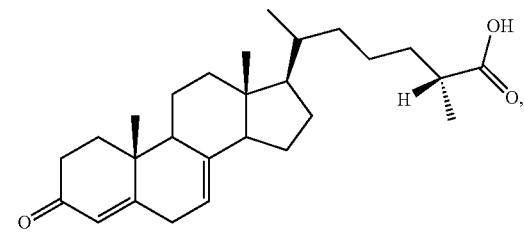

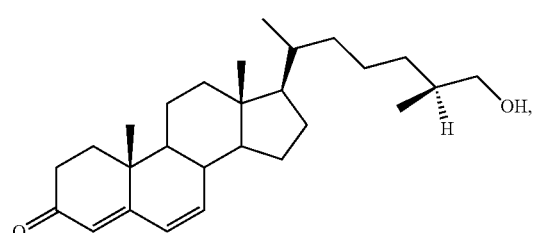

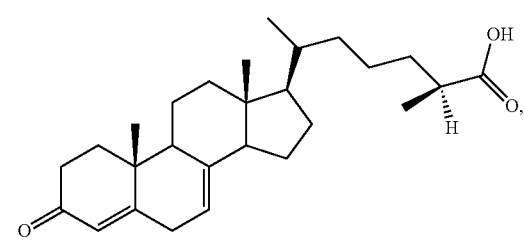

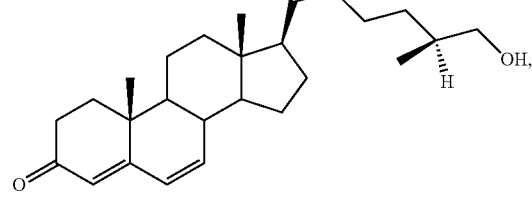

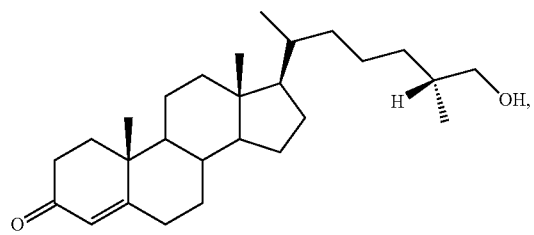

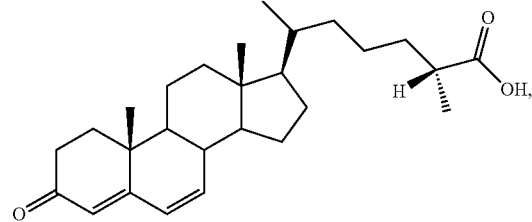

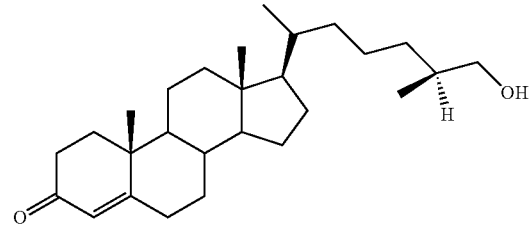

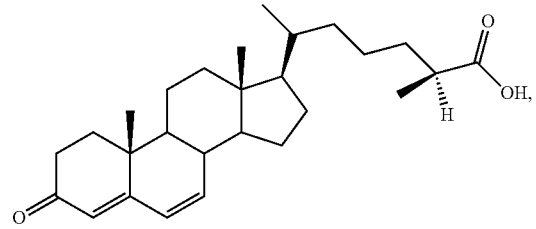

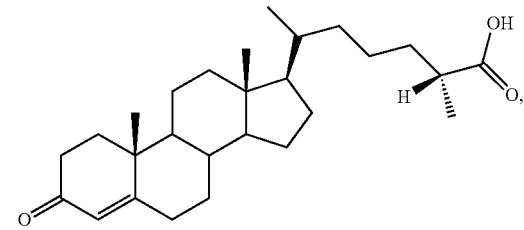

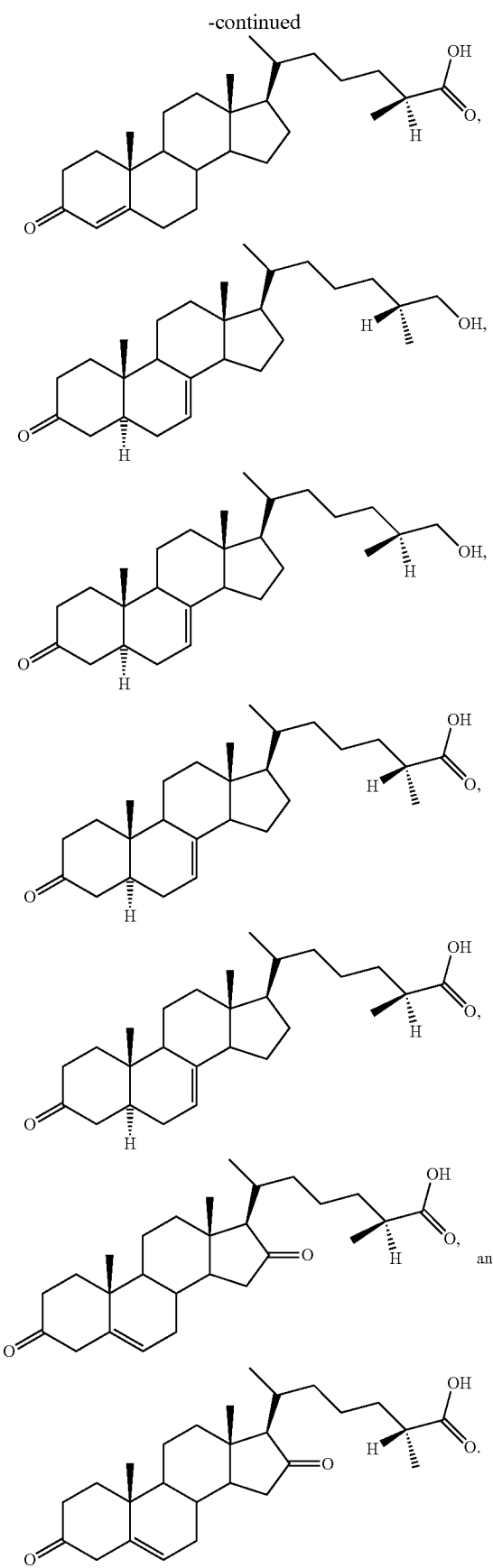

3. The method according to claim 1, wherein the nematode is a parasitic nematode.

4. The method according to claim 3, wherein the parasitic nematode is a member of an order selected from the group consisting of the *Strongylida, Rhabditida, Ascaridida, Spirurida, Oxyurida, Enoplida, Tylenchida*, and *Dorylaimida* nematode orders.

5. The method according to claim 3, wherein the parasitic nematode is a member of a genus selected from the group consisting of *Haemonchus, Oestertagia, Trichostrongylus, Cooperia, Dictyocaulus, Strongylus, Oesophagostomum, Syngamus, Nematodirus, Heligmosomoides, Nippostrongylus, Metastrongylus, Angiostrongylus, Acyclostoma, Necator, Uncinaria, Bunostomum, Strongyloides, Steinemema, Ascaris, Parascaris, Toxocara, Toxascaris, Baylisascaris, Anisakis, Pseudoterranova, Heterakis, Wuchereria, Brugia, Onchocerca, Dirofilaria, Loa, Thelazia, Dracunculus, Gnathostoma, Enterobius, Oxyuris, Syphacia, Trichinella, Trichuris, Capillaria, Globodera, Heterodera, Meloidogyne, Anguina, Ditylenchus, Hirschmanniella, Naccobus, Pratylenchus, Radopholus, Criconema, Tylenchulus, Paratylenchus, Aphelenchus, Bursaphelenchus, Longidorus, Xiphinema, Trichodorus*, and *Paratrichodorus* nematode genera.

6. A method of reducing nematode infestation of a plant that is infested or susceptible to infestation by a nematode population, comprising administering to the plant a biologically effective amount of at least one compound according to formula I or a stereoisomer, or pharmaceutically acceptable salt thereof:

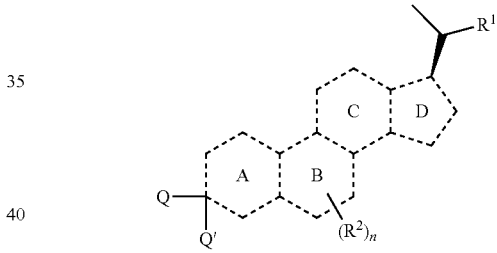

wherein each instance of ———— independently is a single bond or a double bond; one of Q or Q' is OH or SH and the other of Q or Q' is hydrogen, or Q and Q' together with the carbon atom to which they are attached form a carbonyl or thiocarbonyl group; $R^1$ is selected from the group consisting of:

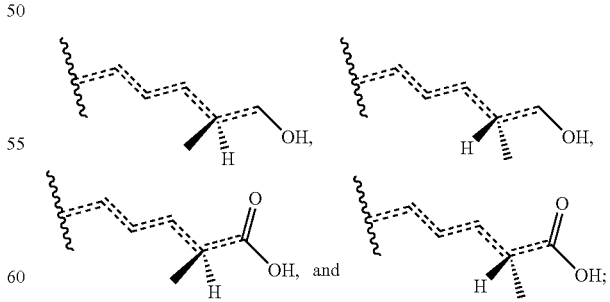

wherein each instance of ==== independently is a single bond, or a double bond and wherein $R^1$ is optionally substituted with 1 to 2 substituents, each of which is independently selected from the group consisting of halo, $(C_1-C_8)$alkyl, $(C_1-C_8)$haloalkyl, $(C_1-C_8)$hydroxyalkyl, NRR', OR, and SR; $R_2$ is a substituent on one or more carbon atoms in rings A, B, C, and D and, in each instance, is independently selected from the group consisting of halo, $(C_1\text{-}C_8)$alkyl, $(C_1\text{-}C_8)$haloalkyl, $(C_1\text{-}C_8)$hydroxyalkyl, NRR', oxo, thione, OR, and SR; R and R' are independently selected from the group consisting of hydrogen, $(C_1\text{-}C_8)$alkyl, $(C_1\text{-}C_8)$fluoroalkyl, and $(C_1\text{-}C_8)$hydroxyalkyl; and n is selected from the group consisting of 0, 1, or 2.

7. The method according to claim 6, wherein the administering comprises treating with the compound soil in which the plant is grown.

8. The method according to claim 6, wherein the administering comprises treating with the compound a seed from which the plant is to be grown.

9. A method of reducing a nematode infestation in a mammal, comprising administering to the mammal a therapeutically effective amount of at least one compound according to formula I or a stereoisomer, or pharmaceutically acceptable salt thereof:

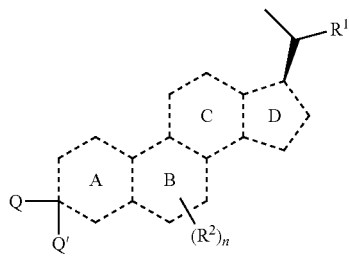

wherein each instance of ____ independently is a single bond or a double bond; one of Q or Q' is OH or SH and the other of Q or Q' is hydrogen, or Q and Q' together with the carbon atom to which they are attached form a carbonyl or thiocarbonyl group; $R^1$ is selected from the group consisting of:

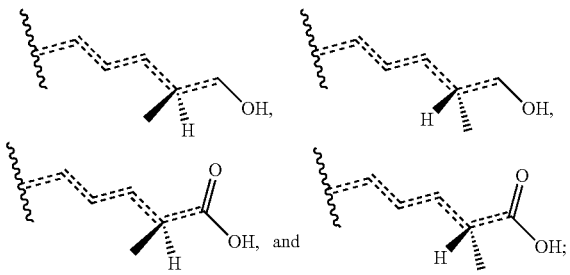

wherein each instance of ==== independently is a single bond, or a double bond and wherein $R^1$ is optionally substituted with 1 to 2 substituents, each of which is independently selected from the group consisting of halo, $(C_1\text{-}C_8)$alkyl, $(C_1\text{-}C_8)$haloalkyl, $(C_1\text{-}C_8)$hydroxyalkyl, NRR', OR, and SR; $R_2$ is a substituent on one or more carbon atoms in rings A, B, C, and D and, in each instance, is independently selected from the group consisting of halo, $(C_1\text{-}C_8)$alkyl, $(C_1\text{-}C_8)$haloalkyl, $(C_1\text{-}C_8)$hydroxyalkyl, NRR', oxo, thione, OR, and SR; R and R' are independently selected from the group consisting of hydrogen, $(C_1\text{-}C_8)$alkyl, $(C_1\text{-}C_8)$fluoroalkyl, and $(C_1\text{-}C_8)$hydroxyalkyl; and n is selected from the group consisting of 0, 1, or 2.

* * * * *

UNITED STATES PATENT AND TRADEMARK OFFICE
CERTIFICATE OF CORRECTION

Page 1 of 1

PATENT NO. : 10,117,878 B2
APPLICATION NO. : 13/673696
DATED : November 6, 2018
INVENTOR(S) : David J. Mangelsdorf et al.

It is certified that error appears in the above-identified patent and that said Letters Patent is hereby corrected as shown below:

On the Title Page

The first or sole Notice should read --

Subject to any disclaimer, the term of this patent is extended or adjusted under 35 U.S.C. 154(b) by 805 days.

In the Claims

In Claim 5, Column 68, Line 15, delete "*Steinemema*" and insert --*Steinernema*-- therefor.

Signed and Sealed this
Sixteenth Day of July, 2019

Andrei Iancu
*Director of the United States Patent and Trademark Office*